US012377275B2

(12) United States Patent
Jackson et al.

(10) Patent No.: US 12,377,275 B2
(45) Date of Patent: *Aug. 5, 2025

(54) DETERMINING RELATIVE PHASE RELATIONSHIPS FOR DELIVERY OF ELECTRICAL STIMULATION THERAPY

(71) Applicant: Medtronic, Inc., Minneapolis, MN (US)

(72) Inventors: Jadin C. Jackson, Roseville, MN (US); Abbey Beuning Holt Becker, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/392,561

(22) Filed: Dec. 21, 2023

(65) Prior Publication Data

US 2024/0139520 A1 May 2, 2024

Related U.S. Application Data

(63) Continuation of application No. 17/077,805, filed on Oct. 22, 2020, now Pat. No. 11,872,402.

(51) Int. Cl.
*A61N 1/00* (2006.01)
*A61N 1/05* (2006.01)
*A61N 1/36* (2006.01)

(52) U.S. Cl.
CPC ....... *A61N 1/36171* (2013.01); *A61N 1/0534* (2013.01); *A61N 1/36067* (2013.01); *A61N 1/36096* (2013.01); *A61N 1/36153* (2013.01)

(58) Field of Classification Search
CPC .............. A61N 1/36171; A61N 1/3616; A61N 1/36064; A61N 1/36082–36103;

(Continued)

(56) References Cited

U.S. PATENT DOCUMENTS 4,445,512 A 5/1984 Krupka et al.
6,711,547 B1 3/2004 Glover et al.
(Continued)

FOREIGN PATENT DOCUMENTS

WO 2016030424 A1 3/2016
WO 2018080653 A1 5/2018

OTHER PUBLICATIONS

Anderson et al., "Phase-dependent stimulation efects on bursting activity in a neural network cortical simulation," National Institutes of Health, Epilepsy Research, vol. 84, No. 1, Mar. 2009, 23 pp.

(Continued)

*Primary Examiner* — Scott M. Getzow
(74) *Attorney, Agent, or Firm* — Shumaker & Sieffert, P.A.

(57) ABSTRACT

This disclosure is directed to devices, systems, and techniques for determining one or more phase relationships. A medical device system includes a memory and processing circuitry in communication with the memory. The processing circuitry is configured to receive a plurality of electrical signals which indicate a phase relationship between two or more tissue regions within a target area of neural tissue of a patient. Additionally, the processing circuitry is configured to determine, based on the plurality of electrical signals, the phase relationship between the two or more tissue regions, and compare the phase relationship with a target phase relationship for the two or more tissue regions within the target area. The processing circuitry is further configured to determine, based on the comparison, one or more parameters of stimulation for delivery to the patient and cause a therapy delivery circuit to determine the stimulation.

20 Claims, 17 Drawing Sheets

(58) Field of Classification Search
CPC .............. A61N 1/0534; A61N 1/36067; A61N 1/36096; A61N 1/36153; A61B 5/369–377
See application file for complete search history.

(56) References Cited

U.S. PATENT DOCUMENTS

| | | | |
|---|---|---|---|
| 7,231,258 B2 | 6/2007 | Moore et al. |
| 7,548,787 B2 | 6/2009 | Feher et al. |
| 8,280,514 B2 | 10/2012 | Lozano et al. |
| 8,615,299 B2 | 12/2013 | Goetz |
| 8,639,335 B2 | 1/2014 | Peichel et al. |
| 8,700,150 B2 | 4/2014 | Libbus et al. |
| 9,119,543 B2 | 9/2015 | Martens |
| 9,572,737 B2 | 2/2017 | McNeely et al. |
| 9,619,621 B2 | 4/2017 | Dicks et al. |
| 9,666,061 B2 | 5/2017 | Reeder et al. |
| 9,813,270 B2 | 11/2017 | Feher |
| 10,095,837 B2 | 10/2018 | Corey et al. |
| 10,529,450 B2 | 1/2020 | Corey et al. |
| 11,045,652 B2 | 5/2021 | Jackson et al. |
| 11,318,296 B2 | 5/2022 | Xiao et al. |
| 2002/0128563 A1 | 9/2002 | Carlson et al. |
| 2003/0236487 A1 | 12/2003 | Knowlton |
| 2004/0073098 A1 | 5/2004 | Geva et al. |
| 2005/0075067 A1 | 4/2005 | Lawson et al. |
| 2006/0025824 A1 | 2/2006 | Freeman et al. |
| 2006/0224191 A1 | 10/2006 | Dilorenzo |
| 2007/0123758 A1 | 5/2007 | Miesel et al. |
| 2007/0265669 A1 | 11/2007 | Roline et al. |
| 2007/0266778 A1 | 11/2007 | Corey et al. |
| 2008/0083414 A1 | 4/2008 | Messerges |
| 2009/0099627 A1 | 4/2009 | Molnar et al. |
| 2009/0264956 A1 | 10/2009 | Rise et al. |
| 2009/0264967 A1 | 10/2009 | Giftakis et al. |
| 2010/0029284 A1 | 2/2010 | Feher |
| 2010/0036269 A1 | 2/2010 | Ferren et al. |
| 2010/0076514 A1 | 3/2010 | Cho et al. |
| 2010/0100153 A1 | 4/2010 | Carlson et al. |
| 2010/0249627 A1 | 9/2010 | Zhang et al. |
| 2011/0190850 A1 | 8/2011 | Reinke et al. |
| 2011/0264165 A1 | 10/2011 | Molnar et al. |
| 2012/0150256 A1 | 6/2012 | Martens |
| 2012/0154582 A1 | 6/2012 | Johnson et al. |
| 2013/0172774 A1 | 7/2013 | Crowder et al. |
| 2013/0218232 A1 | 8/2013 | Giftakis et al. |
| 2014/0074187 A1 | 3/2014 | Molnar |
| 2014/0319921 A1 | 10/2014 | Lisi et al. |
| 2014/0359508 A1 | 12/2014 | Otero Diaz et al. |
| 2016/0296759 A1 | 10/2016 | Cong et al. |
| 2016/0342752 A1 | 11/2016 | Stueckemann et al. |
| 2017/0079585 A1 | 3/2017 | Ney et al. |
| 2017/0188993 A1 | 7/2017 | Hamilton et al. |
| 2017/0259064 A1 | 9/2017 | Wu et al. |
| 2018/0185649 A1 | 7/2018 | Michaeli et al. |
| 2018/0236255 A1 | 8/2018 | Etkin |
| 2018/0353759 A1 | 12/2018 | Starr et al. |
| 2019/0247661 A1 | 8/2019 | Eskandar et al. |
| 2019/0290912 A1 | 9/2019 | Raike et al. |
| 2020/0185093 A1 | 6/2020 | Corey et al. |
| 2020/0360695 A1 | 11/2020 | Widge et al. |
| 2022/0126100 A1 | 4/2022 | Jackson et al. |

OTHER PUBLICATIONS

Bauml et al., "Oscillatory correlates of intentional updating in episodic memory," Neuroimage, vol. 41, No. 2, Jun. 2009, pp. 596-604.
Bi et al., "Synaptic Modifications in Cultured Hippocampal Neurons: Dependence on Spike Timing, Synaptic Strength, and Postsynaptic Cell Type," The Journal of Neuroscience, vol. 18, No. 24, Dec. 15, 1998, 9 pp.
Bliss et al., "Long-Lasting potentiation of Synaptic Transmission in the Dentate Area of the Anaesthetized Rabbit Following Stimulation of the Perforant Path," National Institute for Medical Research, Journal of Physiology, vol. 232, Feb. 12, 1973, 26 pp.
Canolty et al., "High Gamma Power is Phase-Locked to Theta Oscillations in Human Neocortex," Science Magazine, Science, vol. 313, Sep. 15, 2006, 4 pp.
Canolty et al., "The functional role of cross-frequency coupling," Trends in Cognitive Sciences, vol. 14, No. 11, Nov. 2010, 10 pp.
Chang et al., "Normal EEG and Sleep: Adults and Elderly," Chapter 11 Part II, Normal EEG, Electroencephalography: Basic Principals, clinical applications and related fields., Lippincott, Williams and Wilkins, Sixth Edition, 2005, 32 pp.
Chen et al., "Real-Time Brain Oscillation Detection and Phase-Locked Stimulation Using Autoregressive Spectral Estimation and Time-Series Forward Prediction," National Institutes of Health, IEEE Transactions on Biomedical Engineering, vol. 60, No. 3, Mar. 2013, 25 pp.
Cole, "Rectification and Inductance in the Squid Giant Axon," College of Physicians and Surgeons, Retrieved from jpg.rupress.org, The Journal of General Physiology, Sep. 20, 1941, 23 pp.
Colgin et al., "Gamma Oscillations in the Hippocampus," International Union of Physiological Sciences/American Physiological Society, Physiology, vol. 25, Oct. 2010, 11 pp.
Da Silva, EEG Analysis: Theor and Practice, Chapter 54 Part IX, Computer-Assisted EEG Analysis, Electroencephalography: Basic Principals, clinical applications and related fields., Lippincott, Williams and Wilkins, Sixth Edition, 2005, 31 pp.
Da Silva, "Neurocognitive Processes and the EEG/MEG," Chapter 50 Part VII, Evoked Potentials and Event- Related EEG Phenomena, Electroencephalography: Basic Principals, clinical applications and related fields., Lippincott, Williams and Wilkins, Sixth Edition, 2005, 30 pp.
Daitch et al., "Frequency-specific machanism links human brain networks for spatial attention," Proceedings of the National Academy of Sciences (PNAS), vol. 110, No. 48, Nov. 26, 2013, 6 pp.
De Solages et al., "Maximal Subthalamic Beta Hypersynchrony of the Local Field Potential in Parkinson's Disease is Located in the Central Region of the Nucleus," Journal of Neurology, Neurosurgery, and Psychiatry, vol. 82, Jan. 4, 2011, pp. 1387-1389.
Fell et al., "Phase-locking within Human Mediotemporal lobe predicts memory formation," NeuroImage, vol. 43, No. 2, Elsevier, Jul. 22, 2008, 10 pp.
Fell et al., "The role of phase synchronization in memory processes," Nature Review, Neuroscience, vol. 12, No. 2, Macmillan Publishers Limited, Feb. 2011, 15 pp.
Gunalan et al., "Creating and Parameterizing Patient-Specific Deep Brain Stimulation Pathway-Activation Models Using the Hyperdirect Pathway as an Example," PLoS ONE, vol. 12, No. 4, Apr. 25, 2017, 19 pp.
Hanslmayr et al., "Prestimulus Oscillatory Phase at 7 Hz Gates Cortical Information Flow and Visual Perception," Current Biology vol. 23, No. 22, Nov. 18, 2013, 6 pp.
Holscher et al., "Stimulation on the Positive Phase of Hippocampal Theta Rhythm Induces Long-Term Potentiation that Can Be Depotentiated by Stimulation on the Negative Phase in Area CA1 In Vivo," The Journal of Neuroscience, vol. 17, No. 16, Aug. 15, 1997, 8 pp.
Horn et al., "Toward an Electrophysiological "Sweet Spot" for Deep Brain Stimulation in the Subthalamic Nucleus," Human Brain Mapping, Mar. 2017, 14 pp.
Hutcheon et al., "Resonance, Oscillation and the Intrinsic Frequency Preferences of Neurons," Trends in Neuroscience (TINS), vol. 23, No. 5, available online May 3, 2000, 7 pp.
Hyman et al., "Stimulation in Hippocampal Region CA1 in Behaving Rats Yields Long-Term Potentiation when delivered to the Peak of Theta and Long-Term Depression when Delivered to the Trough," The Journal of Neuroscience, vol. 23, No. 37, Dec. 17, 2003, 7 pp.
International Preliminary Report on Patentability from International Application No. PCT/US2021/053993 dated May 4, 2023, 8 pp.
International Search Report and Written Opinion of International Application No. PCT/US2021/053993, dated Feb. 4, 2022, 13 pp.
Jackson et al., "Computationally efficient, configurable, causal, real-time phase detection applied to local filed potential oscilla-

(56) References Cited

OTHER PUBLICATIONS tions," Neuromodulation Divsion, Medtronic INC, Conference of Neural Engineering, 7 International IEEE/EMBS, Apr. 22-24, 2015, 6 pp.

Jacobs et al., "Brain Oscillations Control Timing of single-Neuron Activity in Humans," The Journal of Neuroscience, vol. 27, No. 14, Apr. 4, 2007, 6 pp.

Lebedev et al., "Brain-machine interfaces: past, present and future," Trends in Neurosciences, vol. 29, No. 9, Science Direct, Jul. 21, 2006, 11 pp.

Lega et al., "Human Hippocampal Theta Oscillations and the Formation of Episodic Memories," Hippocampus, vol. 22, No. 4, Apr. 27, 2011, 14 pp.

Pavlides et al., "Long-term potentiation in the dentate gyrus is induced preferentially on the positive phase of 0 rhythm," Brain Research, Elsevier, vol. 439, No. 1/2, Jan. 26, 1988, 7 pp.

Pfurtscheller et al., EEG Event-Related Desynchronization (ERD) and Event- Related Synchronizations (ERS), Chapter 45 Part VII, Evoked Potentials and Event- Related EEG Phenomena, Electro-encephalography: Basic Principals, clinical applications and related fields., Lippincott, Williams and Wilkins, Sixth Edition, 2005, 14 pp.

Prosecution History from U.S. Appl. No. 17/077,805, dated Apr. 18, 2022 through Sep. 5, 2023, 97 pp.

Puil et al., "Quantification of Membrane Properties of trigeminal Root Ganglion Neurons in Guinea Pigs," Journal of Neurophyiology, vol. 55, No. 5, The American Physiological Society, May 1986, 22 pp.

Rizzuto et al., "Human neocortical oscillations exhibit theta phase differences between encoding and retrieval," NeuroImage, vol. 31, Science Direct, Elsevier, Mar. 15, 2006, 7 pp.

Rutishauser et al., "Human Memory Strength is Predicted by Theta-frequency phase-locking of single neurons," Nature Publishing Group, vol. 464, Apr. 8, 2010, 8 pp.

Sauseng et al., "What does phase information of oscillatory brain activity tell US about cognitive processes?," Science Direct, Elsevier Ltd., Neuroscience and Biobehavioral Reviews, Mar. 29, 2008, 13 pp.

Tinkhauser et al., "Directional Local Field Potentials: A Tool to Optimize Deep Brain Stimulation," Movement Disorders, Nov. 2017, 6 pp.

Van Zaen et al., "Adaptive tracking of EEG oscillations," Journal of Neuroscience Methods, vol. 186, Elsevier, Oct. 23, 2009, 10 pp.

Zaidel et al., "Subthalamic Span of B Oscillations Predicts Deep Brain Stimulation Efficacy for Patients with Parkinson's Disease," Brain, vol. 133, Jun. 9, 2010, pp. 2007-2021.

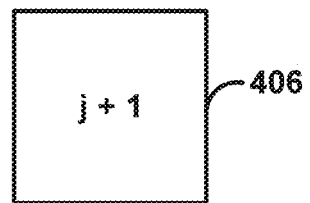
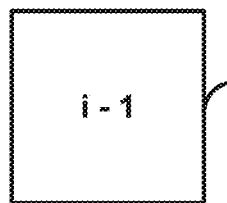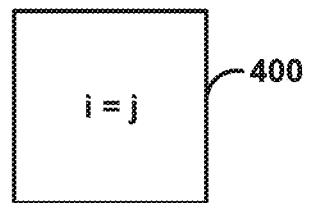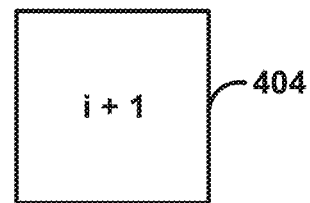
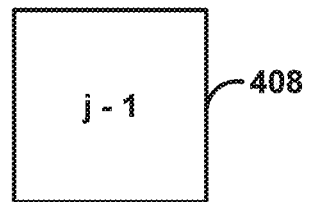
FIG. 4A

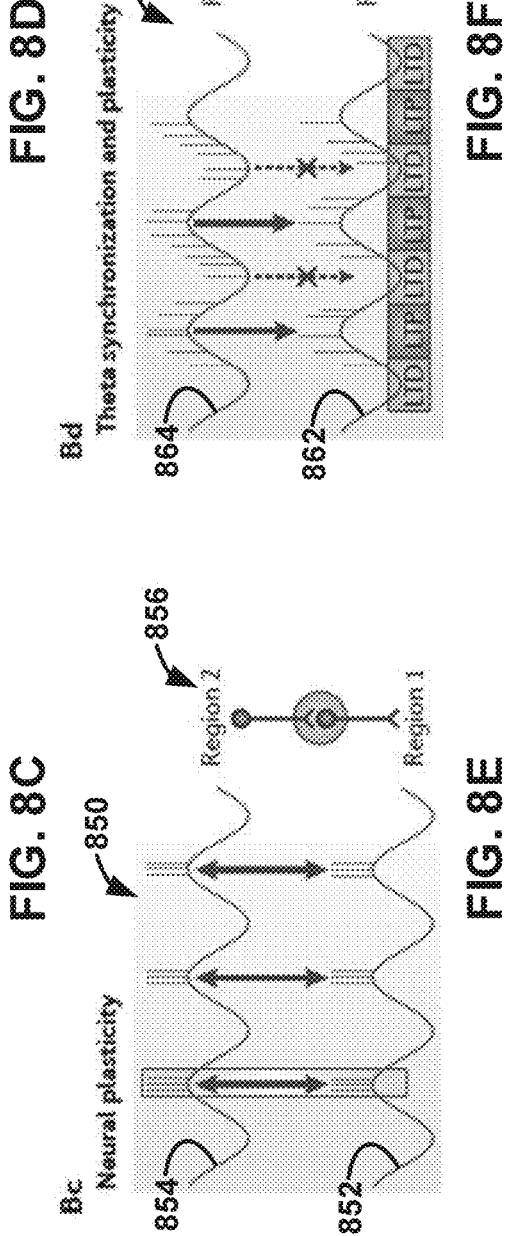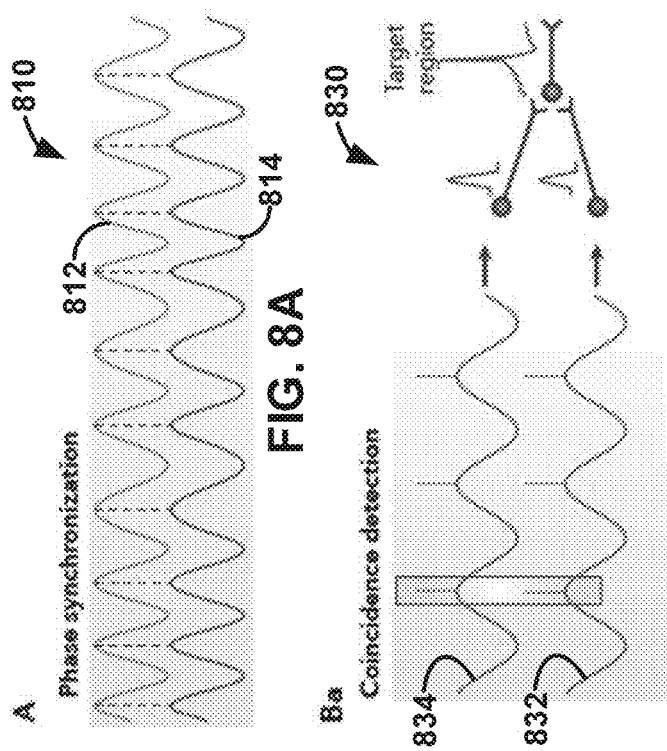

DETERMINING RELATIVE PHASE RELATIONSHIPS FOR DELIVERY OF ELECTRICAL STIMULATION THERAPY

This application is a continuation of U.S. patent application Ser. No. 17/077,805, filed on Oct. 22, 2020, the entire content of which is incorporated herein by reference.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device delivers electrical stimulation therapy via one or more leads that include electrodes located proximate to target locations associated with the brain, the spinal cord, pelvic nerves, peripheral nerves, or the gastrointestinal tract of a patent. For bipolar stimulation, the electrodes used for stimulation may be on one or more leads. For unipolar stimulation, the electrodes may be on one or more leads, and an electrode on a stimulator housing located remotely from the target site. It may be possible to use leadless stimulation using electrodes mounted on the stimulation housing. Electrical stimulation is used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current pulse amplitude, a pulse width, and a pulse frequency as stimulation parameters. A set of parameters, such as a set including electrode combination, electrode polarity, amplitude, pulse width, and pulse rate, may be referred to as a program in the sense that they define the electrical stimulation therapy to be delivered to the patient.

SUMMARY

This disclosure describes one or more example techniques for monitoring phase relationships between electrical signals received by a medical device, and to deliver therapy that causes the phase relationship to approach a target phase relationship. For example, the medical device may be coupled to a plurality of electrodes and the medical device may receive, via each electrode of the plurality of electrodes, a time-varying electrical signal. In this way, the medical device receives a plurality of time-varying electrical signals, each time-varying electrical signal of the plurality of time-varying electrical signals corresponding to a respective electrode of the plurality of electrical signals. The medical device may determine one or more phase relationships based on the plurality of electrical signals. For example, the medical device may determine a difference in phase between two or more of the plurality of electrical signals. The difference in phase between two electrical signals may be indicative of a time difference between location of two corresponding points on the two electrical signals. For instance, the time difference between a peak in a first electrical signal and a closest peak in a second electrical signal may be indicative of the phase difference between the first and second electrical signals.

Based on the plurality of time-varying electrical signals, the medical device may determine a measurement of current source densities (CSD) corresponding to each electrode of the plurality of electrodes. The CSD measurements may be time-varying voltage measurements. In some examples, the medical device may determine a phase of the electrical signals based on the CSD measurements and determine a phase relationship based on the determined phase. In some cases, processing circuitry (e.g., processing circuitry of the medical device and/or other processing circuitry), may determine one or more parameters for electrical stimulation therapy in order to cause a phase relationship to approach a target phase relationship.

The techniques of this disclosure may provide one or more advantages. For example, it may be beneficial for the medical device to determine one or more phase relationships between tissue regions of the brain based on a plurality of time-varying measurements of CSD corresponding to the plurality of electrodes. The medical device may determine electrical stimulation based on the time-varying measurements of CSD and deliver the electrical stimulation to the patient in order to cause a phase relationship to approach a target phase relationship. In some examples, the target phase relationship may represent a synchronous phase relationship or a non-synchronous phase relationship. When the phase relationship between the tissue regions is a synchronous phase relationship, a level of neural communication may exist between the tissue regions. When the phase relationship between the tissue regions is a non-synchronous phase relationship, a level of neural communication might not exist between the tissue regions. Consequently, controlling the phase relationship to approach the target phase relationship may affect a level of neural communication between the tissue regions corresponding to the phase relationship. The level of communication between regions of the brain may have an effect on one or more patient conditions such as involuntary tremors and/or seizures. Controlling the level of neural communication may decrease a severity of one or more patient conditions as compared with medical device systems which do not cause relative phase relationships to approach target phase relationships.

In some examples, a medical device system includes a memory and processing circuitry in communication with the memory. The processing circuitry is configured to receive, via one or more electrodes of a plurality of electrodes, a plurality of electrical signals which indicate a phase relationship between two or more tissue regions within a target area of neural tissue of a patient; determine, based on the plurality of electrical signals, the phase relationship between the two or more tissue regions; and compare the phase relationship with a target phase relationship for the two or more tissue regions within the target area. Additionally, the processing circuitry is configured to determine, based on the comparison of the phase relationship and the target phase relationship, one or more parameters of stimulation for delivery to the patient; and cause a therapy delivery circuit to determine the stimulation based on the determined one or more parameters.

In some examples, a method includes receiving, by processing circuitry in communication with a memory via one or more electrodes of a plurality of electrodes, a plurality of electrical signals which indicate a phase relationship between two or more tissue regions within a target area of neural tissue of a patient, determining, based on the plurality of electrical signals, the phase relationship between the two or more tissue regions, and comparing the phase relationship with a target phase relationship for the two or more tissue regions within the target area. Additionally, the method includes determining, based on the comparison of the phase relationship and the target phase relationship, one or more parameters of stimulation for delivery to the patient, and causing a therapy delivery circuit to determine the stimulation based on the determined one or more parameters.

In some examples, a computer-readable storage medium includes instructions that when executed cause one or more processors to receive, via one or more electrodes of a plurality of electrodes, a plurality of electrical signals which indicate a phase relationship between two or more tissue regions within a target area of neural tissue of a patient, determine, based on the plurality of electrical signals, the phase relationship between the two or more tissue regions, and compare the phase relationship with a target phase relationship for the two or more tissue regions within the target area. Additionally, the instructions cause the one or more processors to determine, based on the comparison of the phase relationship and the target phase relationship, one or more parameters of stimulation for delivery to the patient, and cause a therapy delivery circuit to determine the stimulation based on the determined one or more parameters.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF DRAWINGS

FIG. 4A is a conceptual diagram illustrating a first example of electrodes on a lead with which current source density (CSD) measurements are performed, in accordance with one or more techniques of this disclosure.

FIGS. 8A-8F are graphs illustrating a set of plots which indicate a relationship between pairs of physiological signals, in accordance with one or more techniques of this disclosure.

DETAILED DESCRIPTION

Figure 1:
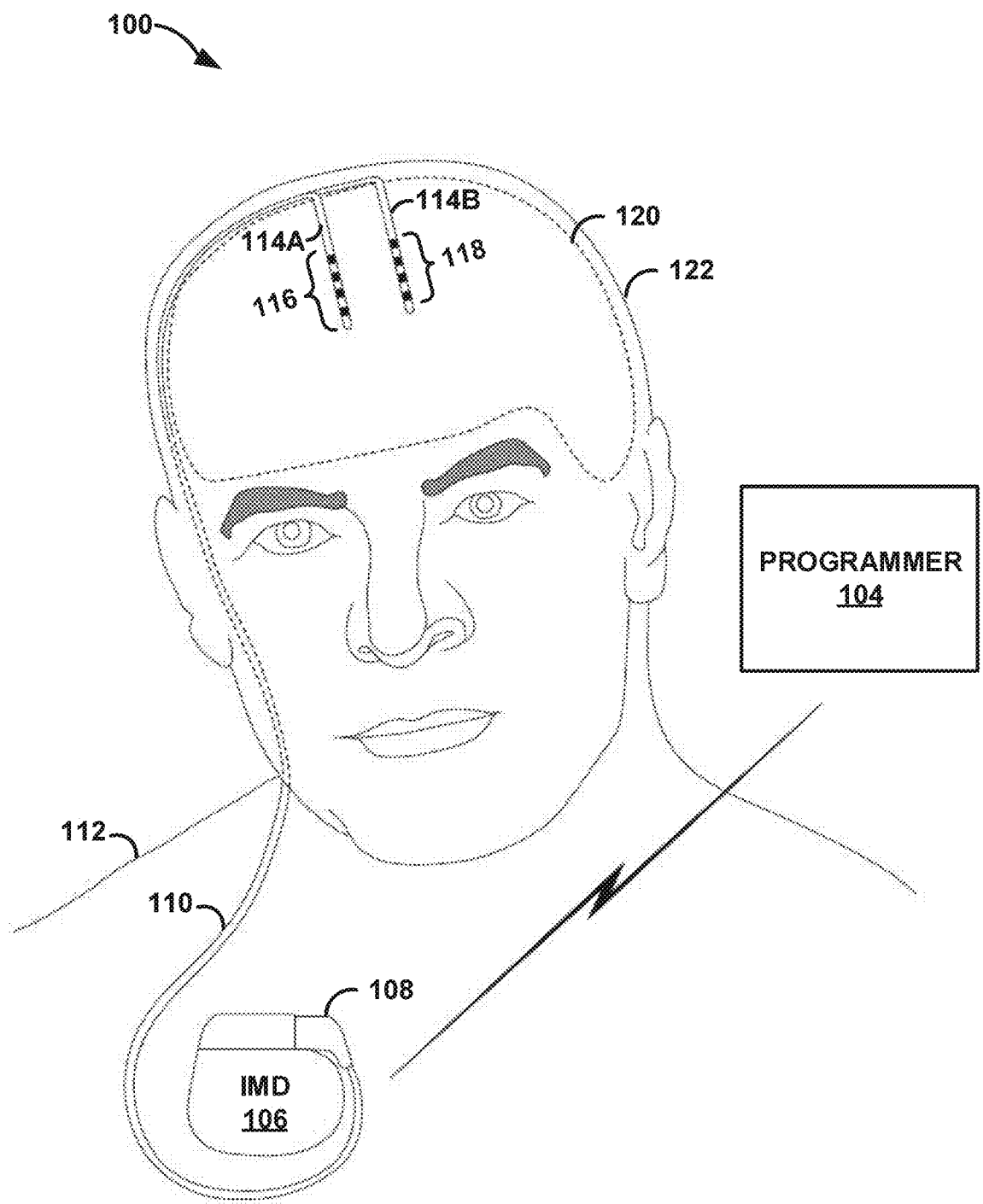
FIG. 1 is a conceptual diagram illustrating an example system that includes an implantable medical device (IMD) configured to deliver deep brain stimulation to a patient based on one or more phase relationship measurements, in accordance with one or more techniques of this disclosure.

This disclosure describes example techniques to monitor one or more phase relationships between tissue regions of a target area of a patient. For example, an implantable medical device (IMD) may receive a plurality of time-varying electrical signals, each time-varying electrical signal of the plurality of time-varying electrical signals corresponding to a respective electrode of a plurality of electrodes. Processing circuitry (e.g., processing circuitry of the IMD or other processing circuitry) may determine a current source density (CSD) corresponding to each electrode of the plurality of electrodes and subsequently determine, based on the respective CSDs, one or more phase relationships between tissue regions of the target area.

The IMD may determine one or more parameters of electrical signals delivered to the patient based on one or more determined phase relationships. For example, the IMD may execute a phase relationship measurement in order to determine a set of phase relationships corresponding to electrical signals received by IMD via a plurality of electrodes. In some cases, the IMD may receive a time-varying voltage signal from each electrode of the plurality of electrodes. The IMD may calculate, based on the time-varying voltage signal corresponding to each electrode of the plurality of electrodes, a respective time-varying measurement of CSD corresponding to each electrode of the plurality of electrodes. The IMD may determine a phase-magnitude representation of each respective time-varying measurement of CSD in order to determine a phase corresponding to each electrode of the plurality of electrodes. The IMD may determine one or more phase relationships based on the phase corresponding to each electrode of the plurality of electrodes.

A phase relationship between, for example, a first brain tissue region and a second brain tissue region may affect a neural communication between the first brain tissue region and the second brain tissue region. Such neural communication between brain tissue regions or lack thereof may cause one or more symptoms (e.g., Parkinson's tremors, seizures) to manifest in a patient. The IMD may deliver one or more electrical signals to the patient in order to control phase relationships between brain tissue regions so that one or more patient symptoms are attenuated and/or improved. For example, controlling the one or more phase relationships to approach one or more respective target phase relationships may decrease a severity of Parkinson's tremors and/or improve one or more other patient conditions.

One or more techniques described herein may improve a manner in which the IMD manages the interaction of electrical stimulation with on-going neural activity in the patient as compared with one or more systems which do not measure phase relationships between electrodes. Neural dynamics may be affected by oscillations in local electrical fields within target tissue. Stimulating at particular phases of a neural oscillation can have additive or destructive effects on the dynamics of the network oscillations, synchronizing or desynchronizing neuronal activity related to the generation of those oscillations. That is, the IMD may deliver electrical stimulation to a target area of the brain in order to facilitate communication between two or more regions of the target area or inhibit communication between two or more regions of the target area. Phase relationship measurements allow the IMD to control the phase of different regions of the target tissue and consequently control neural activity within the different regions.

For example, phase-specific stimulation of the ventral intermediate nucleus of the thalamus can reduce tremors which may arise from the phase desynchronization of signals generated in tissue in the motor system of the patient. Similarly, controlling one or more regional phase synchronizations and/or one or more regional phase desynchronizations may decrease a likelihood of the patient experiencing a seizure or otherwise improve one or more patient conditions associated with epilepsy. In the case of Parkinson's disease, a "coordinated reset" of pathological oscillations may lead to the development of spatially distributed patterned stimulation to evoke long-lasting therapeutic improvement. Consequently, one or more techniques to estimate phase relationships in local and regional networks and utilize those phase relationships to deliver phase-targeted stimulation to specific regions of the brain may be beneficial for improving one or more patient conditions. Tissue (e.g., brain tissue) which generates biological signals may be referred to herein as "oscillators."

Stimulating tissue regions of the brain on order to control one or more phase relationships between the tissue regions may decrease an amount of power consumed by the medical device as compared with medical device systems which do not control phase relationships between tissue regions of the brain. For example, when a level of neural communication exists between a first tissue region and a second tissue region, it may be possible for the medical device to cause neural activity to occur in both of the first tissue region and the second tissue region by stimulating only one of the tissue regions. A clinician may select one or more target phase relationships such that when the medical device causes the relative phase relationships to approach the one or target phase relationships, the medical device may improve an energy efficiency of delivering electrical stimulation to the brain as compared with medical device systems which do not control phase relationships between tissue regions of the brain.

FIG. 1 is a conceptual diagram illustrating an example system 100 that includes an IMD 106 configured to deliver deep brain stimulation (DBS) to a patient 112 based on one or more phase relationship measurements, in accordance with one or more techniques of this disclosure. DBS may be adaptive in the sense that IMD 106 may adjust, increase, or decrease the magnitude of one or more parameters of the DBS in response to changes in patient activity or movement, a severity of one or more symptoms of a disease of the patient, a presence of one or more side effects due to the DBS, or one or more sensed signals of the patient.

For instance, one example of system 100 is a bi-directional DBS system with capabilities to both deliver stimulation and sense intrinsic neuronal signals. System 100 provides for "closed-loop" therapy where IMD 106 may continuously monitor the state of certain biomarker signals and deliver stimulation according to pre-programmed routines based on the biomarker signals. Biomarker signals may include, in some cases, physiological brain signals originating within brain tissue. For example, biomarker signals monitored by IMD 106 may include beta frequency band activity recorded in brain 120 of patient 112, however this is not required. Biomarker signals may additionally or alternatively include other brain signals such as the delta frequency band, the theta frequency band, the gamma frequency band, or the high gamma frequency band and/or other biometric signals such as an electrogram (EGM).

System 100 may be configured to treat a patient condition, such as a movement disorder, neurodegenerative impairment, a mood disorder, or a seizure disorder of patient 112. Patient 112 ordinarily is a human patient. In some cases, however, system 100 may be applied to other mammalian or non-mammalian, non-human patients. While movement disorders and neurodegenerative impairment are primarily referred to herein, in other examples, system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

As seen in FIG. 1, system 100 includes programmer 104, IMD 106, lead extension 110, and leads 114A and 114B with respective sets of electrodes 116 and electrodes 118 (collectively, "electrodes 116, 118"). In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver electrical stimulation to brain 120. In other examples, all of electrodes 116, 118 are configured to both sense neurological brain signals and deliver electrical stimulation to brain 120. In some examples, unipolar stimulation may be possible where one electrode is on the housing of IMD 106 or at another position remote from the distal ends of leads 114A, 114B.

IMD 106 includes a stimulation generator (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, neurological signals sensed within brain 120 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, the bioelectric signals are LFPs, if measured on the cortex, the bioelectric signals are EcoG signals, and if on scalp, the bioelectric signals are EEG signals. In this disclosure, the term "oscillatory signal source" is used to describe a signal source that generates bioelectric signals.

Neurological signals sensed within brain 120 may be leveraged in order to determine therapy (e.g., electrical stimulation pulses) delivered to patient 105 by IMD 106 and/or other devices. For example, it may be desired to decrease an amount of energy consumed by IMD 106 in delivering therapy and increase an efficacy of therapy delivered to patient 112 as compared with one or more other systems. For example, system 100 may perform any one or combination of sense neurological signals, perform real-time phase detection, determine one or more measurements of CSD, determine one or more phase-magnitude representations of the measurements of CSD, and implement closed-loop algorithms in order to deliver therapy to patient 105 in a more energy efficient and a more effective way as compared with other systems which do not implement these techniques. In some examples, one or more techniques of this disclosure implement neurological signal sensing, real-time phase detection, and CSD estimation in order to achieve a lower-energy, more-efficacious delivery of therapy to patient 105. For example, IMD 106 may execute a closed-loop algorithm to identify, measure, and target patient-specific network dynamics in order to deliver therapy to patient 105.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as an oscillatory signal source, within the brain of the patient, that outputs an oscillatory electrical voltage signal that is sensed by one or more of electrodes 116 and/or 118.

In some examples, the neurological brain signals that are used to determine one or more phase relationships may be sensed within the same region of brain 120 as the target tissue site for the electrical stimulation. These tissue sites may include tissue sites within anatomical structures such as the thalamus (e.g., the ventral intermediate nucleus of the thalamus), subthalamic nucleus or globus pallidus of brain 120, as well as other target tissue sites. The specific target tissue sites and/or regions within brain 120 may be selected based on the patient condition. Thus, in some examples, both a stimulation electrode combination and sense electrode combinations may be selected from the same set of electrodes 116, 118. In other examples, the electrodes used for delivering electrical stimulation may be different than the electrodes used for sensing neurological brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a selected therapy program. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

In some examples, electrodes 116, 118 may be radially-segmented DBS arrays (rDBSA) of electrodes. Radially-segmented DBS arrays refer to electrodes that are segmented radially along the lead. As one example, leads 114A and 114B may include a first set of electrodes arranged circumferentially around leads 114A and 114B that are all at the same height level on leads 114A and 114B (e.g., same axial position along length of leads 114A and 114B). Each of the electrodes in the first set of electrodes is a separate segmented electrode and form a level of radially-segmented array of electrodes. Leads 114A and 114B may include a second set of electrodes arranged circumferentially around leads 114A and 114B that are all at the same height level on leads 114A and 114B. Each of the electrodes in the first set of electrodes is a separate segmented electrode and form a level of radially-segmented array of electrodes. The rDBSA electrodes may be beneficial for directional stimulation and sensing.

The signal component in the beta frequency band is described as one example, and the techniques are applicable to other types of LFP activity. Furthermore, the example techniques are not limited to examples where electrodes 116, 118 are an rDBSA of electrodes. The example of using rDBSA of electrodes is described as a way of directional stimulation and sensing. However, the example techniques are also useable in examples where directional stimulation and sensing are not available or are not used. Moreover, there may be other ways of performing directional stimulation and sensing that do not require the use of an rDBSA of electrodes.

Physiological signals sensed in the brain 120 of patient 112 may be associated with one or more phase values. For example, each electrode of the plurality of electrodes 116, 118 may sense one or more physiological signals, and IMD 106 may execute techniques described herein to identify a phase corresponding to respective physiological signals sensed by IMD 106 via each electrode of the plurality of electrodes 116, 118. In this way, IMD 106 may determine a phase corresponding to each tissue region of a set of tissue regions in brain 120, where each tissue region of the set of tissue regions represents a volume of tissue corresponding to (e.g., proximate to) a respective electrode of electrodes 116, 118.

IMD 106 may perform phase relationship measurements in order to determine one or more phase relationships between respective tissue regions of the set of tissue regions of brain 120. For example, IMD 106 may sense an electrical signal corresponding to each electrode of electrodes 116, 118. Based on the received electrical signals, IMD 106 may determine a phase associated with the respective tissue region corresponding to each electrode of electrodes 116, 118. IMD 106 may determine, based on the determined phases, a set of phase relationships between one or more pairs of tissue regions. These phase relationships may be determined in the form of a phase-magnitude relationship which identifies a phase of one or more tissue regions with respect to a reference phase.

IMD 106 may control one or more phase relationships between tissue regions of brain 120 in order to improve one or more patient conditions. For example, a patient condition may be affected by phase relationships of physiological signals between tissue regions of brain 120, and IMD 106 may control one or more phase relationships to approach target phase relationships in order to improve one or more adverse patient conditions such as Parkinson's tremors.

IMD 106 may control phase relationships of physiological signals within brain 120 by stimulating brain 120 with electrical signals at a phase which is "desired" for a respective tissue region of brain 120. For example, IMD 106 may deliver a first electrical signal at a first phase via a first electrode of electrodes 116, 118 and deliver a second electrical signal at a second phase via a second electrode of electrodes 116, 118. The first electrical signal may cause physiological signals within a first tissue region corresponding to the first electrode to occupy the first phase and the second electrical signal may cause physiological signals within a second tissue region corresponding to the second electrode to occupy the second phase. A "phase relationship" between the first tissue region and the second region may represent a relationship between the first phase and the second phase. As such, IMD 106 may control the phase relationship between the first tissue region and the second tissue region by controlling the phase of the electrical stimulation delivered to the first tissue region and the second tissue region, respectively. In some examples, a phase relationship between a first signal and a second signal may represent one of a "synchronous" phase relationship or a "non-synchronous" phase relationship.

As described in more detail, some of the algorithms described in this disclosure may be used to determine the most proximate electrodes of electrodes 116, 118 to the oscillatory signal source. In some examples, the electrodes of electrodes 116, 118 that are most proximate to the oscillatory source tend to be the electrodes with which electrical stimulation should be delivered. In some examples, electrodes 116, 118 that are most distal to the oscillatory signal source may be the electrodes that should be used for stimulation. In some examples, electrodes 116, 118 between the most distal and most proximate electrodes should be used for stimulation. Hence, determining which electrodes 116, 118 are most proximate and distal may be useful in determining which electrodes 116, 118 to use for stimulation.

For instance, it may be easier to steer current to proximate electrodes to form the electrical field to impact the oscillatory signal source. Producing the appropriate electrical field from further away electrodes may require more power and can also result in stimulating more tissue other than the tissue of the oscillatory signal source.

One or more electrodes of the plurality of electrodes 116, 118 that are most proximate to the oscillatory signal source may be the electrodes having the highest CSD. For instance, electrodes of electrodes 116, 118 that have the highest CSD are also the closest to the oscillatory signal source.

Because the oscillatory signal source outputs an oscillatory signal (e.g., time-varying signal), the voltages generated at electrodes 116, 118 are also oscillatory. The CSD is determined based on the voltages at electrodes 116, 118. Determining an instantaneous measurement of the voltage provides an instantaneous measurement of the CSD. However, an instantaneous measurement of the CSD may not reflect the actual measurement of the CSD. Accordingly, in example techniques described in this disclosure, IMD 106 may determine, for one or more electrodes of the plurality of electrodes 116, 118, respective time-varying measurements of the CSD. Example techniques to determine the time-varying measurements of the CSD are described in more detail below. IMD 106 may aggregate the respective time-varying measurements of the CSDs to generate respective average level values for one or more electrodes of the plurality of electrodes 116, 118 (e.g., determine a root-mean-square (RMS) value).

However, the average level value of the CSDs may lack information about the phase of the time-varying measurements of the CSDs. Accordingly, IMD 106 may be configured to determine respective phase-magnitude representations of the time-varying measurements of the CSDs. The respective phase-magnitude representations are indicative of the respective amplitudes of frequency components of the respective time-varying measurements of the CSDs at different phases. Example techniques to determine the phase-magnitude representations are described in more detail below. IMD 106 may generate information indicative of the respective average level values and respective phase-magnitude representations.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may include a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres (or in just one hemisphere in some examples), respectively, of patient 112 in order to deliver electrical stimulation to one or more regions of brain 120, which may be selected based on the patient condition or disorder controlled by system 100. The specific target tissue site and the stimulation electrodes used to deliver stimulation to the target tissue site, however, may be selected, e.g., according to the identified patient behaviors and/or other sensed patient parameters. For example, the target tissue site may be the location of the oscillatory signal source that generates the bioelectric signal having a signal component in the beta frequency band. The stimulation electrodes used to deliver stimulation to the target tissue site may be those that are most proximate to the oscillatory signal source, e.g., using the example techniques described in this disclosure. Alternatively, the stimulation electrodes used to deliver stimulation to the target tissue site may be those that are most distal to the oscillatory signal source, e.g. in order to avoid producing a side effect or to activate an inactive circuit. For example, gamma oscillations may occur due to over stimulation and therefore, it may be desirable to not output stimulation on electrodes that are proximate to the signal source of the gamma oscillations to reduce the over stimulation.

Other lead 114 and IMD 106 implant sites are contemplated. For example, IMD 106 may be implanted on or within cranium 122, in some examples. Leads 114A and 114B may be implanted within the same hemisphere or IMD 106 may be coupled to a single lead implanted in a single hemisphere, in some examples.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because ring electrodes are relatively simple to program and are capable of delivering an electrical field to any tissue adjacent to electrodes 116, 118. In other examples, electrodes 116, 118 may have different configurations. For example, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue.

In some examples, a housing of IMD 106 may include one or more stimulation and/or sensing electrodes. In some examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the parameters of the selected therapy program to manage the patient symptoms associated with a movement disorder.

Programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrodes 116, 118, initial programs defining therapy parameter values, and any other information the clinician desires to program into IMD 106. Programmer 104 may also be capable of completing functional tests (e.g., measuring the impedance of electrodes 116, 118 of leads 114).

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combinations with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

However, as described in this disclosure, in some examples, IMD 106 or programmer 104 (e.g., a medical device), alone or in combination, may automatically determine electrode configuration and therapy parameters. For example, the medical device may determine which electrodes to use for stimulation based on which electrodes are most proximate to the oscillatory signal source. In some examples, programmer 104 may output information indicating the selected electrode configuration for stimulation and the determined stimulation amplitude or other therapy parameter for the clinician or physician to review and confirm before IMD 106 delivers therapy via the selected electrode configuration with the determined stimulation amplitude. In some examples, the example techniques may be performed in a cloud computing environment where computing devices are distributed in a cloud computing system and the example techniques are performed in the distributed computing devices of the cloud computing system.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 104 may include an alert LED, may flash a message to patient 112 via a programmer display, generate an audible sound or somatosensory cue to confirm patient input was received, e.g., to indicate a patient state or to manually modify a therapy parameter.

System 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112. Further, an IMD may provide other electrical stimulation such as spinal cord stimulation to treat a movement disorder or pelvic floor stimulation. IMD 106 may, in some cases, execute a closed-loop algorithm in order to modulate a phase of one or more electrical signals. In some examples, a provision of stimulation or an amplitude of stimulation could be conditioned upon the relative amplitude of the real-time phase estimate of the signal. For example, one or more electrical signals received by IMD 106 via electrodes 116, 118 may indicate a respective local field potential (LFP). When IMD 106 identifies an LFP corresponding to an electrical signal, IMD 106 may determine a phase of the LFP and an amplitude of the LFP.

In some examples, IMD 106 may sense one or more electrical signals from electrodes 116, 118 which represent real-time measurements of LFP. IMD 106 may determine, based on the real-time measurements of LFP received by IMD 106, a respective phase relationship between one or more pairs of electrodes while IMD 106 is not delivering electrical stimulation to patient 105. IMD 106 may receive, from each electrode of electrodes 116, 118, an electrical signal representing a time-varying measurement of LFP, where the time-varying measurement of LFP indicates a time-varying measurement of one or more physiological signals within a tissue region corresponding to the respective electrode of electrodes 116, 118. IMD 106 may determine a set of time varying measurements of CSD based on the set of time-varying measurements of LFP received from electrodes 116, 118, where each time-varying measurement of CSD corresponds to a respective electrode of electrodes 116, 118. As such, each time-varying measurement of CSD corresponds to a respective tissue region associated with the electrode corresponding to the respective time-varying measurement of CSD.

In some examples, IMD 106 may determine, based on the time-varying measurements of CSD, one or more parameters for electrical stimulation to be delivered to patient 105. IMD 106 may deliver the electrical stimulation therapy to brain 120 based on the determined one or more parameters. While IMD 106 is delivering electrical stimulation to brain 120, IMD 106 may perform one or more real-time phase measurements and continuously adjust relative timing of electrical stimulation pulses delivered via electrodes 116, 118 based on the relative real-time phase measurements. The real-time phase measurements IMD 106 may allow IMD 106 to cause one or more phase relationships to approach target phase relationships during delivery of electrical stimulation therapy.

As discussed above, a medical device (e.g., IMD 106 or programmer 104) of system 100 may be configured to determine time-varying measurements of CSDs based on one or more time-varying measurements of LSD received by IMD 106 via electrodes 116, 118. One example way to determine the CSD for respective electrodes is based on voltage differences of adjacent electrodes (e.g., voltage differences between respective time-varying measurements of LFP received from respective adjacent electrodes). For example, IMD 106 may determine a CSD value corresponding to an electrode based on the voltage differences between one or more electrodes adjacent to the electrode corresponding to the measurement of CSD in question. In some examples, the CSD values may be the second spatial difference of voltage difference along the electrodes. Each of the second spatial difference of voltage differences may be a difference between the voltage differences. In other words, in some examples, the CSD values may be the differences between the voltage differences along the lead. In a more specific example, the two CSD values for a four-electrode system would be $(V_1-V_2)-(V_2-V_3)$ and $(V_2-V_3)-(V_3-V_4)$.

For example, the equation to determine the CSD is as follows.

$$\sum_{i=1}^{3}\left(\frac{\partial \sigma_{ii}}{\partial x_i} \cdot \frac{\partial \varphi}{\partial x_i} + \sigma_{ii} \cdot \frac{\partial^2 \varphi}{\partial x_i^2}\right) = -I$$

In the above equation, i represents the index of the dimension (e.g., x, y, or z in Cartesian space), $x_i$ represents one of the dimensions (viz. x, y, or z in Cartesian space), $\sigma_{ii}$ represents the diagonal components of the conductance tensor corresponding to dimension index i, $\varphi$ represents the voltage signal of interest (e.g., voltage at electrodes 116, 118), and I represents the current (e.g., the CSD). If a net current is coming out of neural tissue in the vicinity of the electrode, a current source is registered and I is positive, and if the current is moving into the neural tissue in the vicinity of the electrode, a current sink results, and I is negative.

As an approximation, it is often assumed that the conductivity of the tissue is isotropic and does not change appreciably in the spatial vicinity of the electrodes. This yields a simplified equation as follows.

$$I = -\sigma \sum_{i=1}^{3} \left( \frac{\partial^2 \varphi}{\partial x_i^2} \right)$$

Since the signal of interest, $\varphi(t)$, which is the voltage at one of electrodes 116, 118 and is a time-varying signal, can be differentially sensed between adjacent pairs of equidistant electrodes, the second-order derivative of $\varphi(t)$ can be approximated as follows.

$$\frac{\partial^2 \varphi}{\partial x_i^2} \approx \frac{\Delta \varphi(a, b)}{\Delta x_i(a, b)} - \frac{\Delta \varphi(b, c)}{\Delta x_i(b, c)}$$

In the above equation, a, b, and c are adjacent electrodes, $\Delta x_i(a, b)$ is the distance between electrode a and b, $\Delta x_i(b, c)$ is the distance between electrode b and c, $\Delta \varphi(a, b)$ is the difference in the signal between electrode a and b, and $\Delta \varphi(b, c)$ is the difference in the signal between electrode b and c. Distance between electrodes could be measured from a predetermined point on an edge of one electrode to predetermined point on an edge of an adjacent electrode (such as the closest two points existing between adjacent electrodes.) Alternatively, distance could be the average spacing existing between the points of closest edges of adjacent electrodes. In some examples, the distance may be the distance between center points of the electrodes. In general, distance may be indicative of spacing between electrodes. As described in more detail, to isolate certain frequency markers (e.g., beta band), it may be possible to filter the signal of interest, $\varphi(t)$, or determine a transform (e.g., Fourier transform) of the signal of interest, $\varphi(t)$, and determine the frequency of interest from the transformed signal.

The above equations provide the CSD values in Cartesian coordinates. The following provides the derivation of the CSD equation in cylindrical coordinates system for use with leads that have cylindrical geometries, such as a segmented DBS lead.

As noted above, the equation for the CSD on an electrode is:

$$\sum_{i=1}^{3} \left( \frac{\partial \sigma_{ii}}{\partial x_i} \cdot \frac{\partial \varphi}{\partial x_i} + \sigma_{ii} \cdot \frac{\partial^2 \varphi}{\partial x_i^2} \right) = -I$$

For leads with radially-distributed electrodes, $\nabla \cdot (\sigma \nabla \varphi) = -I$ can be expanded in terms of cylindrical coordinates.

Assuming the conductivity matrix is expressed in cylindrical coordinates, the result may be:

$$\sigma = \begin{pmatrix} \sigma_{rr} & 0 & 0 \\ 0 & \sigma_{\theta\theta} & 0 \\ 0 & 0 & \sigma_{zz} \end{pmatrix}$$

Note that the gradient in this coordinate system is $$\nabla = \left\{ \frac{\partial}{\partial r}, \frac{1}{r} \frac{\partial}{\partial \theta}, \frac{\partial}{\partial z} \right\},$$

and so $$-I = \nabla \cdot \left\{ \sigma_{rr} \frac{\partial \varphi}{\partial r}, \frac{\sigma_{\theta\theta}}{r} \frac{\partial \varphi}{\partial \theta}, \sigma_{zz} \frac{\partial \varphi}{\partial z} \right\}$$

Which can be written in terms of the cylindrical coordinate basis vectors: $\hat{e}_r, \hat{e}_\theta, \hat{e}_z$ $$-I = \left( \hat{e}_r \frac{\partial}{\partial r} + \hat{e}_\theta \frac{1}{r} \frac{\partial}{\partial \theta} + \hat{e}_z \frac{\partial}{\partial z} \right) \cdot \left( \sigma_{rr} \frac{\partial \varphi}{\partial r} \hat{e}_r + \frac{\sigma_{\theta\theta}}{r} \frac{\partial \varphi}{\partial \theta} \hat{e}_\theta + \sigma_{zz} \frac{\partial \varphi}{\partial z} \hat{e}_z \right)$$

In the above equations, r is the radius from the center of the lead, and $\theta$ is the angular position around the lead. Expanding and distributing the derivative, the partial derivatives of the basis vectors are nearly all zero except in two cases:

$$\frac{\partial \hat{e}_r}{\partial \theta} = \hat{e}_\theta \frac{\partial \hat{e}_\theta}{\partial \theta} = -\hat{e}_r.$$

Distributing the partial derivatives and applying the product rule:

$$-I = \hat{e}_r \cdot \left( \frac{\partial}{\partial r} \left( \sigma_{rr} \frac{\partial \varphi}{\partial r} \right) \hat{e}_r + \frac{\partial}{\partial r} \left( \frac{\sigma_{\theta\theta}}{r} \frac{\partial \varphi}{\partial \theta} \right) \hat{e}_\theta + \frac{\partial}{\partial r} \left( \sigma_{zz} \frac{\partial \varphi}{\partial z} \right) \hat{e}_z \right) +$$
$$\hat{e}_\theta \frac{1}{r} \cdot \left( \frac{\partial}{\partial \theta} \left( \sigma_{rr} \frac{\partial \varphi}{\partial r} \right) \hat{e}_r + \sigma_{rr} \frac{\partial \varphi}{\partial r} \hat{e}_\theta + \right.$$
$$\frac{\partial}{\partial \theta} \left( \frac{\sigma_{\theta\theta}}{r} \frac{\partial \varphi}{\partial \theta} \right) \hat{e}_\theta - \frac{\sigma_{\theta\theta}}{r} \frac{\partial \varphi}{\partial \theta} \hat{e}_r + \frac{\partial}{\partial \theta} \left( \sigma_{zz} \frac{\partial \varphi}{\partial z} \right) \hat{e}_z \right) +$$
$$\hat{e}_z \cdot \left( \frac{\partial}{\partial z} \left( \sigma_{rr} \frac{\partial \varphi}{\partial r} \right) \hat{e}_r + \frac{\partial}{\partial z} \left( \frac{\sigma_{\theta\theta}}{r} \frac{\partial \varphi}{\partial \theta} \right) \hat{e}_\theta + \frac{\partial}{\partial z} \left( \sigma_{zz} \frac{\partial \varphi}{\partial z} \right) \hat{e}_z \right)$$

Assuming that $\sigma_{ii}$, $\varphi$, and $-I$ are to be expressed in cylindrical coordinates, and since the basis vectors are orthogonal, many terms equal zero when with application of the dot product:

$$-I = \frac{\partial}{\partial r} \left( \sigma_{rr} \frac{\partial \varphi}{\partial r} \right) + \frac{1}{r} \left( \sigma_{rr} \frac{\partial \varphi}{\partial r} + \frac{\partial}{\partial \theta} \left( \frac{\sigma_{\theta\theta}}{r} \frac{\partial \varphi}{\partial \theta} \right) \right) + \frac{\partial}{\partial z} \left( \sigma_{zz} \frac{\partial \varphi}{\partial z} \right)$$

If assumed that the conductivity of the tissue does not change appreciably in the vicinity of the electrode, then $\sigma_{rr}$, $\sigma_{\theta\theta}$, and $\sigma_{zz}$ constant and this can be rewritten:

$$-I = \frac{\sigma_{rr}}{r} \frac{\partial}{\partial r}\left(r \frac{\partial \varphi}{\partial r}\right) + \frac{\sigma_{\theta\theta}}{r^2} \frac{\partial^2 \varphi}{\partial \theta^2} + \sigma_{zz} \frac{\partial^2 \varphi}{\partial z^2}$$

For examples where the radius r is not changing, such as in leads 114A and 114B, the above equation can be further simplified to the following.

$$-I = \frac{\sigma_{\theta\theta}}{r^2} \frac{\partial^2 \varphi}{\partial \theta^2} + \sigma_{zz} \frac{\partial^2 \varphi}{\partial z^2}$$

The above equation could be used for customizing CSD to be measured or estimated using relative or absolute anisotropy of the local tissue impedance to provide individualized or target-specific CSD estimates. Also, if the values of the conductivity tensor are assumed to be all equal (e.g., $\sigma_{ii}=\sigma$), meaning there is an isotropic medium, then the above equation can be further simplified as follows.

$$-I = \sigma\left(\frac{1}{r^2} \frac{\partial^2 \varphi}{\partial \theta^2} + \frac{\partial^2 \varphi}{\partial z^2}\right)$$

In the above equations, for a fixed, regular angular and vertical spacing of a segmented lead, $\partial\theta=\Delta\theta$ and $\partial z=\Delta z$. For example, $\Delta\theta$ represents the horizontal distance (e.g., angular distance) between two horizontally neighboring electrodes, and $\Delta z$ represents a vertical distance between two vertically neighboring electrodes. For differential recordings $\Delta V_{i,i+1}$, where i is the reference (anode) and i+1 is the cathode, differences between adjacent bipolar recordings $\Delta V_{i+1,i+2} - \Delta V_{i,i+1}$ can be used to approximate a second derivative as follows.

$$\partial\varphi \cong \Delta V_{i,i+1}(t)$$

$$\partial^2\varphi \cong \Delta V_{i+1,i+2}(t) - \Delta V_{i,i+1}(t)$$

For example, IMD 106 may be configured to determine bipolar measurements of the voltages at electrodes 116, 118. A bipolar measurement means that IMD 106 determines a voltage across pairs of electrodes rather than with respect to ground. The bipolar measurement is represented by $\Delta V_{i,i+i}$, where i is the reference (anode) and i+1 is the cathode. The bipolar measurement represents a first derivative, and the difference between two simultaneously recorded adjacent bipolar pairs is an estimate of the second derivative. For example, $\Delta V_{i+1,i+2}(t) - V_{i,i+1}(t)$ is an estimate of the second derivative, and can be rewritten as follows: $(V_{i+1} - V_{i+2}) - (V_i - V_{i+1})$. This equation can be used as the second derivative when determining the CSD for the electrode i. Accordingly, a minimum of two adjacent pairs of electrodes of electrodes 116, 118 may be needed to determine whether the electrode is proximate to an oscillatory signal source (e.g., an oscillatory signal source that is sinking current or an oscillatory signal source that is sourcing current).

Based on the above, the equation for the CSD value can be written as follows.

$$I = -\left(\frac{\sigma_{\theta\theta}}{r^2} \frac{\Delta V_{i,i+1}(t) - \Delta V_{i-1,i}(t)}{(\Delta\theta)^2} + \sigma_{zz} \frac{\Delta V_{j,j+1}(t) - \Delta V_{j-1,j}(t)}{(\Delta z)^2}\right)$$
$$= -(\sigma_{\theta\theta} A_i(t) + \sigma_{zz} Z_j(t))$$

The above equation can be simplified for the isotropic case as follows.

$$I_i(t) = -\sigma[A_i(t) + Z_i(t)], \text{ where}$$

$$A_i(t) = \left(\frac{1}{r^2} \frac{\Delta V_{i,i+1}(t) - \Delta V_{i-1,i}(t)}{(\Delta\theta)^2}\right)$$

$$Z_i(t) = \left(\frac{\Delta V_{j,j+1}(t) - \Delta V_{j-1,j}(t)}{(\Delta z)^2}\right)$$

In the above equation, the time-varying CSD value (e.g., $I_i(t)$) is computed by separating the measurements of the horizontal components and the vertical components. For instance, $A_i(t)$ is the measurement of the horizontal component of the CSD, and $Z_i(t)$ is the measurement of the vertical component of the CSD. Note that for greatest accuracy, $A_i(t)$ and $Z_i(t)$ are typically simultaneously measured. In the above equation, there is only one value for the tissue impedance anisotropy (e.g., $\sigma$). However, in some examples, the conductivity tensor can be empirically determined, such that the value for the tissue impedance anisotropies could be separated out (e.g., there could be a separate value for $\sigma_{11}$, $\sigma_{22}$, and $\sigma_{33}$). Further, these could be relative or normalized values, as often, the practical application may only require relative CSD values.

Another computation simplification that can be made for contacts with equal vertical and horizontal spacing h is that the denominators $\Delta\theta^2$ and $\Delta z^2$ of can be replaced with the spacing h, eliminating the squaring step, since there is interest in looking at relative magnitudes of the CSD across electrodes.

As described above, IMD 106 may be configured to determine, for one or more electrodes of the plurality of electrodes 116, 118, respective time-varying measurements of CSDs. To perform such operations, IMD 106 may be configured to determine, for one or more electrodes of the plurality of electrodes 116, 118, respective first time-varying measurements (e.g., $A_i(t)$) based on second-order voltage differences between two electrodes that horizontally neighbor each electrode (e.g., $\Delta V_{i,i+1}(t) - V_{i-1,i}(t)$) and a horizontal distance between the two horizontally neighboring electrodes (e.g., $\Delta\theta$). IMD 106 may also be configured to determine, for one or more electrodes of the plurality of electrodes 116, 118, respective second time-varying measurements (e.g., $Z_1(t)$) based on second-order voltage differences between two electrodes that vertically neighbor each electrode (e.g., $\Delta V_{j,j+1}(t) - \Delta V_{j-1,j}(t)$) and a vertical distance between the two vertically neighboring electrodes (e.g., $\Delta z$). Distances between two adjacent electrodes may be measured in various ways, as discussed above. IMD 106 may determine respective time-varying measurements of the CSDs based on the respective first time-varying measurements and the second time-varying measurements (e.g., $I_i(t) = -\sigma[A_i(t) + Z_i(t)]$).

In some examples, to determine the first time-varying measurement (e.g., $A_i(t)$), IMD 106 may scale $$\frac{\Delta V_{i,i+1}(t) - \Delta V_{i-1,i}(t)}{(\Delta\theta)^2}$$

by a radius of a lead that includes the respective electrodes. The radius of the lead is r, and scaling may include multiplying $$\frac{\Delta V_{i,i+1}(t) - \Delta V_{i-1,i}(t)}{(\Delta\theta)^2}$$

by 1/r. Also, in some examples, IMD 106 may scale at least one of first time-varying measurement (e.g., $A_i(t)$) or the second time-varying measurement (e.g., $Z_i(t)$) based on an anisotropy of local tissue impedance of the two horizontally neighboring electrodes or the two vertically neighboring electrodes. In the above example, σ represents the isotropy of local tissue impedance and may be assumed to be the same for the horizontally neighboring electrodes and the vertically neighboring electrodes, alternatively, as shown earlier, anatomical variation or electrode characteristics may result in tissue impedance that may be different for the horizontally neighboring electrodes and the vertically neighboring electrodes.

In one or more examples, IMD 106 separately determines the time-varying measurement for the horizontal component (e.g., $A_i(t)$) and the time-varying measurement for the vertical component (e.g., $Z_i(t)$). For example, $A_i(t)$ is based on the horizontal distance between electrodes (e.g., Δθ), and $Z_i(t)$ is based on the vertical distance between electrodes (e.g., Δz). By separating the horizontal and vertical components (e.g., determining the horizontal and vertical components based on horizontal and vertical distances, respectively), the time-varying measurement of the CSD may be more accurate as compared to other techniques that do not separate out the horizontal and vertical components, and only rely on voltage differences between neighboring electrodes.

In some examples, IMD 106 may perform filtering to isolate time-domain representations of a biomarker signal of interest (e.g., matched-filter based, wavelet, or other signal processing techniques). As one example, a band pass filter from 15 to 30 Hz could be used to isolate beta oscillations, which are a putative biomarker for akinetic symptoms of Parkinson's disease.

It should be understood that there may be various signal processing techniques that may be applied to isolate a particular band of interest. As one example, IMD 106 may determine the second-derivative of the voltage measurements (e.g., $\Delta V_{i,i+1}(t) - \Delta V_{i-1,i}(t)$ and $\Delta V_{j,j+1}(t) - \Delta V_{j-1,j}(t)$. IMD 106 may then determine $A_i(t)$ and $Z_i(t)$, and then filter $A_i(t)$ and $Z_i(t)$ for the biomarker signal of interest (e.g., filter to 15 Hz to 30 Hz). As another example, IMD 106 may first filter the voltage measurements, and then determine the second derivative of the voltage measurements. Based on the second derivative of the voltage measurements, generated from the filtered voltage measurements, IMD 106 may determine $A_i(t)$ and $Z_i(t)$. Although voltage measurements are described, the example techniques may be extended to other types of electrical signal levels as well (e.g., current measurements).

In the above examples, the time-domain filtering is utilized (e.g., bandpass filter). However, the techniques are not so limited. For example, rather than performing operations in the time-domain, IMD 106 may perform operations in the frequency-domain. For instance, IMD 106 may apply a Fourier transform (e.g., fast Fourier transform (FFT)) to the electrical signal levels (e.g., voltage measurements) to determine the amplitude of frequency components in the range of 15 Hz to 30 Hz. For the frequency components in the range of 15 Hz to 30 Hz, IMD 106 may determine the values of the horizontal component and the vertical component; however, these measurements would be in the frequency domain instead of the time-domain. For instance, in addition to or instead of determining $A_i(t)$ and $Z_i(t)$, IMD 106 may determine the $A_i(f)$ and $Z_i(f)$ as frequency-varying values. In other words, $A_i(f)$ and $Z_i(f)$ are the FFT of $A_i(t)$ and $Z_i(t)$, respectively. There may be various instances in the processing algorithm where a time-domain filter or a transform from the time-domain to the frequency-domain can occur, and the example techniques are applicable to the different instances of where filtering or transforming occurs.

In some examples, IMD 106 may be configured to output the values of the computed time-varying CSD values (e.g., $I_i(t)$) to programmer 104, and programmer 104 may display information that assists with visualizing the CSD across electrodes. For example, programmer 104 may display a graphical time-varying signal representing the CSD for the electrodes. The visualization could be mapped to the electrode for a view that does not require imaging or lead targeting with orientation markers for the oscillatory signal source. In some examples, the visualization could incorporate electrode mapping with respect to local representations, imaging, or atlas segmentations of the tissue surrounding leads 114A and 114B. For example, the visualization would show the electrodes of electrodes 116, 118, surrounding tissue, and the time-varying CSD values.

In some examples, the CSD values may be mapped to the center or shared electrode of a pair of simultaneous bipolar recordings for 1-D arrays or quadruplet of bipolar recordings for 2-D arrays (e.g., cylindrical or paddle arrays). For example, the CSD values may be slightly different at different points on an electrode, and in some examples, the CSD values may be considered as the CSD value at the center of the electrode. As another example, in determining the bipolar voltage measurements for determining the CSD values, it may be possible to couple two or more electrodes together so that the impedance for the electrodes is the same. In such examples, the CSD values may be considered to be a center point of the electrodes that are coupled together (e.g., the centroid of the coupled electrodes). In some cases, if measuring between a ring electrode and a segmented electrode, there may be impedance mismatch and therefore improper measurements.

In some examples, it may be possible to couple all segmented electrodes at the same axial level so that the electrodes coupled together are equivalent to a ring electrode. For example, a switch may be used to short the segment electrodes in the same axial level together (e.g., ganging segmented electrodes), measure signals between rings (e.g., between a true ring and the ring formed by the ganged electrodes), and using these signals to select a particular row. The electrode segments may then be "unganged," for instance, by the switch un-shorting the segment electrodes. In some examples, CSD values may be measured between the unganged electrodes.

In some examples, IMD 106 may gang the electrodes in a row and use the techniques described in this disclosure to pick one of the middle rows of segmented electrodes with the ganged electrodes. IMD 106 may un-gang the electrodes, and re-measure using the techniques described in this disclosure, and select one or more segmented electrodes within the selected row to use for therapy delivery. Ganging and un-ganging electrodes is one example and should not be considered limiting. In some examples, the ganged electrodes may be used to deliver therapy with an actual ring electrode.

As described, the CSD is a time-varying value. Displaying or visualizing time-varying values may be complicated and possibly difficult for the clinician or patient to comprehend. Providing an instantaneous value for the CSD may not be sufficient for the clinician or patient to understand which electrodes 116, 118 are proximate to the oscillatory signal source because the instantaneous value of the CSD is a snap-shot value for that instant and does not provide sufficient information about how the CSD values vary over time.

Therefore, in one or more examples, IMD 106 may be configured to aggregate the time-varying values of the CSD. There may be various ways in which IMD 106 may aggregate the time-varying values of the CSD. As one example, IMD 106 may average relative CSD amplitude across electrodes, based on magnitude in the frequency domain for frequencies of interest, or on a phase/amplitude-based ranking.

There may be certain benefits with presenting the aggregated time-varying values of the CSD with normalized values, rather than just based on ranking or absolute values. For example, raw aggregated CSD values (e.g., average level values determined from RMS) may result in scales that make it difficult to distinguish important differences between electrodes and ranking may over accentuate differences between electrodes with very similar CSD values. Accordingly, there may be benefits to normalizing the CSD values such that electrodes with similar high or low values can be seen as such. For example, two adjacent electrodes may be nearly equidistant from a very strong signal source, with minute differences in CSD between the two, due largely to noise, while the next closest electrode may have a much smaller CSD. Ranking would assign incremental differences between the three, which may obscure the fact that two are nearly the same. However, an absolute scale may not be so informative where relative differences are desired. So, normalization, would preserve the relative comparisons, while making particularly high or low CSD electrodes stand out from the average.

In some examples, IMD 106 may determine phase/amplitude mapping. In phase/amplitude mapping, IMD 106 may determine a root-mean-square (RMS) value, where the RMS value is representative of the average level values of the CSDs for one or more of electrodes 116, 118. In addition, IMD 106 may determine the phase-magnitude representations for each of electrodes 116, 118. The phase-magnitude representation may be indicative of respective amplitudes of frequency components of the respective time-varying measurements of the CSDs at different phases.

For instance, the average level values (e.g., based on RMS or some of other example techniques) may provide a value that represents the time-varying CSD values. However, in average level values, information about the phase of the time-varying CSD values may be lost. Phase information may be useful because the phase information differentiates between tissue regions acting as oscillatory signal sources (e.g., outputting current) or as sinks (e.g., receiving current). For example, based on a differential phase measurement (e.g., phase of signals at a first electrode relative to some baseline phase), it may be possible to determine that tissue regions around two different electrodes have signals with phases that are 180-degree different, which means that one tissue region is acting as the signal source and another is acting as the signal sink. By using a circular map for phase information and mapping opacity to average level values may yield strong contrast between out-of-phase signal generators (e.g., oscillatory signal sources that are sources and oscillatory signal sources that are sinks).

The above example techniques of generating visualization information (e.g., graphical information) is one example of information that IMD 106 may generate and then cause programmer 104 to display. However, the techniques described in this disclosure are not so limited. In some examples, IMD 106 may not provide any graphical visualization information. Rather, based on the phase-magnitude information, IMD 106 may generate data that lists the average level value for the CSD and generate data indicating whether an oscillatory signal source is a current source or a current sink. As another example, IMD 106 may determine which electrodes 116, 118 are proximate, distal, or in between proximate and distal electrodes to the oscillatory signal source (e.g., based on the average level values of the CSD values and the phase-magnitude representation), and generate data indicating which electrodes 116, 118 are proximate (e.g., "closer to"), distal (e.g., "farther away from"), or in between proximate and distal electrodes to the oscillatory signal source. In one or more examples, electrodes 116, 118 that are proximate may be electrodes that are closer to the oscillation source or sink, and electrodes 116, 118 that are distal may be electrodes that are farther away from the oscillation source or sink.

In some examples, IMD 106 may automatically generate the above example information. Further, in some examples, IMD 106 may be configured to change stimulation setting on electrodes in response to generating the above example information (e.g., electrodes that are proximate, distal, or in between and whether tissue near the electrodes is acting is a signal source or sink). The changes may be in an adaptive manner to target changes in the tissue acting like signal sources or sinks.

As described above, IMD 106 may be configured to aggregate the respective time-varying measurements of the CSDs to generate respective average level values for one or more electrodes of the plurality of electrodes 116, 118 (e.g., including for each electrode of electrodes 116, 118). One example way in which to generate the respective average level values is based on an RMS calculation. As described above, $A_i(t)$ represents a first time-varying measurement between two electrodes that horizontally neighbor each electrode and a horizontal distance between the two horizontally neighboring electrodes, and $Z_i(t)$ represents a second time-varying measurement between two electrodes that vertically neighbor each electrode and a vertical distance between the two vertically neighboring electrodes. $A_i(t)$ may be considered as a horizontal component (e.g., angular for ring electrodes and across for paddle electrodes), and $Z_i(t)$ may be considered as a longitudinal component.

The RMS value of the CSD for an electrode may be equal to:

$$CSD_i^{RMS} = \sigma \sqrt{\frac{1}{N} \sum_{j=1}^{N} |A_i(j) + Z_i(j)|^2}$$

In the above equation, i is the electrode of interest, and N is the number of data points in a temporal window of CSD values that are determined. In this way, IMD 106 may aggregate the time-varying measurements of CSDs for each electrode into a single value for a that electrode. Instead of or in addition to using the voltage amplitude, the power or energy may be utilized. IMD 106 may use the RMS CSD value for purposes of comparison or ranking to determine which electrodes 116, 118 are proximate to the oscillatory signal source. In some examples, the RMS CSD value may be associated with a color to provide a visual indication of the RMS.

In some examples, weighting may be applied to scale the $A_i(j)$ and $Z_i(j)$ samples. For example, more recently acquired $A_i(j)$ and $Z_i(j)$ samples may be weighted more heavily as compared to $A_i(j)$ and $Z_i(j)$ samples acquired less recently. As another example, $A_i(j)$ and $Z_i(j)$ samples that occurred closer in time to an event of interest may be weighted more heavily as compared to $A_i(j)$ and $Z_i(j)$ samples that occurred further away in time from the event of interest.

However, the RMS CSD values (or more generally, the aggregated time-varying measurements of the CSDs) may only provide information of relative amplitudes of the time-varying measurements of the CSDs. Phase information, which might be useful for discriminating between different physiologically relevant sources, may be lost. To address this, IMD 106 may be configured to determine a phase-magnitude representation of the time-varying measurements of the CSDs.

In some examples, it may be beneficial to determine a phase corresponding to each time-varying measurement of CSD corresponding to electrodes 116, 118) so that IMD 106 may control the phase corresponding to each time-varying measurement of CSD in order to achieve a therapy outcome. For example, it may be the case that the respective phases of one or more physiological biomarker signals of brain 120 may have an effect on one or more patient conditions such as chronic pain, tremor, Parkinson's disease, other movement disorders, epilepsy, urinary or fecal incontinence, sexual dysfunction, obesity, or gastroparesis.

In some examples, phase relationships between tissue regions in brain 120 seem to play a role in exaggerated pathological synchronization leading to motor symptoms such as involuntary tremors caused by Parkinson's disease. For example, a phase relationship between the subthalamic nucleus (STN) which represents a target area for stimulation and the cortex is important when delivering DBS therapy to treat one or more patient conditions such as Parkinson's disease. Certain phase relationships support the transfer of information, while others inhibit information transfer.

When patient 105 has Parkinson's disease, for example, the STN and the cortex may be locked in a specific phase relationship. IMD 106 may detect this phase difference and deliver stimulation to brain 120 in order to adjust the phase relationship between the STN and the cortex in order to change a level of communication between the STN and the cortex such that one or more symptoms are improved (e.g., a severity of involuntary tremors is decreased). Additionally, or alternatively, IMD 106 may determine a phase relationship between the STN and the Globus pallidus (GP). Based on the phase relationship between the STN and the GP, IMD 106 may deliver therapy in order to change the phase relationship between the STN and the GP in order to change a level of communication between the STN and the GP such that one or more symptoms are improved (e.g., a severity of involuntary tremors is decreased). Phase relationships between brain regions may determine an amount of neural communication which occurs between the regions. These phase relationships may be disrupted in disorders such as Parkinson's Disease or epilepsy as compared with phase relationships between similar brain regions of Patient's which do not have Parkinson's disease or epilepsy. Tracking phase relationships between brain regions may allow IMD 106 to determine therapy such that a beneficial level of neural communication occurs between the brain regions, thus decreasing a severity of one or more symptoms of a patient condition.

As discussed above, IMD 106 may deliver one or more electrical signals to the STN, making the STN a "target region" of brain 120. IMD 106 may track one or more phase relationships between sub-regions within the STN. For example, each electrode of electrodes 116, 118 may be proximate to a respective tissue region of a set of tissue region, where each tissue region is at least partially within the STN, however this is not required. The tissue region proximate to each electrode of electrodes 116, 118 may be located in regions of the brain other than the STN. Differences in the phase between subregions of the STN have played an important role in therapy stimulation approaches such as coordinated reset, which may improve one or more symptoms associated with Parkinson's disease. Here, the phase of an underlying oscillation may be detected in different spatial regions of the STN. For example, IMD 106 may detect a phase of one or more physiological signals within a tissue region corresponding to each electrode of electrodes 116, 118. One approach entrains different tissue regions of the STN at different phases from each other by applying stimulation differentially across electrodes on a lead, such as lead 114A and/or lead 114B. By detecting respective phases of the tissue region corresponding to each electrode of electrodes 116, 118, stimulation may be delivered more efficiently and effectively as compared with systems which do not monitor phase relationships between sub-regions of the STN. For example, IMD 106 may determine if a first sub-region of the STN corresponding to a first electrode is becoming too synchronized with a second sub-region of the STN corresponding to a second electrode.

In some examples, phase differences between hemispheres of brain 120 may be important in freezing of gate in Parkinson's disease. In some examples, lead 114A is implanted in a first hemisphere of brain 120 and lead 114B is implanted in a second hemisphere of brain 120. This means that IMD 106 may control a phase relationship between the first hemisphere and the second hemisphere by delivering stimulation via leads 114. Monitoring how stimulation is affecting the synchrony between hemispheres may help IMD 106 to determine stimulation.

Interactions or lack thereof between a first tissue region and a second tissue region of brain 120 may depend on whether a phase relationship between the first tissue region and the second tissue represents a synchronous phase relationship or a non-synchronous phase relationship.

A synchronous phase relationship between biomarker signals of a first tissue region and biomarker signals of a second tissue region may cause a level of neural "communication" to occur between the first tissue region and the second tissue region. That is, when a synchronous phase relationship exists between biomarker signals of a first tissue region and biomarker signals of a second tissue region, stimulation of the first tissue region may cause the second tissue region to be stimulated and stimulation of the second tissue region may cause the first tissue region to be stimulated. In this way, when IMD 106 controls the phase relationship between the first tissue region and the second tissue region to be synchronous, IMD 106 may connect the first tissue region and the second tissue region such that activity in one region affects activity in the other region.

A non-synchronous phase relationship between biomarker signals of a first tissue region and biomarker signals of a second tissue region may prevent a level of neural "communication" from occurring occur the first tissue region and the second tissue region. That is, when a non-synchronous phase relationship exists between biomarker signals of a first tissue region and biomarker signals of a second tissue region, stimulation of the first tissue region may inhibit stimulation of the second tissue region and stimulation of the second tissue region may inhibit stimulation of the first tissue region. In this way, when IMD 106 controls the phase relationship between the first tissue region and the second tissue region to be non-synchronous, IMD 106 may prevent the first tissue region and the second tissue region from connecting such that activity in one region does not affect activity in the other region or prevents activity in the other region.

One way to provide therapy to patient 112 is to control the phase relationships of one or more physiological signals sensed by IMD 106 by controlling electrical simulation delivered by IMD 106. For example, delivering a first electrical signal at a first phase to a first tissue region of brain 120 may cause a phase of biomarker signals within a first tissue region of brain 120 to approach the first phase. Additionally, or alternatively, delivering a second electrical signal at a second phase to a second tissue region of brain 120 may cause a phase of biomarker signals within a second tissue region of brain 120 to approach the second phase. This means that IMD 106 may induce a synchronous phase relationship between the first tissue region and the second tissue region by controlling the first phase of the first electrical signal and the second phase of the second electrical signal to be synchronous (e.g., the first phase and the second phase are substantially the same). Alternatively, IMD 106 may induce a non-synchronous phase relationship between the first tissue region and the second tissue region by controlling the first phase of the first electrical signal and the second phase of the second electrical signal to be non-synchronous (e.g., the first phase and the second phase are not the same). IMD 106 may control an amount of difference between the first phase and the second phase.

In some examples, the phase of biomarker signals within a tissue region of the brain 120 may change, or "drift," over a period of time following a stimulation of the tissue region. For example, IMD 106 may stimulate the tissue region in order to cause the biomarker signals to approach a first phase, and the first phase may drift from the first phase to a second phase over a period of time following the stimulation of the tissue region. As discussed above, it may be beneficial to maintain the phase of the first region at the first phase in order allow communication or inhibit communication between the tissue region and one or more other tissue regions. As such, the IMD 106 may execute a phase measurement in order to determine whether the phase has drifted from the first phase and stimulate the tissue region in order to restore the phase of the tissue region to the first phase if IMD 106 determines that the phase of the first tissue region deviates from the first phase.

IMD 106 may, in some cases, determine a phase difference between each pair of time-varying measurements of CSD in the plurality of time-varying measurements of CSD corresponding to electrodes 116, 118 in order to determine a phase relationship corresponding to each pair of tissue regions of one or more respective pairs of tissue regions. For example, each electrode of electrodes 116, 118 may correspond to a respective one or more regions of brain 120 and the phase of the time-varying measurement of CSD corresponding to each electrode of the one or more electrodes may represent a phase of physiological signals sensed from the one or more regions corresponding to the respective electrode of electrodes 116, 118. IMD 106 may perform one or more phase relationship measurements in order to determine the phase of each time-varying measurement of CSD of the plurality of time-varying measurements of CSD. By determining the phase of each time-varying measurement of CSD of the plurality of time-varying measurements of CSD, IMD 106 may determine the phase corresponding to one or more sensed biomarker signals within the tissue region proximate to each the electrode corresponding to each of the plurality of time-varying measurements of CSD.

In some examples, processing circuitry (e.g., processing circuitry of IMD 106 and/or processing circuitry of programmer 104) may be configured to initiate a phase relationship measurement corresponding to a target area of patient 112. The target area may represent an area of brain 120 which IMD 106 provides stimulation to and/or senses one or more physiological signals from. In some examples, the processing circuitry may initiate the phase relationship measurement responsive to receiving information indicative of a user instruction to initiate the phase relationship measurement. In some examples, IMD 106 may receive the user instruction to perform the phase relationship measurement from programmer 104 and initiate the phase relationship measurement. In some examples, the processing circuitry may perform a phase relationship measurement according to a phase relationship measurement program stored in a memory of IMD 106. For example, the phase relationship measurement program may include instructions to perform phase relationship measurements hourly, daily, weekly, or at another time interval. The processing circuitry may determine, based on the phase relationship measurement program, whether to initiate the phase relationship measurement.

The processing circuitry may receive, via two or more electrodes of electrodes 116, 118, two or more electrical signals which indicate a phase relationship between two or more tissue regions within the target area of brain 120. Subsequently, IMD 106 may determine the phase relationship between the two or more electrical signals. The phase relationship between the two or more electrical signals may represent a phase relationship between biomarker signals of the two or more tissue regions. In some examples, the two or more electrical signals represent a plurality of time-varying voltage signals, each time-varying voltage signal of the plurality of time-varying voltage signals corresponding to a respective electrode of electrodes 116, 118. Based on the time-varying voltage signals, the processing circuitry may calculate a time-varying measurement of CSD corresponding to each electrode of electrodes 116, 118. The processing circuitry may use one or more techniques described herein in order to determine the time-varying measurements of CSD.

In some examples, the processing circuitry may determine a phase corresponding to each time-varying measurement of CSD of the plurality of time-varying measurements of CSD corresponding to electrodes 116, 118. In some cases, to determine a phase corresponding to a time-varying measurement of CSD, the processing circuitry may determine a phase-magnitude representation of the time-varying measurement of CSD by calculating a Fourier transform of the time-varying measurement of CSD. Determining CSD to determine phase of the time-varying signal is one example. The example techniques are not limited to any specific way in which to determine a phase for the electrical signals from different oscillatory sources in the regions within a target area.

However, there may be various other ways in which to determine the phase corresponding to the time-varying measurement of CSD. For example, IMD 106 may map a signal of interest to each electrode of electrodes 116, 118. Additionally, IMD 106 may isolate a frequency band in the signal of interest by applying wavelets and empirical mode decomposition. IMD 106 may detect the relative phase of the band of interest corresponding to each electrode of electrodes 116, 118 relative to a reference phase. In some examples, the reference phase corresponds to the electrode with the largest amplitude. In some examples, the reference phase corresponds to another signal such as a bipolar recording or an external signal from an external device. In some examples, IMD 106 performs the phase detection in aggregate. In some examples, IMD 106 performs the phase detection instantaneously after a decomposition method (e.g. band-pass filter, wavelet, EMD, or Hilbert transform), or IMD 106 performs the phase detection instantaneously using a real-time measure that computes phase and amplitude of a band (e.g., a real-time phase measure).

Merely as one example, the following describes an example algorithm for determining a phase-magnitude representation. IMD 106 may be configured to determine which electrode of electrodes 116, 118 has the largest average level value of the corresponding time-varying measurement of CSD (e.g., RMS CSD value). For the determined electrode, IMD 106 may perform a Fourier transform on its time-varying measurement of CSD and determine the largest frequency component of the time-varying measurement of the CSD. For instance, IMD 106 may determine that a particular frequency component for the time-varying measurement of the CSD has the largest Fourier transform coefficient (FTC). The particular frequency component is referred to as $w_0$.

For one or more of electrodes 116, 118, IMD 106 may determine the FTC at frequency $w_0$. For example, assume that $A_{j,k}$ is the FTC at frequency $w_j$ for electrode k. In this example, $A_{w0,i}$ (e.g., the FTC for frequency $w_0$ for the ith electrode) is equal to $M_i e^{j\emptyset_i}$. In this example, $M_i$ is the magnitude of frequency component with frequency $w_0$, $\emptyset_i$ is the phase of the frequency component with frequency $w_0$, and j is the square-root of –1. The values of $M_i$ and $\emptyset_i$ may be determined from an output of a fast Fourier transform (FFT) for a particular frequency component (e.g., $w_0$). Other example ways in which to determine the values of $M_i$ and $\emptyset_i$ include Laplace transform, Hilbert transform, or real-time phase and amplitude tracking. The value of $A_{w0,i}$ is an example of the phase-magnitude representation. In some examples, the phase-magnitude representation may be further normalized.

For example, IMD 106 may determine for which electrode the FTC at frequency $w_0$ is the largest. For instance, assume that there are six electrodes, and therefore, there are six values of $A_{w0}$ (i.e., $A_{w0,1}$, $A_{w0,2}$, $A_{w0,3}$, $A_{w0,4}$, $A_{w0,5}$, and $A_{w0,6}$). IMD 106 may determine which of these six values is the largest. Assume that FTC for the $k^{th}$ electrode for the frequency component with frequency $w_0$ is the largest, where k is equal to 1-6 in the example where there are six electrodes. Accordingly, $A_{w0,k}$ equals $M_k e^{j\emptyset_k}$. In this example, $\emptyset_k$ is the phase of the frequency component with frequency $w_0$ for the largest FTC of the time-varying CSD values at one or more of the electrodes 116, 118. As noted above, frequency $w_0$ is the largest frequency component of the time-varying CSD values that resulted in the greatest aggregated CSD value (e.g., greatest RMS value).

IMD 106 may subtract all FTC (e.g., $A_{w0,i}$) phase values from $\emptyset_k$ to get the phase normalized FTCs. For example, IMD 106 may determine $A_{w0,i\_norm}$ equals $M_i e^{j(\emptyset_i - \emptyset_k)}$. Normalization may not be necessary in all examples, or other types of normalization may be performed. In general, in the time-varying CSD signals there may not be reference phase that can be identified as 0-degree. Accordingly, a particular phase is selected to be the reference phase. In the above example, $\emptyset_k$ is the reference phase to which all of the other phases (e.g., $\emptyset_i$) are normalized. It may be possible to normalize the phase in some other manner. In some examples, "phase relationships" may refer to normalized FTC values determined based on the respective FTCs of the time-varying measurements of CSD corresponding to electrodes 116, 118.

For example, when electrodes 116 and/or electrodes 118 include a set of six electrodes, $A_{w0,1}$ represents the FTC of the time-varying CSD of a first electrode at the frequency $w_0$, $A_{w0,1}$ represents the FTC of the time-varying CSD measurement of a first electrode at the frequency $w_0$, $A_{w0,2}$ represents the FTC of the time-varying CSD measurement of a second electrode at the frequency $w_0$, $A_{w0,3}$ represents the FTC of the time-varying CSD measurement of a third electrode at the frequency $w_0$, $A_{w0,4}$ represents the FTC of the time-varying CSD measurement of a fourth electrode at the frequency $w_0$, $A_{w0,5}$ represents the FTC of the time-varying CSD measurement of a fifth electrode at the frequency $w_0$, and $A_{w0,6}$ represents the FTC of the time-varying CSD measurement of a sixth electrode at the frequency $w_0$. IMD 106 may determine, for example, that $A_{w0,6}$ is the largest FTC value of the set of FTS values. To determine the normalized FTC for the fifth electrode, in this example, IMD 106 may determine that $A_{w0,5\_norm}$ equals $M_5 e^{j(\emptyset_5 - \emptyset_6)}$. This normalized FTC may represent the phase relationship between the fifth electrode and the sixth electrode. It may be beneficial for IMD 106 to maintain the phase relationship between the fifth electrode and the sixth electrode at a target phase relationship value (e.g., a target normalized FTC value) in order to achieve a therapeutic outcome for patient 112.

In some examples, $A_{w0,i\_norm}$ and $(\emptyset_i - \emptyset_k)$ may be indicative of contributions of tissue surrounding each of the "i" electrodes as being signal sources or signal sinks. For example, from above, for each of electrode there is a normalized phase value (e.g., $\emptyset_i - \emptyset_k$), the differences between the normalized phase values may be indicative of which electrodes are separated by 180-degrees. For example, if the normalized phase value for a first electrode is 20-degrees and for a second electrodes is –160-degrees, then there is 180-degree difference between the first and second electrode. In this example, the first and second electrodes may be proximate to respective tissue that are acting as signal source and signal sink.

In this manner, $A_{w0,i\_norm}$ and $(\emptyset_i - \emptyset_k)$ may be utilized to determine which ones of electrodes 116, 118 are most proximate to the oscillatory signal source, and similarly which ones are not proximate to the oscillatory signal source (e.g., normalized phase difference is not big). $A_{w0,i\_norm}$ and $(\emptyset_i - \emptyset_k)$ may together form the normalized phase-magnitude representation of time-varying measurements of the CSDs. $A_{w0,i\_norm}$ is referred to as normalized magnitude and $(\emptyset_i - \emptyset_k)$ is referred to as normalized phase. The normalized phase will be within the range of 0 to $2\pi$, and the values may be indicative of whether the oscillatory signal source is a current sink or a current source.

In some examples, programmer 104, based on instructions from IMD 106 or based on determination of circuitry of programmer 104, may be configured to provide a visual indication of the phase-magnitude representation. For ease, the following describes programmer 104 performing the operation, but in some examples, IMD 106 may perform the operations and output information to programmer 104 indicative of the results of the operation.

Figure 12:
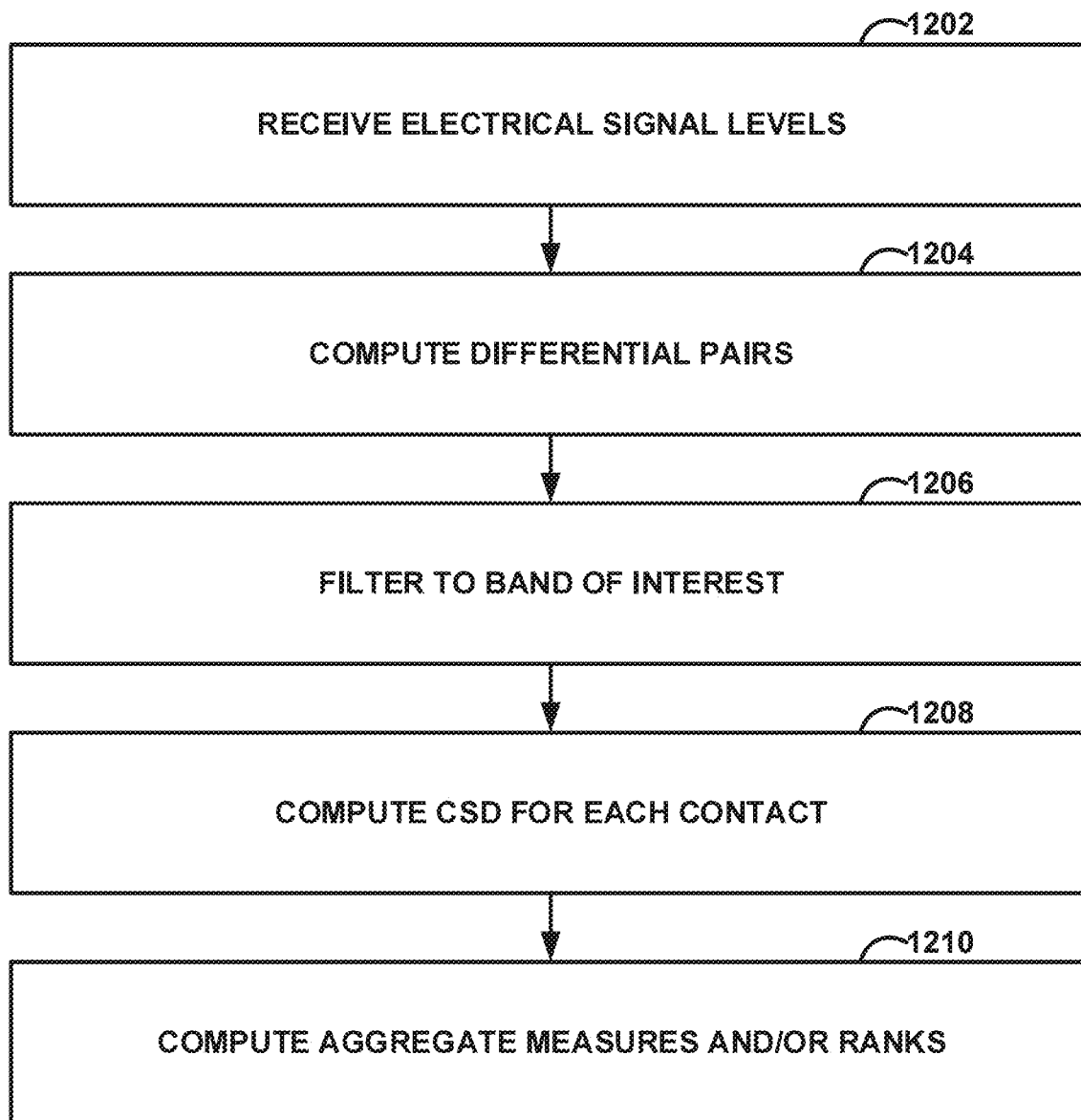
FIG. 12 is a flow diagram illustrating another example operation, in accordance with one or more techniques of this disclosure.

For example, programmer 104 may utilize a circular color map divided into 256 levels such that normalized phase values close to 0 to $2\pi$ show up as red (at the two ends of the color bar) while those close to π show up as cyan (in the middle of the color bar). In this way, a contrast in color is established based on the FTC phase differences (e.g., normalized phase values) between each electrode and the electrode with the largest FTC magnitude at the frequency component having frequency of $w_0$. The utility of this representation is to distinguish physiological sinks and sources from each other using the time-varying measurements of the CSDs based on the phase information. Example of such display is illustrated in FIG. 12 using black-and-white gray-scale rather than color.

For the normalized magnitude, programmer 104 may be configured to map the absolute value of the normalized magnitude to the opacity of the corresponding color of normalized phase values. For instance, programmer 104 may determine the opacity of the color determined for $(Ø_i-Ø_k)$ based on the value of the absolute value of $A_{w0,i\_norm}$. In some examples, programmer 104 may assign 100% opacity to the maximum value of the normalized phase values, and assign 0% opacity (e.g., 100% transparency) to the minimum value of the normalized phase values.

The above describes an example way in which to display the phase-magnitude representation of the time-varying measurements of the CSD values. However, the example techniques are not so limited to the above ways in which to display the phase-magnitude representation. In general, the phase-magnitude representation for an electrode of electrodes 116, 118 may be indicative of the magnitude and phase of a particular frequency component of the time-varying measurement of the CSD for that electrode. The particular frequency component may be a frequency component having the largest transform coefficient within a spectral band of interest in a time-varying measurement of a CSD having a largest average level value. For instance, the particular frequency component is the frequency component having a frequency of $w_0$.

In this way, IMD 106 may configured to determine, for one or more electrodes of the plurality of electrodes 116, 118, respective time-varying measurements of current source densities (CSDs). IMD 106 may aggregate, for one or more electrodes of the plurality of electrodes 116, 118, the respective time-varying measurements of the CSDs to generate respective average level values for one or more electrodes of the plurality of electrodes (e.g., generate respective RMS values from the CDS values). IMD 106 may determine, for one or more electrodes of the plurality of electrodes 116, 118, respective phase-magnitude representations of the time-varying measurements of the CSDs. The respective phase-magnitude representations are indicative of respective magnitudes and phases of a particular frequency component of respective time-varying measurements of the CSDs (e.g., the normalized magnitude ($A_{w0,i\_norm}$) and the normalized phase value ($Ø_i-Ø_k$) but normalization is not necessary in all examples). The particular frequency component is a frequency component having a largest transform coefficient within a spectral band of interest in a time-varying measurement of a CSD having a largest average level value (e.g., the frequency component is the frequency $w_0$).

IMD 106 may generate information indicative of the respective average level values and respective phase-magnitude representations. For example, IMD 106 may output information indicative of the average level values and the phase-magnitude representations, and programmer 104 may provide a visual representation that a clinician can use to determine which electrodes 116, 118 are proximate to the oscillatory signal source, and possibly whether the oscillatory signal source is a current sink or a current source.

In some examples, IMD 106 may execute one or more techniques described herein in order to improve a power efficiency of system 100 as compared with medical device systems which do not deliver stimulation to the brain in order to control one or more relative phase relationships between tissue regions of the brain. For example, IMD 106 may monitor one or more relative phase relationships and identify an "unwanted" phase relationship when it develops. The unwanted phase relationship may represent a phase relationship between tissue regions which causes or exacerbates one or more unwanted symptoms such as involuntary tremors. IMD 106 may deliver one or more electrical signals to brain 120 in order to cause the unwanted phase relationship to approach a "wanted" target phase relationship. The wanted target phase relationship represents a phase relationship controls neural activity between tissue regions such that one or more adverse patient symptoms are attenuated or eliminated. In this way, IMD 106 may conserve power by delivering the electrical signals when unwanted phase relationships are detected, and refrain from delivering the electrical signals when no unwanted phase relationships are detected.

IMD 106 may additionally or alternatively identify a "decay" in a wanted phase relationship. That is, IMD 106 may identify a drift of a relative phase relationship from a wanted phase relationship to an unwanted phase relationship. IMD 106 may deliver one or more electrical signals to brain 120 in order to restore the relative phase relationship to the wanted target phase relationship in response to detecting the decay. Additionally, it may be beneficial for IMD 106 to detect a drift of a relative phase relationship towards a wanted target phase relationship so that IMD 106 can decline to deliver stimulation and thus save power. In any case, IMD 106 may deliver electrical stimulation to brain 120 in order to cause phase relationships to approach phase relationships, and IMD 106 may deliver electrical stimulation to brain 120 when a phase relationship is at or approaching a wanted phase relationship. In this way, monitoring phase relationships may allow IMD 106 to consume power when electrical stimulation is needed to achieve wanted phase relationships and decline to consume power to deliver electrical signals when the electrical signals are not needed to achieve wanted phase relationships.

The above example techniques are described with respect to DBS. However, the example techniques are not so limited. For instance, the example techniques may be used with evoked responses. For example, a stimulation pulse or burst from an electrode on the same or another lead evokes a neural response and the CSD is used, in accordance with one or more examples described in this disclosure, to identify which electrodes are closest or furthest from the tissue with the neural response. The example techniques may be used with DBS, spinal stimulation, and peripheral nerve stimulation scenarios, as a few examples.

Figure 2:
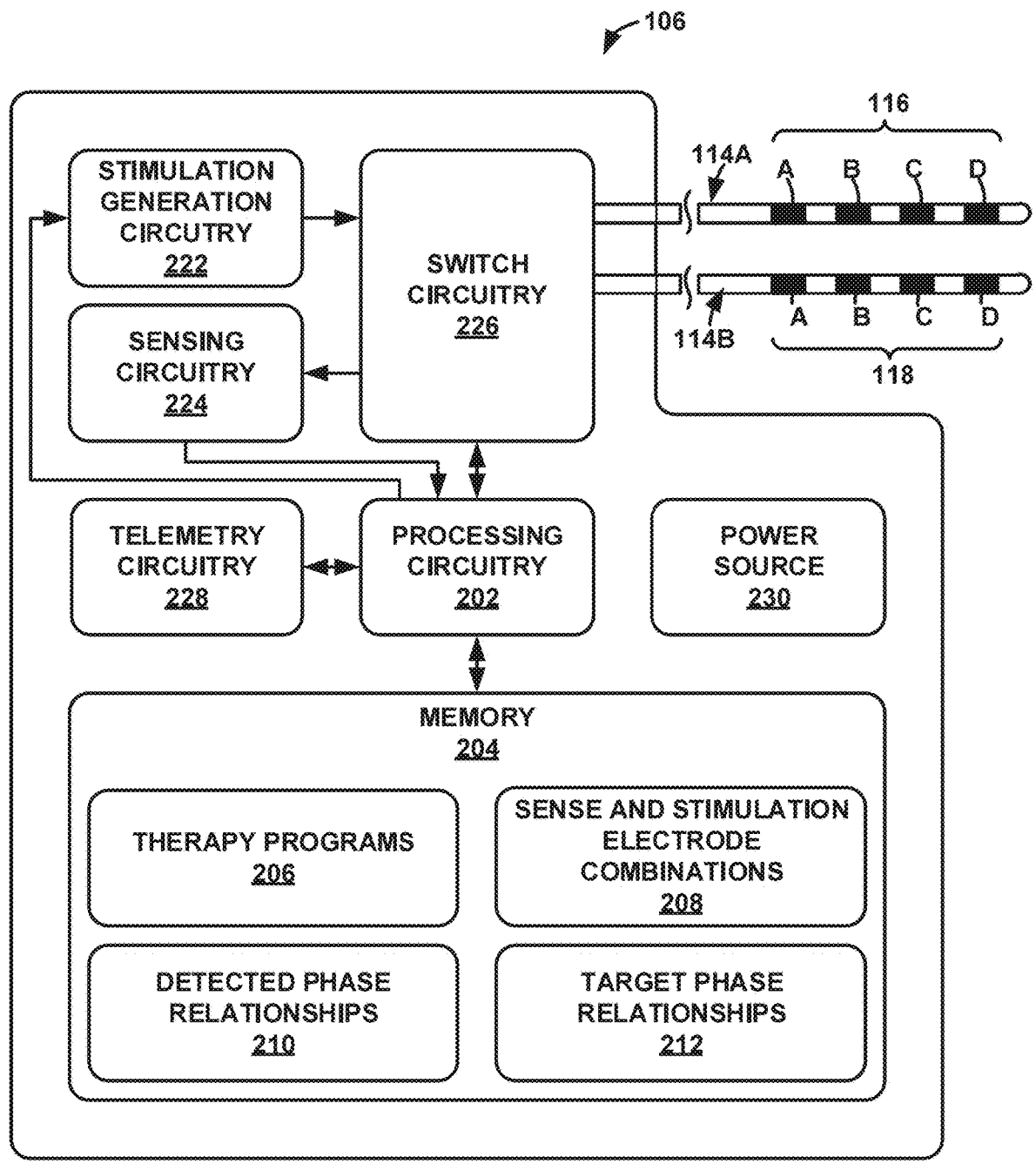
FIG. 2 is a block diagram of the example IMD of FIG. 1 for determining one or more relative phase relationships, in accordance with one or more techniques of this disclosure.

FIG. 2 is a block diagram of the example IMD 106 of FIG. 1 for determining one or more relative phase relationships, in accordance with one or more techniques of this disclosure. In the example shown in FIG. 2, IMD 106 includes processing circuitry 202, stimulation generation circuitry 222, sensing circuitry 224, switch circuitry 226, telemetry circuitry 228, memory 204, and power source 230. Each of these circuits may be or include electrical circuitry configured to perform the functions attributed to each respective circuit. Memory 204 may include any volatile or non-volatile media, such as a random-access memory (RAM), read only memory (ROM), non-volatile RAM (NVRAM), electrically erasable programmable ROM (EEPROM), flash memory, and the like. Memory 204 may store computer-readable instructions that, when executed by processing circuitry 202, cause IMD 106 to perform various functions. Memory 204 may be a storage device or other non-transitory medium.

IMD 106 may be configured to perform one or more phase relationship measurements in order to monitor relative phase relationships between physiological signals measured in regions of the brain 120 of patient 112. For example, IMD 106 receives a time-varying voltage signal from each electrode of the plurality of electrodes 116, 118. Based on the plurality of time-varying voltage signals received from the plurality of electrodes 116, 118. IMD 106 may determine a plurality of time-varying measurements of CSD. The plurality of time-varying measurements of CSD may indicate one or more phase relationships between regions corresponding to each electrode of the plurality of electrodes 116, 118. It may be beneficial to determine the one or more phase relationships so that IMD 106 may determine one or more therapy parameters for electrical stimulation therapy to be delivered to patient 112.

Processing circuitry 202 may include fixed function circuitry and/or programmable processing circuitry. Processing circuitry 202 may include, for example, microprocessors, digital signal processors (DSPs), application specific integrated circuits (ASICs), field programmable gate arrays (FPGAs), equivalent discrete or integrated logic circuitry, or a combination of any of the foregoing devices or circuitry. Accordingly, processing circuitry 202 may include any suitable structure, whether in hardware, software, firmware, or any combination thereof, to perform the functions ascribed herein to IMD 106.

In some examples, memory 204 includes computer-readable instructions that, when executed by processing circuitry 202, cause IMD 106 to perform various functions attributed to IMD 106 herein. Memory 204 may include one or both of a short-term memory or a long-term memory. The memory may include, for example, random access memory (RAM), non-volatile random access memory (NVRAM), dynamic random access memory (DRAM), static random access memory (SRAM), read only memory (ROM), magnetic discs, optical discs, flash memory, or forms of electrically programmable memory (EPROM) or electrically erasable and programmable memory (EEPROM). In some examples, the memory is used to store program instructions for execution by processing circuitry 202.

In the example shown in FIG. 2, memory 204 stores therapy programs 206, sense electrode combinations and associated stimulation electrode combinations 208 (collectively, "combinations 208"), detected phase relationships 210, and target phase relationships 212. In some examples, memory 204 stores therapy programs 206, combinations 208, detected phase relationships 210, and target phase relationships 212 in separate memories within memory 204 or separate areas within memory 204, but this is not required. Each stored therapy program of therapy programs 206 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Combinations 208 include sense electrode combinations and associated stimulation electrode combinations. As described above, in some examples, sense and combinations 208 may include the same subset of electrodes 116, 118, a housing of IMD 106 functioning as an electrode, or may include different subsets or combinations of such electrodes. Thus, memory 204 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processing circuitry 202. In some examples, corresponding sense and stimulation electrode combinations may include some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy.

Detected phase relationships 210 may represent phase relationships determined by processing circuitry 202 based on one or more electrical signals received by processing circuitry 202 via electrodes 116, 118. Target phase relationships 212 may represent phase relationships which are desired in order to achieve one or more therapy outcomes for patient 112. That is, when processing circuitry 202 identifies one or more differences between the detected phase relationships 210 and the target phase relationships 212, processing circuitry 202 may determine that one or more therapy changes are needed to cause the detected phase relationships to approach the target phase relationships.

Stimulation generation circuitry 222, under the control of processing circuitry 202, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 90 to 170 Hertz or such as approximately 90 Hertz.

2. In the case of a voltage controlled system, Voltage Amplitude: between approximately 0.1 volts and approximately 50 volts, such as between approximately 2 volts and approximately 3 volts.

3. In the case of a current controlled system, Current Amplitude: between approximately 1 milliamps to approximately 3.5 milliamps, such as between approximately 1.0 milliamps and approximately 1.75 milliamps.

4. Pulse Width: between approximately 50 microseconds and approximately 500 microseconds, such as between approximately 50 microseconds and approximately 200 microseconds.

Accordingly, in some examples, stimulation generation circuitry 222 generates electrical stimulation signals in accordance with the electrical stimulation parameters noted above. Other ranges of therapy parameter values may also be useful and may depend on the target stimulation site within patient 112. While stimulation pulses are described, stimulation signals may be of any form, such as continuous-time signals (e.g., sine waves) or the like. In some examples, stimulation 22 generates electrical stimulation signals according to one or more therapy parameters determined by processing circuitry 202 responsive to processing circuitry 202 determining one or more differences between detected phase relationships 210 and target phase relationships 212.

In some examples, sensing circuitry 224 may include sensing circuitry for sensing signals. For example, sensing circuitry 224 may receive one or more electrical signals from electrodes 116, 118 via switch circuitry 226. The one or more electrical signals received by sensing circuitry 224 may include, in some cases, a set of time-varying voltage signals, where each time-varying voltage signal of the set of time-varying voltage signals corresponds to a respective electrode of electrodes 116, 118. Sensing circuitry 224 may include circuitry for filtering one or more electrical signals received by sensing circuitry 224, but this is not required. In some examples, sensing circuitry 224 may output one or more signals to processing circuitry 202 based on the one or more electrical signals received by sensing circuitry 224.

In the example shown in FIG. 2, the set of electrodes 116 includes electrodes 116A, 116B, 116C, and 116D, and the set of electrodes 118 includes electrodes 118A, 118B, 118C, and 118D. Processing circuitry 202 also controls switch circuitry 226 to apply the stimulation signals generated by stimulation generation circuitry 222 to selected combinations of electrodes 116, 118. In particular, switch circuitry 226 may couple stimulation signals to selected conductors within leads 114, which, in turn, deliver the stimulation signals across selected electrodes 116, 118. Switch circuitry 226 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generation circuitry 222 is coupled to electrodes 116, 118 via switch circuitry 226 and conductors within leads 114. In some examples, however, IMD 106 does not include switch circuitry 226.

Stimulation generation circuitry 222 may be a single channel or multi-channel stimulation generator. In particular, stimulation generation circuitry 222 may be capable of delivering a single stimulation pulse, multiple stimulation pulses, or a continuous signal at a given time via a single electrode combination or multiple stimulation pulses at a given time via multiple electrode combinations. In some examples, however, stimulation generation circuitry 222 and switch circuitry 226 may be configured to deliver multiple channels on a time-interleaved basis. For example, switch circuitry 226 may serve to time divide the output of stimulation generation circuitry 222 across different electrode combinations at different times to deliver multiple programs or channels of stimulation energy to patient 112. Alternatively, stimulation generation circuitry 222 may include multiple voltage or current sources and sinks that are coupled to respective electrodes to drive the electrodes as cathodes or anodes. In this example, IMD 106 may not require the functionality of switch circuitry 226 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes, e.g., arranged as segments, at different perimeter locations around the perimeter of the lead at each of the locations A, B, C, and D.

As an example, one or both of leads 114 may include radially-segmented DBS arrays (rDBSA) of electrodes. In the rDBSA, as one example, there may be a first ring electrode of electrodes 116 around the perimeter of lead 114A at a first longitudinal location on lead 114A (e.g., location A). Below the first ring electrode, there may be three segmented electrodes of electrodes 116 around the perimeter of lead 114A at a second longitudinal location on lead 114A (e.g., location B). Below the three segmented electrodes, there may be another set of three segmented electrodes of electrodes 116 around the perimeter of lead 114A at a third longitudinal location of lead 114A (e.g., location C). Below the three segmented electrodes, there may be a second ring electrode of electrodes 116 around the perimeter of lead 114A (e.g., location D). Electrodes 118 may be similarly positioned along lead 114B.

The above is one example of the rDBSA array of electrodes, and the example techniques should not be considered limited to such an example. There may be other configurations of electrodes for DBS. Moreover, the example techniques are not limited to DBS, and other electrode configurations are possible.

In one example, the electrodes 116, 118 may be electrically coupled to switch circuitry 226 via respective wires that are straight or coiled within the housing of the lead and run to a connector at the proximate end of the lead. In another example, each of the electrodes 116, 118 of the leads 114 may be electrodes deposited on a thin film. The thin film may include an electrically conductive trace for each electrode that runs the length of the thin film to a proximate end connector. The thin film may then be wrapped (e.g., a helical wrap) around an internal member to form the leads 114. These and other constructions may be used to create a lead with a complex electrode geometry.

Although sensing circuitry 224 is incorporated into a common housing with stimulation generation circuitry 222 and processing circuitry 202 in FIG. 2, in other examples, sensing circuitry 224 may be in a separate housing from IMD 106 and may communicate with processing circuitry 202 via wired or wireless communication techniques. Example neurological brain signals include, but are not limited to, a signal generated from local field potentials (LFPs) within one or more regions of brain 120. EEG and ECoG signals are examples of local field potentials that may be measured within brain 120. LFPs, EEG and ECoG may be different measurements of the same bioelectric signals in the brain. The neurons generate the signals, and if measured at depth, it is LFP, if measured on the cortex, it is ECoG, if on the scalp, it is EEG. In general, the bioelectric signals may be formed by one or more oscillatory signal sources. The set of electrodes 116 and 118 that are most proximate to the oscillatory signal sources are good candidates to use for delivering therapy.

Telemetry circuitry 228 supports wireless communication between IMD 106 and an programmer 104 or another computing device under the control of processing circuitry 202. Processing circuitry 202 of IMD 106 may receive, as updates to programs, values for various stimulation parameters such as magnitude and electrode combination, from programmer 104 via telemetry circuitry 228. The updates to the therapy programs may be stored within therapy programs 206 portion of memory 204. Telemetry circuitry 228 in IMD 106, as well as telemetry modules in other devices and systems described herein, such as programmer 104, may accomplish communication by radiofrequency (RF) communication techniques. In addition, telemetry circuitry 228 may communicate with programmer 104 via proximate inductive interaction of IMD 106 with programmer 104. Accordingly, telemetry circuitry 228 may send information to programmer 104 on a continuous basis, at periodic intervals, or upon request from IMD 106 or programmer 104.

Power source 230 delivers operating power to various components of IMD 106. Power source 230 may include a small rechargeable or non-rechargeable battery and a power generation circuit to produce the operating power. Recharging may be accomplished through proximate inductive interaction between an external charger and an inductive charging coil within IMD 106. In some examples, power requirements may be small enough to allow IMD 106 to utilize patient motion and implement a kinetic energy-scavenging device to trickle charge a rechargeable battery. In other examples, traditional batteries may be used for a limited period of time.

In one example, processing circuitry 202 of IMD 106 senses, via electrodes 116, 118 and sensing circuitry 224, one or more bioelectric signals of brain 120 of patient 112. Further, processing circuitry 202 controls stimulation generation circuitry 222 to deliver, via electrodes 116, 118, electrical stimulation therapy to patient 112 based on the sensed one or more bioelectric signals of brain 120. DBS therapy is defined by one or more therapy programs 206 having one or more parameters stored within memory 204. For example, the one or more parameters include a current amplitude (for a current-controlled system) or a voltage amplitude (for a voltage-controlled system), a pulse rate or frequency, a phase of a sequence of pulses, a pulse width, or a number of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, an off-time, and a phase of the series of electrical pulses. Processing circuitry 202, via electrodes 116, 118, delivers to patient 112 DBS and may adjust one or more parameters defining the electrical stimulation based on corresponding parameters of the sensed one or more bioelectric signals of brain 120. For example, processing circuitry 202 may adjust one or more parameters defining the electrical stimulation in order to cause one or more detected phase relationships to approach one or more target phase relationships.

In some examples, processing circuitry 202 continuously measures the one or more bioelectric signals in real time. In other examples, processing circuitry 202 periodically samples the one or more bioelectric signals according to a predetermined frequency or after a predetermined amount of time. In some examples, processing circuitry 202 and/or sensing circuitry 224 periodically samples the signal at a frequency of approximately 150, 250, 500, or 1000 Hertz, but this is not required. processing circuitry 202 and/or sensing circuitry 224 may sample the signal at any frequency. In some examples, processing circuitry 202 may receive, from one or more electrodes of electrodes 116, 118, a time-varying voltage signal which corresponds to a tissue region proximate to the respective electrode of electrodes 116, 118. For example, processing circuitry 202 may receive a first time-varying voltage signal from electrode 116A, a second time-varying voltage signal from electrode 116B, a third time-varying voltage signal from electrode 116C, and a fourth time-varying voltage signal from electrode 116D, however this is not required. Processing circuitry 202 may receive signals from any one or combination of electrodes 116, 118.

As one example way to determine the CSD value, processing circuitry 202 may cause sensing circuitry 224 to measure the voltage across pairs of electrodes 116, 118, where the voltage across the pairs of electrodes 116, 118 is due to the time-varying signal generated by the oscillatory signal source. For example, the "voltage across" electrodes 116A and 116C represents a difference between the time-varying voltage signal corresponding to electrode 116A and the time-varying voltage signal corresponding to electrode 116C. The result of the measured voltages may be a set of differential voltages. Processing circuitry 202 may then determine the difference between differential voltages of the set of differential voltages to determine a CSD value for one or more of electrodes 116, 118 (expect for possibly the top and bottom electrodes).

For example, processing circuitry 202 may determine, for one or more electrodes of the plurality of electrodes 116 and 118, respective time-varying measurements of CSDs. As one example, processing circuitry 202 may determine, for one or more electrodes of the plurality of electrodes, respective first time-varying measurements based on second-order voltage differences between two electrodes that horizontally neighbor each electrode and a horizontal distance between the two horizontally neighboring electrodes and determine, for one or more electrodes of the plurality of electrodes, respective second time-varying measurements based on second-order voltage differences between two electrodes that vertically neighbor each electrode and a vertical distance between the two vertically neighboring electrodes. Processing circuitry 202 may determine respective time-varying measurements of the CSDs based on the respective first time-varying measurements and the second time-varying measurements.

As one example, processing circuitry 202 may scale the respective first-time varying measurements based on a radius of leads 104A, B that includes the respective electrodes of electrodes 116, 118 (e.g., determine $A_i(t)$ as described above by scaling by a factor of $1/r$). Also, in some examples, processing circuitry 202 may scale at least one of the respective first time-varying measurements or the second time-varying measurements based on an anisotropy of local tissue impedance of the two horizontally neighboring electrodes or the two vertically neighboring electrodes. For instance, processing circuitry 202 may multiply the first and second time-varying measurements by of the CSDs by $\sigma$.

Processing circuitry 202 may be configured to aggregate, for one or more electrodes of the plurality of electrodes 116, 118, the respective time-varying measurements of the CSDs to generate respective average level values for one or more electrodes of the plurality of electrodes. For example, processing circuitry 202 may be configured to determine, for one or more electrodes of the plurality of electrodes 116, 118, respective root-mean-square (RMS) values based on the respective first time-varying measurement and the second time-varying measurement. As described above, processing circuitry 202 may perform the operations of the following equation to generate the average level value as a way to aggregate the respective time-varying measurements of the CSDs.

$$CSD_i^{RMS} = \sigma \sqrt{\frac{1}{N} \sum_{j=1}^{N} |A_i(j) + Z_i(j)|^2}$$

In the above equation, i is the electrode of interest, and N is the number of data points in a temporal window of CSD values that are determined. Techniques other than techniques to calculate RMS values may be used to aggregate time-varying measurements of the CSD values. For example, $A_i(j)$ represents a first time-varying measurement of a difference between the time-varying voltage measurements corresponding to two electrodes that horizontally neighbor an electrode j and a horizontal distance between the two horizontally neighboring electrodes, and $Z_i(j)$ represents a second time-varying measurement of a difference between the time-varying voltage measurement corresponding to the two electrodes that vertically neighbor the electrode j and a vertical distance between the two vertically neighboring electrodes. That is, $A_i(j)$ may be considered as a horizontal component (e.g., angular for ring electrodes and across for paddle electrodes), and $Z_i(j)$ may be considered as a longitudinal component. Processing circuitry 202 may calculate the time-varying measurement of CSD corresponding to one or more electrodes of electrodes 116, 118 based on the above equation, and determine one or more phase relationships based on the calculated time-varying measurements of CSD.

In addition to generating the average level values, processing circuitry 202 may determine for one or more electrodes of the plurality of electrodes 116, 118, respective phase-magnitude representations of the time-varying measurements of the CSDs. The respective phase-magnitude representations are indicative of respective magnitudes and phases of a particular frequency component of respective time-varying measurements of the CSDs, where the particular frequency component is a frequency component having a largest transform coefficient in a time-varying measurement of a CSD having a largest average level value. There may be various ways in which to determine the phase-magnitude representation.

For example, processing circuitry 202 may determine which electrode of electrodes 116, 118 has a highest average level value and determine a largest frequency component in the time-varying measurement of the CSD for the electrode having the highest average level value. For example, assume that electrode X has the highest average level value of the time-varying measurements of the CSDs, and assume that frequency $w_0$ is the largest frequency component in the time-varying measurement CSD at electrode X.

Processing circuitry 202 may determine, for one or more electrodes of the plurality of electrodes 116, 118, respective transform coefficients (e.g., Fourier transform coefficients (FTCs)) at the determined largest frequency component (e.g., $w_0$) in respective time-varying measurements of the CSDs. Processing circuitry 202 may also determine, for one or more electrodes of the plurality of electrodes 116, 118, respective phase values associated with the respective transform coefficients. For example, assume that $A_{w0,i}$ is the FTC for frequency $w_0$ for the ith electrode, and is equal to $M_i e^{j\emptyset_i}$. In this example, $M_i$ is the magnitude of frequency component with frequency $w_0$, $\emptyset_i$ is the phase of the frequency component with frequency $w_0$ (e.g., phase value associated with transform coefficient), and j is the square-root of $-1$.

In this example, processing circuitry 202 may determine respective phase-magnitude representations based on the determined respective transform coefficients and the respective phase values. For example, processing circuitry 202 may utilize the $M_i$ and $\emptyset_i$ values to determine respective phase-magnitude representations for electrode i. As one example, processing circuitry 202 may determine a largest transform coefficient from the respective transform coefficients. For instance, $A_{w0,k}$ represents the largest transform coefficient and is the coefficient of electrode-k. $A_{w0,k}$ equals $M_k e^{j\emptyset_k}$. Processing circuitry 202 may determine a phase value associated with the determined largest transform coefficient (e.g., determine $\emptyset_k$). Processing circuitry 202 may determine a difference between respective phase values associated with respective transform coefficients and the determined phase value associated with the determined largest transform coefficient (e.g., determine $(\emptyset_i - \emptyset_k)$). Processing circuitry 202 may determine respective normalized phase-magnitude representations based on the determined difference and the determined respective transform coefficients (e.g., $A_{w0,i\_norm}$ equals $M_i e^{j(\emptyset_i - \emptyset_k)}$).

In some examples, processing circuitry 202 may be configured to generate information indicative of the respective average level values and respective phase-magnitude representations. As one example, processing circuitry 202 may output color information that represents the different average level values for the electrodes and output color information for the phase and the opacity of the color for the phase is based on the magnitude. As another example, processing circuitry 202 may output average level values and phase-magnitude representations as data values.

In some examples, it may be beneficial for processing circuitry 202 to cause a phase relationship between bioelectric signals of a first tissue region of brain 120 and bioelectric signals of a second tissue region of brain 120 to approach a target phase relationship. For example, when processing circuitry 202 causes a phase relationship between a first tissue region and a second tissue region to approach or reach a synchronous phase relationship, the processing circuitry 202 may cause a level of neural activity (e.g., neural communication) to occur between the first tissue region and the second tissue region. Neural activity or neural communication between the first tissue region and the second tissue region may represent a phenomenon where activity (e.g., "active neurons") in one tissue region may cause activity in the other region. Additionally, synchronous phase relationships may arise when a first tissue region and a second tissue region are in neural communication with a third tissue region, causing the first tissue region and the second tissue region to have a synchronous phase relationship. Synchronous phase relationships also include examples in which two tissue regions have a reciprocal connection, e.g., a first tissue region excites a second tissue region, and the second tissue region either excites or inhibits the first tissue regions. Phase-amplitude coupling (PAC) is a form of a synchronous phase relationship in which input from one tissue region enables or grants faster processing in a second tissue region. This may represent a coupling between amplitude of a faster oscillation in the second tissue region with the amplitude of an oscillation in the first tissue region. Additionally, a synchronous phase relationship may arise when a first tissue region and a second tissue region receive separate inputs that are highly correlated (e.g., a sensory system that is processing the proprioceptive inputs of muscle movements, and the motor system commanding the muscle movements).

Processing circuitry 202 may cause a phase relationship between a first tissue region and a second tissue region to approach or reach a non-synchronous phase relationship. Non-synchronous phase relationship may include phase relationships where electrical signals of a first tissue region and a second tissue region do not have the same phase. In some examples, non-synchronous phase relationships may cause the processing circuitry 202 to prevent a level of neural communication from occurring between the first tissue region and the second tissue region. That is, by preventing neural communication between the first tissue region and the second tissue region, neural activity occurring in one tissue region does not cause neural activity to occur in the other tissue region. It may be the case that neural activity occurs in both of the first tissue region and the second tissue region at the same time when a non-synchronous phase relationship exists between the first tissue region and the second tissue region, however, when a non-synchronous phase relationship exists between the first tissue region and the second tissue region, neural activity in one region does not induce neural activity in the other region. A non-synchronous phase relationship may represent any phase relationship which results in a diminished communication between a first tissue region and a second tissue region.

Processing circuitry 202 may receive one or more target phase relationships 212 from programmer 104. In some examples, the target phase relationships 212 may be selected by a clinician via a user interface of programmer 104 in order to achieve one or more therapy outcomes. By causing the phase relationships between tissue regions of brain 120, processing circuitry 202 may achieve the one or more therapy outcomes intended by the clinician by preventing or allowing neural communication between respective groups of two or more tissue regions. For example, phase-specific stimulation of the ventral intermediate nucleus of the thalamus of brain 120, causing tissue regions of brain 120 to approach one or more target phase relationships, can reduce tremors which may arise from the phase desynchronization of oscillators in the motor system of the patient. Preventing neural communication between two or more tissue regions and/or allowing neural communication between two or more tissue regions may cause a frequency and/or a severity of involuntary tremors in patient 105 to decrease as compared with systems which do not control phase relationships between tissue regions of the brain. In other words, controlling one or more regional phase synchronizations and/or one or more regional phase desynchronizations may decrease a likelihood of the patient 105 experiencing a seizure or otherwise improve one or more patient conditions associated with epilepsy. In the case of Parkinson's disease, a coordinated reset of pathological oscillations may lead to the development of spatially distributed patterned stimulation to evoke long-lasting therapeutic improvement. Consequently, one or more techniques to estimate phase relationships in local and regional networks and utilize those phase relationships to deliver phase-targeted stimulation to specific regions of the brain may be beneficial for improving one or more patient conditions.

A coordinated reset may represent a disruption of one or more phase relationships, such that the signal phases become more distributed, or less phase-locked. For example, a coordinated reset may cause a difference between a first phase and a second phase to increase (e.g., become more different). A set of synchronized oscillators may result in decreased signal amplitudes in a target frequency range, which decreases a probability that IMD 106 can detect reliable phase relationships between signals. As such, it may be beneficial to perform one or more coordinated resets to decrease a synchrony of one or more pairs of oscillators.

Processing circuitry 202 may be configured to determine one or more detected phase relationships 210 based on determining one or more normalized phase-magnitude representations (e.g., $A_{w0,i\_norm}$) of time-varying measurements of the CSDs determined by processing circuitry 202 based on the signals received from electrodes 116, 118. The normalized phase-magnitude representations determined by processing circuitry 202 may indicate one or more phase relationships of target tissue regions within brain 120. For example, the normalized phase-magnitude representation $A_{w0,i\_norm} = M_i e^{j(\varnothing_i - \varnothing_k)}$ indicates a phase relationship $\varnothing_i - \varnothing_k$ which represents a phase relationship between a first electrode i and a second electrode k. Processing circuitry 202 may compare the detected phase relationship $\varnothing_i - \varnothing_k$ with a target phase relationship corresponding to the first electrode i and a second electrode k. Based on this comparison, processing circuitry 202 may determine one or more parameters of an electrical signal for delivery via the first electrode i and one or more parameters of an electrical signal for delivery via the second electrode k, where by determining the parameters, processing circuitry 202 causes the phase relationship $\varnothing_i - \varnothing_k$ to approach the target phase relationship corresponding to the first electrode i and a second electrode k.

Target phase relationships 212, in some cases, may represent target normalized phase-magnitude representations. As discussed above, when processing circuitry 202 determines one or more differences between detected phase relationships 210 and target phase relationships 212, processing circuitry 202 may adjust one or more parameters of electrical stimulation therapy delivered to patient 112 in order to cause the detected phase relationships 210 to approach the target phase relationships 212.

Figure 3:
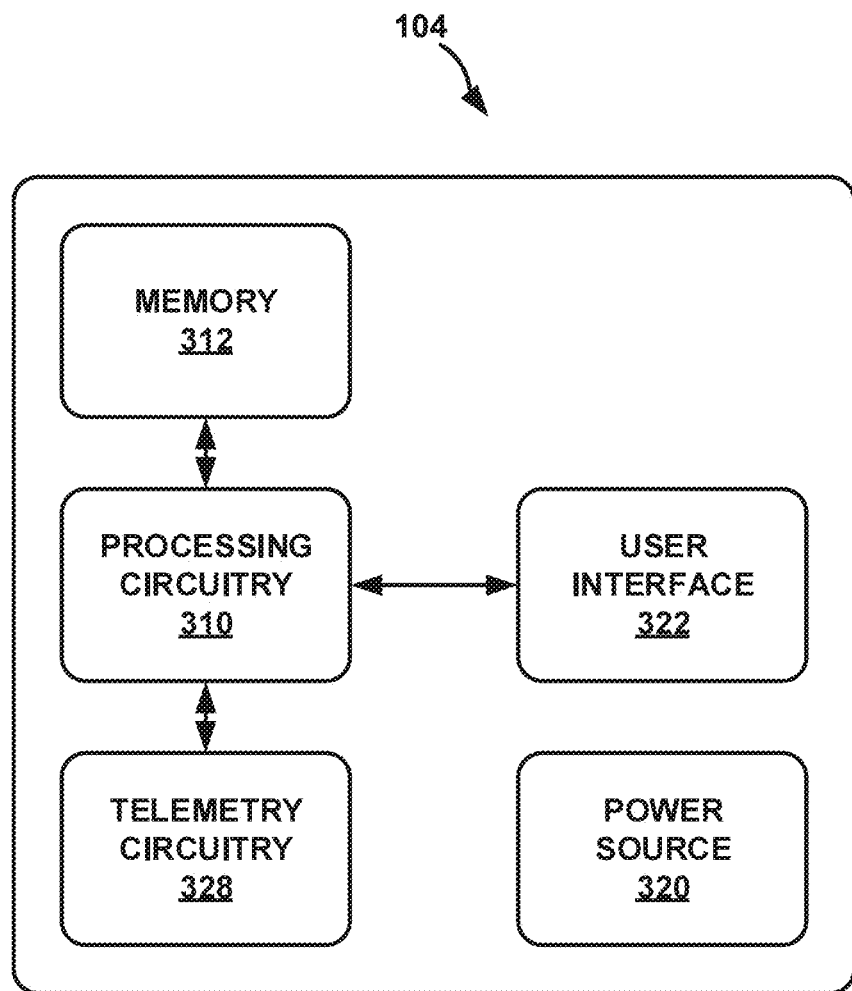
FIG. 3 is a block diagram illustrating an example configuration of the programmer of FIG. 1, in accordance with one or more techniques of this disclosure.

FIG. 3 is a block diagram illustrating an example configuration of the programmer 104 of FIG. 1, in accordance with one or more techniques of this disclosure. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include processing circuitry 310, memory 312, user interface 322, telemetry circuitry 328, and power source 330.

Processing circuitry 310 may include fixed function circuitry and/or programmable processing circuitry. Processing circuitry 310 may include, for example, microprocessors, DSPs, ASICs, FPGAs, equivalent discrete or integrated logic circuitry, or a combination of any of the foregoing devices or circuitry. Accordingly, processing circuitry 310 may include any suitable structure, whether in hardware, software, firmware, or any combination thereof, to perform the functions ascribed herein to programmer 104.

Memory 312 may store instructions that, when executed by processing circuitry 310, cause processing circuitry 310 and programmer 104 to perform various functions attributed to programmer 104 herein. Memory 312 may include one or both of a short-term memory or a long-term memory. The memory may include, for example, RAM, NVRAM, DRAM, SRAM, ROM, magnetic discs, optical discs, flash memory, or forms of EPROM or EEPROM. In some examples, the memory is used to store program instructions for execution by processing circuitry 310. For example, memory 312 may include instructions that cause processing circuitry 310 to obtain a parameter set from memory or receive a user input and send a corresponding command to IMD 106, or instructions for any other functionality. In addition, memory 312 may include a plurality of programs, where each program includes a parameter set that defines stimulation therapy. Memory 312 may store one or more target phase relationships.

In general, programmer 104 includes any suitable arrangement of hardware, alone or in combination with software and/or firmware, to perform the techniques attributed to programmer 104, and processing circuitry 310, user interface 322, and telemetry circuitry 328 of programmer 104. Although processing circuitry 310 and telemetry circuitry 328 are described as separate modules, in some examples, processing circuitry 310 and telemetry circuitry 328 may be functionally integrated with one another. In some examples, processing circuitry 310 and telemetry circuitry 328 correspond to individual hardware units, such as ASICs, DSPs, FPGAs, or other hardware units.

Memory 312 (e.g., a storage device) may store instructions that, when executed by processing circuitry 310, cause processing circuitry 310 and programmer 104 to provide the functionality ascribed to programmer 104 throughout this disclosure. For example, memory 312 may include instructions that cause processing circuitry 310 to obtain a parameter set from memory or receive a user input and send a corresponding command to IMD 106, or instructions for any other functionality. In addition, memory 312 may include a plurality of programs, where each program includes a parameter set that defines stimulation therapy.

User interface 322 may include a button or keypad, lights, a speaker for voice commands, a display, such as a liquid crystal (LCD), light-emitting diode (LED), or organic light-emitting diode (OLED). In some examples the display may be a touch screen. User interface 322 may be configured to display any information related to the delivery of stimulation therapy, identified patient behaviors, sensed patient parameter values, patient behavior criteria, or any other such information. User interface 322 may also receive user input via user interface 322. The input may be, for example, in the form of pressing a button on a keypad or selecting an icon from a touch screen.

Telemetry circuitry 328 may support wireless communication between IMD 106 and programmer 104 under the control of processing circuitry 310. Telemetry circuitry 328 may also be configured to communicate with another computing device via wireless communication techniques, or direct communication through a wired connection. In some examples, telemetry circuitry 328 provides wireless communication via an RF or proximal inductive medium. In some examples, telemetry circuitry 328 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection.

In some examples, processing circuitry 310 of programmer 104 defines parameters of electrical stimulation therapy, stored in memory 312, for delivering DBS to patient 112. In one example, processing circuitry 310 of programmer 104, via telemetry circuitry 328, issues commands to IMD 106 causing IMD 106 to deliver electrical stimulation therapy via electrodes 116, 118 via leads 114. Additionally, or alternatively, processing circuitry 310 may determine one or more target phase relationships (e.g., target phase relationships 212 of FIG. 2) and output, via telemetry circuitry 328, the one or more target phase relationships to IMD 106. In some examples, processing circuitry 310 may determine the one or more target phase relationships based on user input received via user interface 322. In this way, programmer 104 may cause IMD 106 to control one or more relative phase relationships between tissue regions of brain 120 based on target phase relationship 212.

In one or more examples, programmer 104 may be configured to perform one or more of the example techniques described herein. For instance, processing circuitry 310 may be configured to perform any of the example operations described above with respect to processing circuitry 202. For example, as described above, IMD 106 includes sensing circuitry 224 to receive the bioelectric signals from one or more electrodes, and stimulation generation circuitry 222 to deliver the electrical stimulation having the final therapy parameter value. In some examples, telemetry circuitry 328 may be configured to receive information of the bioelectric signals received by sensing circuitry 224 (e.g., telemetry circuitry 228 of IMD 106 may output information of the bioelectric signal to telemetry circuitry 328 of programmer 104). Processing circuitry 310 may perform the example operations described above with respect to processing circuitry 202. For example, processing circuitry 310 may determine one or more phase relationships based on time-varying measurements of CSD corresponding to electrodes 116, 118. Additionally, or alternatively, processing circuitry 310 may determine one or more adjustments to therapy parameters based on identified differences between the determined phase relationships and one or more target phase relationships.

FIG. 4A is a conceptual diagram illustrating a first example of electrodes on a lead with which CSD measurements are performed, in accordance with one or more techniques of this disclosure. To determine the CSD measurements for electrode 400, processing circuitry 202 or 310 may determine the difference between the voltage at electrode i 400 and electrode i+1 404, which is $\Delta V_{i,i+1}$ and determine the difference between the voltage at electrode i 400 and electrode i−1 402, which is $\Delta V_{i-1,i}$. For the first-time varying measurements, the processing circuitry 202 or 310 may then determine a difference between $\Delta V_{i-1,i}$ and $\Delta V_{i,i+1}$ as the second-order voltage differences between two electrodes that horizontally neighbor each electrode. Similarly, processing circuitry 202 or 310 may determine the difference between the voltage at electrode j 400 and electrode j+1 406, which is $\Delta V_{j,j+i}$ and determine the difference between the voltage at electrode j 400 and electrode j−1 408, which is $\Delta V_{j-1,j}$. The processing circuitry 202 or 310 may then determine a difference between $\Delta V_{j-1,j}$ and $\Delta V_{j,j+1}$ as the second-order voltage differences between two electrodes that vertically neighbor each electrode.

In some examples, the computation may be based on the "right hand rule" around the electrode (e.g., $\Delta V_{i-1,i}$=voltage at electrode 400−voltage at electrode 402 and $\Delta V_{i,i+1}$=voltage at electrode 404−voltage at electrode 400). Then, processing circuitry 202 may compute the approximation of the second-order difference $\Delta V_{i,i+1} - \Delta V_{i-1,i}$. The same applies in the z-direction (e.g., up and down).

In some examples, the most accurate estimate of the CSD may be achieved when the all voltages (or more typically, the voltage differences $\Delta V$), horizontal and vertical, are measured simultaneously. This is true for time domain or frequency domain (at least when subtracting phasors). Otherwise, measuring at separate times would require first aggregating (e.g. computing the power), then subtracting, which would only be a rough approximation of the CSD.

Figure 4B:
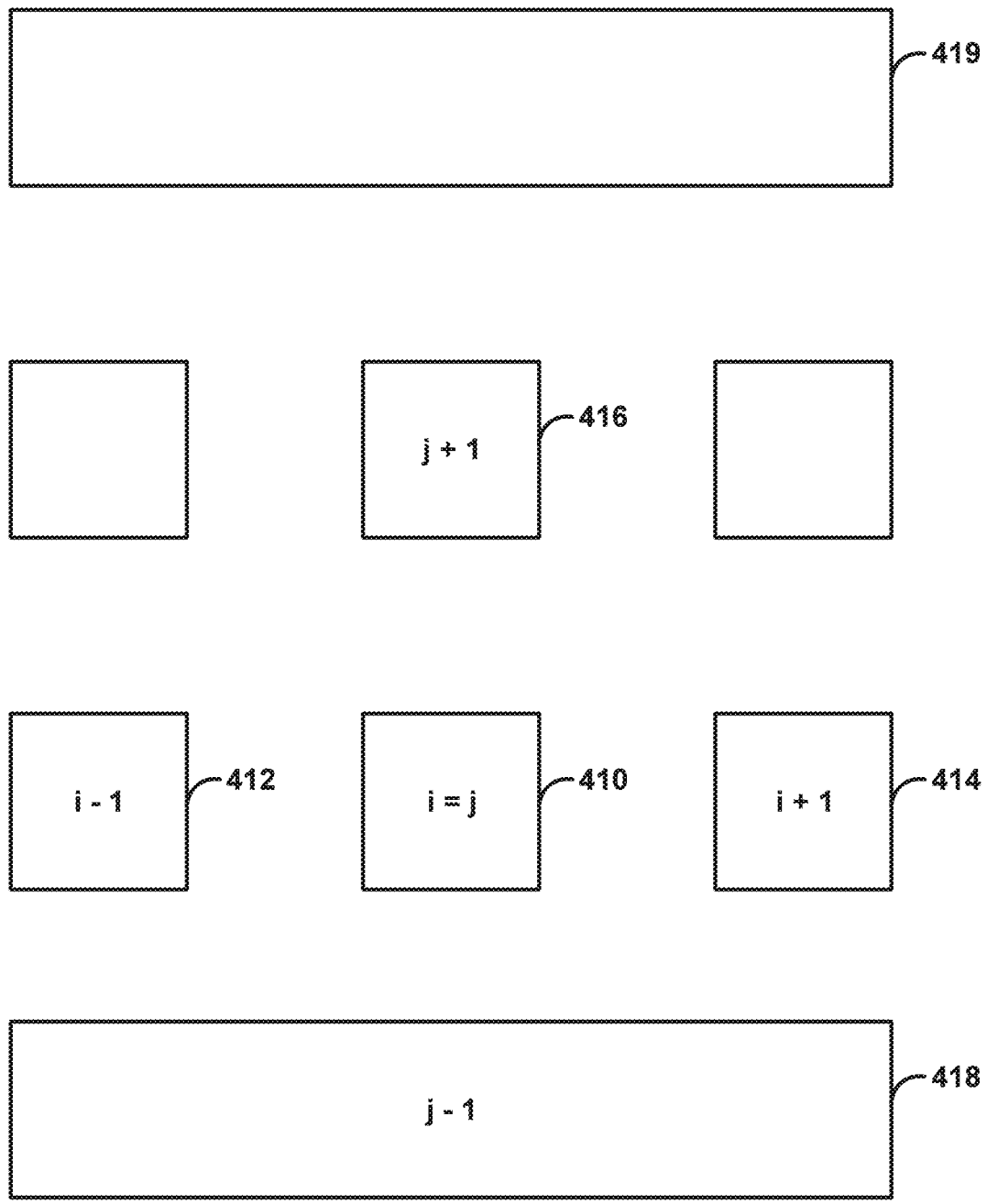
FIG. 4B is a conceptual diagram illustrating a second example of electrodes on a lead with which CSD measurements are performed, in accordance with one or more techniques of this disclosure.

FIG. 4B is a conceptual diagram illustrating a second example of electrodes on a lead with which CSD measurements are performed, in accordance with one or more techniques of this disclosure. FIG. 4B is similar to FIG. 4A, except FIG. 4B includes ring electrodes 418 and 419. To determine the CSD measurements for electrode 410, processing circuitry 202 may determine the difference between the voltage at electrode i 410 and electrode i+1 414, which is $\Delta V_{i,i+1}$ and determine the difference between the voltage at electrode i 410 and electrode i−1 412, which is $\Delta V_{i-1,i}$.

For the first-time varying measurements, the processing circuitry 202 or 310 may then determine a difference between $\Delta V_{i-1,i}$ and $\Delta V_{i,i+1}$ as the second-order voltage differences between two electrodes that horizontally neighbor each electrode. Similarly, processing circuitry 202 or 310 may determine the difference between the voltage at electrode j 410 and electrode j+1 416, which is $\Delta V_{j,j+1}$ and determine the difference between the voltage at electrode j 410 and electrode j−1 418, which is $\Delta V_{j-1,j}$. The processing circuitry 202 or 310 may then determine a difference between $\Delta V_{j-1,j}$ and $\Delta V_{j,j+1}$ as the second-order voltage differences between two electrodes that vertically neighbor each electrode.

In the example techniques described above, processing circuitry 202 or 310 may be configured to perform various operations as a way to determine CSD values. For instance, processing circuitry 202 or 310 may perform filtering or Fourier transforms as a way to perform operations in the time-domain or frequency-domain.

Figure 5:
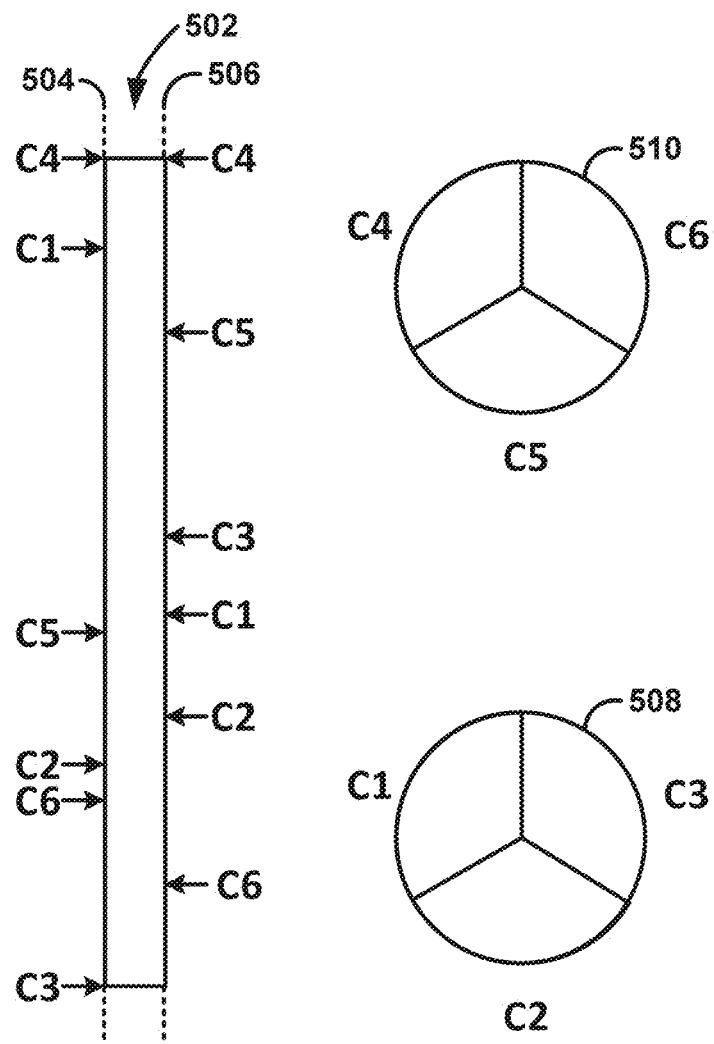
FIG. 5 is a conceptual diagram illustrating an example phase-magnitude representation for CSDs for a plurality of electrodes, in accordance with one or more techniques of this disclosure.

FIG. 5 is a conceptual diagram illustrating an example phase-magnitude representation for CSDs for a plurality of electrodes, in accordance with one or more techniques of this disclosure. FIG. 5 includes a phase-magnitude bar 502 including a magnitude scale 504 and a phase scale 506, a first electrode diagram 508 including electrodes C1-C3, and a second electrode diagram 510 including electrodes C4-C6. Phase-magnitude bar 502 shows the phase-magnitude representation (e.g., normalized phase-magnitude representation, but such normalization may not be necessary in all examples) for electrodes C1-C6, where electrodes C1-C3 are at a first level on a lead and electrodes C4-C6 are at a second level on the lead. In the example of FIG. 5, the time-varying signal from electrode C4 may provide the reference phase since the magnitude of the CSD corresponding to C4 is greater than the respective magnitudes of the CSD corresponding to each other electrode (e.g., $\emptyset_k$ is phase of the time-varying signal at electrode C4 for the frequency component $w_0$, where frequency component $w_0$ is a frequency component having a largest transform coefficient in a time-varying measurement of a CSD having a largest average level value).

As seen on the magnitude scale 504, electrode C4 is associated with the greatest magnitude, electrode C1 is associated with the second greatest magnitude, electrode C5 is associated with the third greatest magnitude, electrode C2 is associated with the fourth greatest magnitude, electrode C6 is associated with the fifth greatest magnitude, and electrode C3 is associated with the sixth greatest (e.g., the smallest) magnitude. As seen on the phase scale 506, electrode C4 (the reference electrode) is associated with the reference phase (360°), electrode C5 is associated with the second highest phase relative to the reference phase, electrode C3 is associated with the third highest phase relative to the reference phase, electrode C1 is associated with the fourth highest phase relative to the reference phase, electrode C2 is associated with the fifth highest phase relative to the reference phase, and electrode C6 is associated with the sixth highest phase relative to the reference phase. The magnitude and phase associated with electrodes C1-C6 may be based on the value of $A_{w0,i\_norm}$. The phase associated with electrodes C1-C6 are indicative of an amount of phase difference from the reference phase (e.g., $(\uparrow_i - \emptyset_k)$).

Figure 6A:
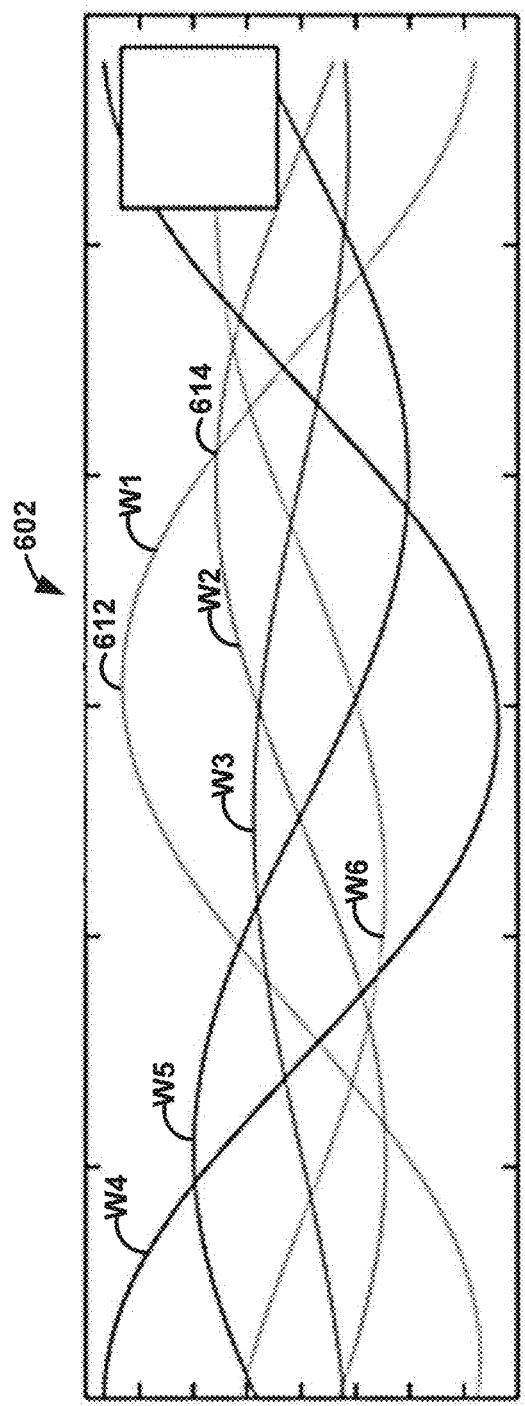
FIGS. 6A and 6B are graphs illustrating a waveform plot and a phase-magnitude plot, respectively, corresponding to electrodes C1-C6 of FIG. 5, in accordance with one or more techniques of this disclosure.
Figure 6B:
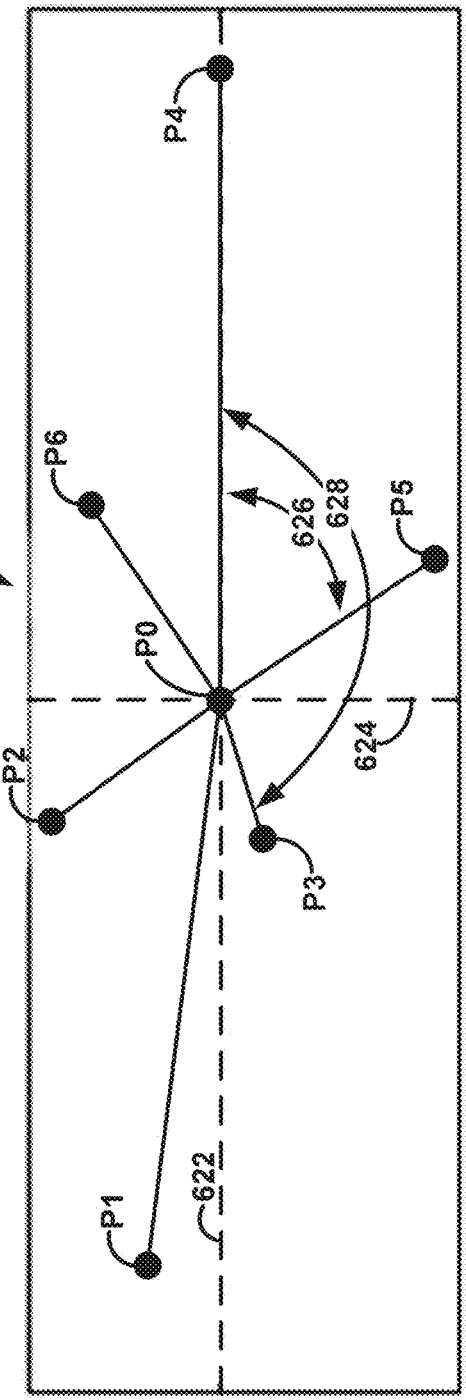

FIGS. 6A and 6B are graphs illustrating a waveform plot 602 and a phase-magnitude plot 604, respectively, corresponding to electrodes C1-C6 of FIG. 5, in accordance with one or more techniques of this disclosure. Waveform plot 602 includes a first waveform W1 corresponding to a single period of the normalized FTC of the time-varying CSD corresponding to the electrode C1, a second waveform W2 corresponding to a single period of the normalized FTC of the time-varying CSD corresponding to the electrode C2, a third waveform W3 corresponding to a single period of the normalized FTC of the time-varying CSD corresponding to the electrode C3, a fourth waveform W4 corresponding to a single period of the normalized FTC of the time-varying CSD corresponding to the electrode C4, a fifth waveform W5 corresponding to a single period of the normalized FTC of the time-varying CSD corresponding to the electrode C5, and a sixth waveform W6 corresponding to a single period of the normalized FTC of the time-varying CSD corresponding to the electrode C6.

As seen in waveform plot 602 of FIG. 6A, the first waveform W1, the second waveform W2, the third waveform W3, the fourth waveform W4, the fifth waveform W5, and the sixth waveform W6 all have different phases and different magnitudes. As described herein, the relative "phase" of a waveform refers to a position of a point on one waveform relative to a position of a corresponding point on another waveform. For example, since the peak 612 of the first waveform W1 corresponding to the electrode C1 occurs at a different time than the peak 614 of the second waveform W2 corresponding to the electrode C2, the phase of the first waveform W1 is different than the phase of the second waveform W2, meaning that the first waveform W1 and the second waveform W2 have a "non-synchronous" phase relationship. In some cases, a pair of waveforms may have the same phase, representing a "synchronous" phase relationship, when peaks of one waveform align with peaks of the other waveform and valleys of one waveform align with valleys of the other waveform. As seen in FIG. 6A, a magnitude of the fourth waveform W4 corresponding to the electrode C4 is greater than the magnitude of the second waveform W2 corresponding to the electrode C2, for example.

The phase and the magnitude of each of the six waveforms is shown on phase-magnitude plot 604. For example, point P1 on phase-magnitude plot 604 is a phase-magnitude representation of the first waveform W1 on the waveform plot 602, point P2 on phase-magnitude plot 604 is a phase-magnitude representation of the second waveform W2 on the waveform plot 602, point P3 on phase-magnitude plot 604 is a phase-magnitude representation of the third waveform W3 on the waveform plot 602, point P4 on phase-magnitude plot 604 is a phase-magnitude representation of the fourth waveform W4 on the waveform plot 602, point P5 on phase-magnitude plot 604 is a phase-magnitude representation of the fifth waveform W5 on the waveform plot 602, and point P6 on phase-magnitude plot 604 is a phase-magnitude representation of the sixth waveform W6 on the waveform plot 602.

The x-axis 622 and the y-axis 624 of phase-magnitude plot 604 may form a Cartesian coordinate system for points C1-C6 to be placed on phase-magnitude plot 604 according to their respective phases and magnitudes. For example, point P4 is placed on the x-axis 622 of phase-magnitude plot 604 in order to indicate a "reference" phase. For example, point P4 indicates a phase and a magnitude of the fourth waveform W4 on the waveform plot 602, where the phase of each of the other waveforms of plot 602 are plotted on phase-magnitude plot 604 in order to indicate their phase relative to the phase of the fourth waveform W4. For example, the angular displacement 626 between point P5 and point P4 shown on phase-magnitude plot 604 indicates a difference between the phase of the fourth waveform W4 and the phase of the fifth waveform W5. Additionally, the angular displacement 628 between point P3 and point P4 shown on phase-magnitude plot 604 indicates a difference between the phase of the third waveform W3 and the phase of the fifth waveform W5. As seen in FIG. 3B, angular displacement 628 is greater than angular displacement 626, meaning that the difference between the phase of the fourth waveform and the phase of the fifth waveform is greater than the difference between the phase of the fourth waveform and the phase of the third waveform.

Consequently, phase-magnitude plot 604 indicates a set of phase relationships, where each phase relationship of the set of phase relationships represent a phase of one waveform relative to a phase of a reference waveform. Processing circuitry 202 of IMD 106 may determine timing of stimulation to be delivered to patient 105 in order to cause a phase relationship to approach a target phase relationship, such as by stimulating to increase or decrease phase synchronicity between two different neural target populations. For example, processing circuitry 202 may determine for the timing of electrical stimulation in order to cause the phase of signals from neural population represented by the fifth waveform W5 to approach a phase of signals from the neural population represented by the fourth waveform W4. Responsive to processing circuitry 202 determining the one or more parameters, point P5 may shift over time to be located on the x-axis 624 of plot 604, indicating that the phase of the fourth waveform is the same as the phase of the fifth waveform, representing a synchronous phase relationship. Alternatively, processing circuitry 202 may determine one or more parameters for electrical stimulation in order to cause the phase of the fifth waveform W5 to move farther away from the fourth waveform W4, thus increasing the angular displacement 626 shown on plot 604. In any case, processing circuitry 202 may control waveforms W1-W6 to approach respective target phase relationships in order to achieve one or more therapy outcomes such as decreasing a severity of involuntary tremors.

Figure 7:
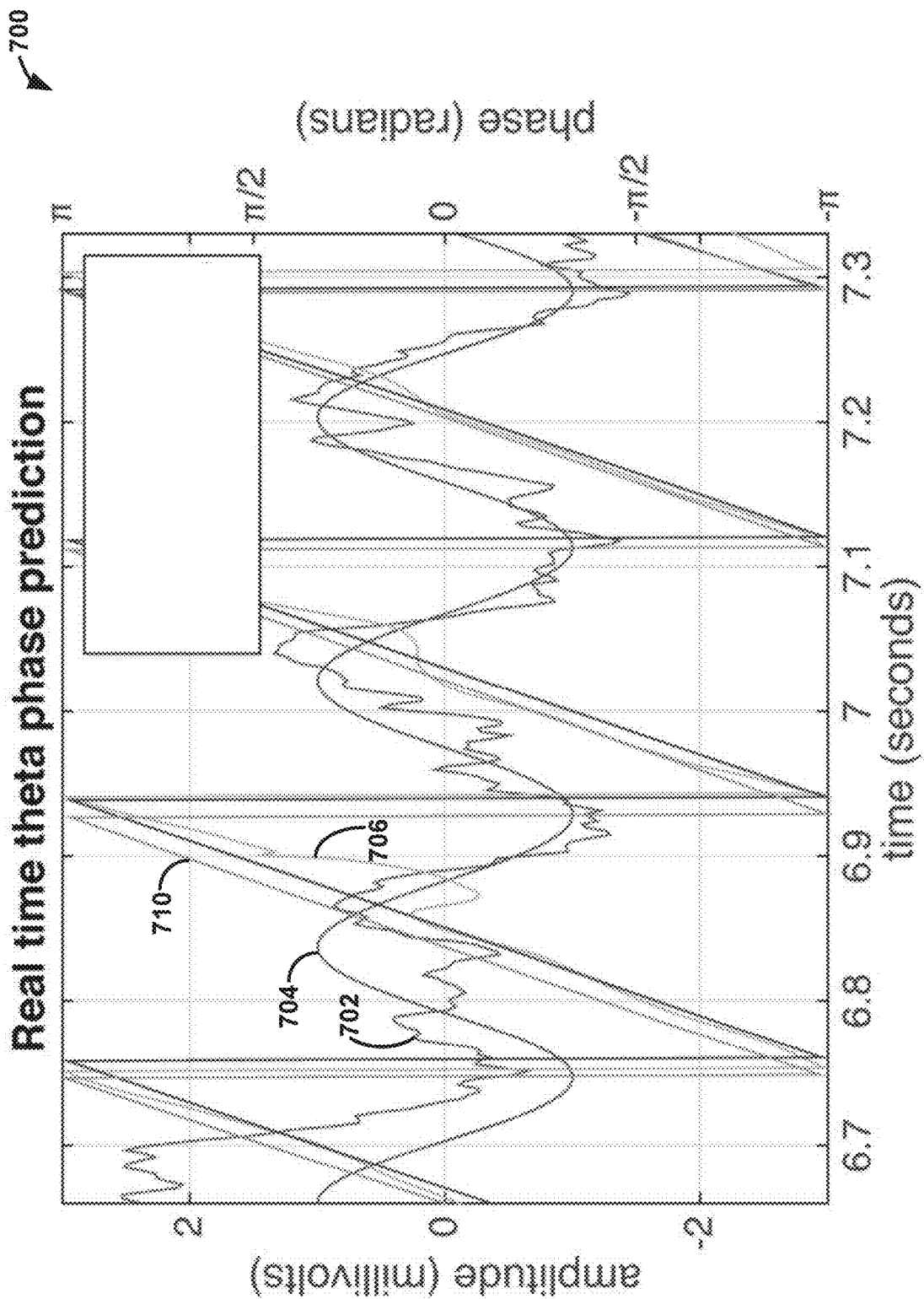
FIG. 7 is a graph illustrating a plot which indicates a real-time phase detection of a physiological signal, in accordance with one or more techniques of this disclosure.

FIG. 7 is a graph illustrating a plot 700 which indicates a real-time phase detection of a physiological signal, in accordance with one or more techniques of this disclosure. Plot 700 includes a physiological signal plot 702, a physiological signal plot with reduced noise 704, a real-time phase plot 706, and an actual phase plot 710. In some examples, IMD 106 may perform real-time phase detection of one or more electrical signals sensed by IMD 106 while IMD 106 is delivering one or more stimulation pulses to brain 120. For example, IMD 106 may first determine the relative phase differences (e.g., determine relative phase relationships as shown in FIGS. 6A-6B) between electrodes while IMD 106 is not delivering stimulation to brain 120. While IMD 106 is providing stimulation to brain 120 in order to cause a relative phase relationships to approach a respective target phase relationship, IMD 106 may measure the real-time phase of each signal of interest (an) corresponding to the relative phase relationship in order to continuously adjust the relative timing of stimulation across active electrodes of electrodes 116, 118 based on the relative phase difference measured initially while IMD 106 is not delivering stimulation.

In some examples, processing circuitry 202 of FIG. 2 may determine one or more of graphs 702, 704, 706, 710 while performing real-time phase detection. For example, plot 700 a real-time phase 710 of a physiological signal (e.g., physiological signal graph 702 and physiological signal graph with reduced noise 704). In some examples, the physiological signal graph 702 and the physiological signal graph with reduced noise 704 may represent a theta wave detected in the brain 120 of patient 112, but this is not required. The physiological signal graph 702 and the physiological signal graph with reduced noise 704 may represent one or more other brain signals such as beta waves or gamma waves. As seen in FIG. 7, the real-time phase graph 706 is offset from the actual phase graph 710. The actual phase plot 710 may represent a phase which is detected while IMD 106 detects one or more relative phase relationships as shown in FIGS. 6A-6B. Consequently, IMD 106 may apply one or more offsets when delivering stimulation to brain 120 based on the detected real-time phase shown by real-time phase plot 706. In some examples, IMD 106 may determine one or more phase-magnitude relationships using aggregate data which is collected at an earlier time.

FIGS. 8A-8F are graphs illustrating a set of plots which indicate a relationship between pairs of physiological signals, in accordance with one or more techniques of this disclosure. Plot 810 of FIG. 8A shows a synchronous phase relationship between a first physiological signal 812 and a second physiological signal 814. Plot 820 of FIG. 8B shows a synchronous phase relationship between a third physiological signal 822 and a fourth physiological signal 824. Plot 830 of FIG. 8C illustrates a "coincidence detection" of a peak feature of a first physiological signal 832 and a peak feature of a second physiological signal 834. Plot 840 of FIG. 8D illustrates a first physiological signal 842 corresponding to a first tissue region of brain 120 and a second physiological signal 844 corresponding to a second tissue region of brain 120, where the first physiological signal 842 and the second physiological signal 844 indicate neural communication between the first tissue region and the second tissue region. Plot 850 of FIG. 8E may be substantially the same as plot 840 of FIG. 8D. FIG. 8E also includes a neuron diagram 856 which indicates the neural connection between the first tissue region and the second tissue region. Plot 860 of FIG. 8F shows example implementation of long-term potentiation (LTP) and long-term depression (LTD) when a synchronous relationship exists between a first physiological signal 862 of a first tissue region and a second physiological signal 864 of a second tissue region.

Plot 810, for example, includes the first physiological signal 812 and the second physiological signal 814. As seen in FIG. 8A, a synchronous phase relationship exists between the first physiological signal 812 and the second physiological signal 814. That is, one or more peaks of the first physiological signal 812 align with a corresponding peak of the second physiological signal 814. This means that a level of neural communication may exist between the first tissue region and the second tissue region. For example, neural activity in the second tissue region may cause neural activity in the first tissue region and neural activity in the first tissue region may cause neural activity in the second tissue region. In some examples, IMD 106 may determine that phase synchronization exists between the first physiological signal 812 corresponding to the first tissue region and the second physiological signal 814 corresponding to the second tissue region.

Plot 820 includes the first physiological signal 822 and the second physiological signal 824. As seen in FIG. 8B, a non-synchronous phase relationship exists between the first physiological signal 812 and the second physiological signal 814. That is, one or more peaks of the first physiological signal 812 do not align with a corresponding peak of the second physiological signal 814. This means that a level of neural communication does not exist between the first tissue region and the second tissue region. For example, neural activity in the second tissue region might not cause neural activity in the first tissue region and neural activity in the first tissue region might not cause neural activity in the second tissue region. IMD 106 may determine that a non-synchronous phase relationship does not exist between the first physiological signal 822 corresponding to a first tissue region and the second physiological signal 824 corresponding to a second tissue region.

Plot 830 illustrates a coincidence detection between a pair of physiological signals. A "coincidence" may refer to an occurrence in which a peak of one physiological signal occurs at the same time as a peak of another physiological signal. IMD 106 may perform one or more coincidence detection measurements in order to determine whether the first physiological signal 832 and the second physiological signal 834 have a synchronous phase relationship. For example, plot 840 illustrate a first physiological signal 842 corresponding to the first physiological signal 832 of plot 830 and a second physiological signal 844 corresponding to the second physiological 834 of plot 830. As seen in FIG. 8D, a synchronous phase relationship exists between the first physiological signal 842 and the second physiological signal 844. This means that a level of neural communication exists between a first tissue region corresponding to the first physiological signal 842 and a second tissue region corresponding the second physiological signal 844. For example, neuron diagram 856 of FIG. 8E shows that neural activity in the second tissue region may cause neural activity to occur in the first tissue region while a synchronous relationship exists between the first physiological signal 852 and the second physiological signal 854.

In some examples, IMD 106 may deliver LTP stimulation and/or LTD stimulation in order to deliver therapy to patient 105. LTP stimulation represents stimulation in which IMD 106 delivers one or more stimulation pulses at respective peaks of a physiological signal, such as second physiological signal 864. LTP stimulation causes strengthening of synapses in the brain tissue. LTD stimulation represents stimulation in which IMD 106 delivers one or more stimulation pulses at respective valleys of a physiological signal, such as second physiological signal 864. LTD stimulation causes weakening of synapses in the brain tissue. Plot 860 illustrates a scenario in which IMD 106 may deliver LTP stimulation and/or LTD stimulation to the second tissue region. Since a synchronous phase relationship exists between the second tissue region and the first tissue region, delivering LTP stimulation and/or LTD stimulation to the second tissue region causes LTP and/or LTD to occur in the first tissue region.

Figure 9:
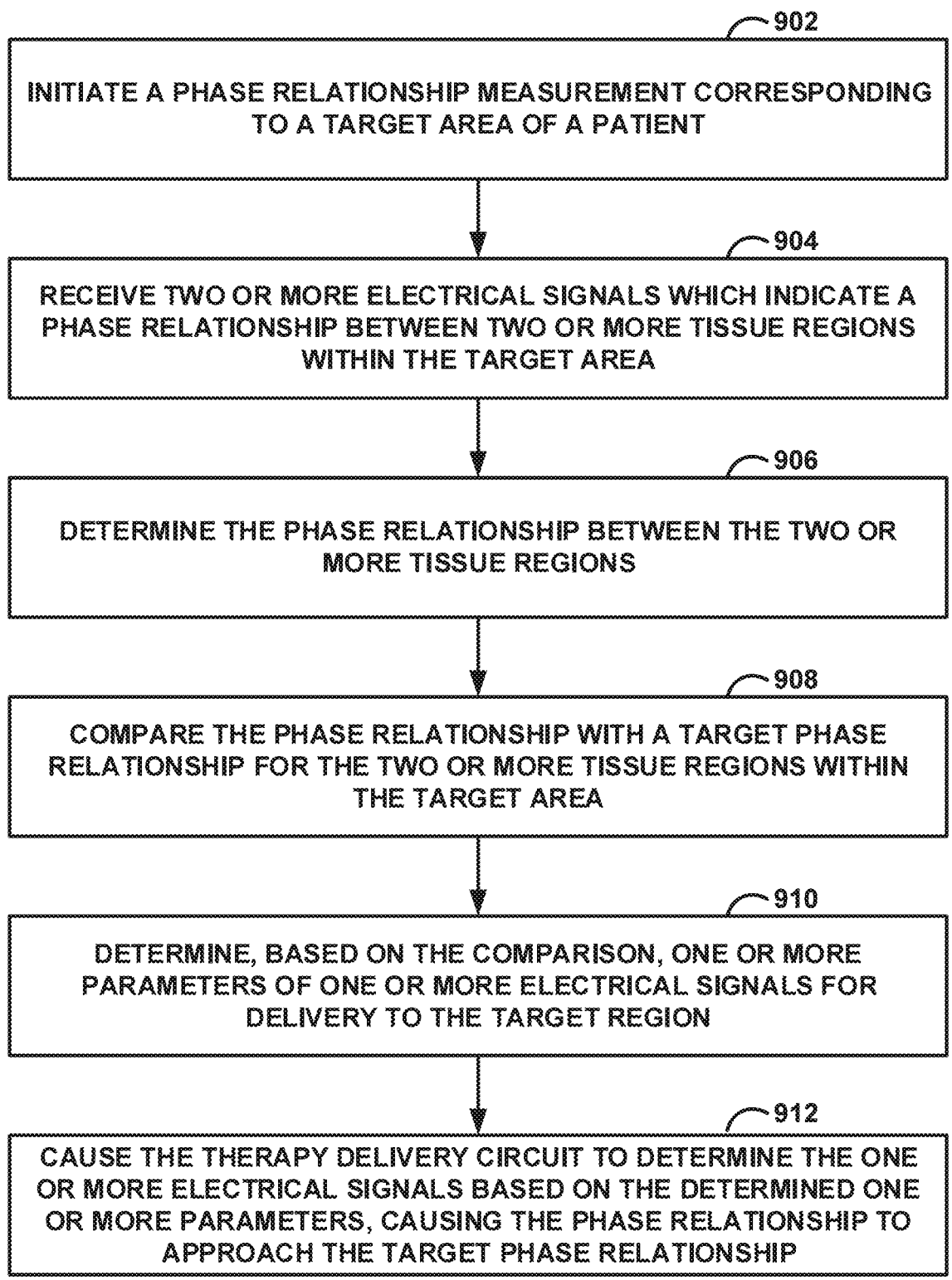
FIG. 9 is a flow diagram illustrating an example operation for controlling stimulation based on one or more phase relationships, in accordance with one or more techniques of this disclosure.

FIG. 9 is a flow diagram illustrating an example operation for controlling stimulation based on one or more phase relationships, in accordance with one or more techniques of this disclosure. FIG. 9 is described with respect to programmer 104 and IMD 106 of FIGS. 1-3. However, the techniques of FIG. 9 may be performed by different components of programmer 104 and IMD 106 or by additional or alternative medical device systems.

IMD 106 may initiate a phase relationship measurement corresponding to a target area of a patient (902). In some examples, IMD 106 may initiate the phase relationship measurement responsive to receiving information indicative of a user instruction to initiate the phase relationship measurement. In some examples, IMD 106 may receive the user instruction to perform the phase relationship measurement from programmer 104 and initiate the phase relationship measurement. For example, IMD 106 may receive the user instruction to initiate the phase relationship measurement in response to a decreased efficacy of therapy as perceived by patient 105. In some examples, IMD 106 may perform a phase relationship measurement according to a phase relationship measurement program stored in a memory of IMD 106. For example, the phase relationship measurement program may include instructions to perform phase relationship measurements hourly, daily, weekly, or at another time interval. IMD 106, based on the phase relationship measurement program, whether to initiate the phase relationship measurement. This may ensure that IMD 106 continuously checks to make sure that one or more phase relationships align with one or more target phase relationships such that patient 105 receives more effective therapy as compared with systems which do not regularly assess whether detected phase relationships align with target phase relationships.

IMD 106 may receive, via electrodes 116, 118, two or more electrical signals which indicate a phase relationship between two or more tissue regions within the target area (904). In some examples, the target area is a target area of brain 120. IMD 106 may receive a time-varying voltage signal (e.g., a time varying of LFP) from each electrode of electrodes 116 and determine the phase relationship between the two or more regions based on the respective time-varying voltage signals. For example, each electrode of electrodes 116, 118 may be proximate to a respective tissue region of a set of tissue regions. The time-varying voltage signal received by IMD 106 from each electrode of electrodes 116, 118 may represent a time-varying voltage corresponding to the respective tissue region of the set of tissue regions.

IMD 106 may determine the phase relationship between the two or more tissue regions (906). In order to determine the phase relationship, IMD 106 may determine two or more CSDs based on the electrical signals. For example, IMD 106 may determine, based on the set of time-varying voltage signals received by IMD 106 from the set of electrodes 116, 118, a set of time-varying measurements of CSD. For example, to determine a time-varying measurement of CSD, IMD 106 may determine a first time-varying measurement based on a second-order voltage difference between a time-varying voltage signal corresponding to a first electrode of electrodes 116, 118 of the plurality of electrodes and a time-varying voltage signal corresponding to a first electrode of electrodes 116, 118, where the first electrode and the second electrode horizontally neighbor the respective electrode corresponding to the time-varying measurement of CSD. Additionally, to determine the time-varying measurement of CSD, IMD 106 may determine a second time-varying measurement based on a second-order voltage difference between a time-varying voltage signal corresponding to a third electrode of electrodes 116, 118 of the plurality of electrodes and a time-varying voltage signal corresponding to a fourth electrode of electrodes 116, 118, where the third electrode and the fourth electrode vertically neighbor the respective electrode corresponding to the time-varying measurement of CSD. IMD 106 may determine the respective time-varying measurement of the CSD based on the respective first time-varying measurement and the respective second time-varying measurement.

IMD 106 may determine a time-varying measurement of CSD corresponding to each electrode of electrodes 116, 118. In some examples, IMD 106 may calculate a Fourier transform of each time-varying measurement of CSD in order to determine a phase-magnitude representation corresponding to each time-varying measurement of CSD. That is, IMD 106 may determine a phase and a magnitude corresponding to each time-varying measurement of CSD determined by IMD 106. To determine the phase relationship between the two or more tissue regions, IMD 106 may determine a difference between a first phase corresponding to a first time-varying measurement of CSD associated with a first tissue region and a second phase corresponding to a second time-varying measurement of CSD associated with a second tissue region. In some examples, one of the first time-varying measurement of CSD and the second time-varying measurement of CSD may represent a reference time-varying measurement of CSD.

IMD 106 may select one time-varying measurement of CSD of the set of time-varying measurements CSDs to represent a reference time-varying measurement of CSD having a reference phase. In some examples, IMD 106 may select the time-varying measurement of CSD having the greatest amplitude to represent the reference time-varying measurement of CSD. IMD 106 may determine the phase of each time-varying measurement of CSD relative to the reference phase of the reference time-varying measurement of CSD. The difference between the phase of a first time-varying measurement of CSD and the phase of the reference time-varying measurement of CSD may represent a relative phase relationship between a first tissue region corresponding to the first time-varying measurement of CSD and a second tissue region corresponding to the reference time-varying measurement of CSD.

IMD 106 may compare the phase relationship indicated by the two or more electrical signals with a target phase relationship for the two or more tissue regions within the target area (908). For example, the target phase relationship may include a first target phase for a first tissue region of the target tissue and a second target phase for a second tissue region of the target tissue. It may be beneficial to compare the phase relationship and the target phase relationship in order to determine whether a difference exists between the phase relationship and the target phase relationship. When the detected phase relationship differs from the target phase relationship, an efficacy of the therapy delivered to patient 105 may decrease as compared with a situation in which the detected phase relationship is substantially the same as the target phase relationship. For example, the phase relationship between the tissue regions may a determine a level of neural communication between the two or more tissue regions. The phase relationship may represent a phase relationship between physiological signals of a first tissue region and physiological signals of a second tissue region.

When the phase relationship between the first tissue region and the second tissue region is a synchronous phase relationship where the phase of the first tissue region is substantially the same as the phase of the second tissue region, neural activity occurring in the first tissue region may cause neural activity to occur in the second tissue region. As such, when IMD 106 stimulates the first tissue region when a synchronous phase relationship exists between the first tissue region and the second tissue region, neural activity induced by the stimulation of the first tissue region may cause the second tissue region to increase.

When the phase relationship between the first tissue region and the second tissue region is a non-synchronous phase relationship where the phase of the first tissue region is substantially different than the phase of the second tissue region, neural activity occurring in the first tissue region might not cause neural activity to occur in the second tissue region. As such, when IMD 106 stimulates the first tissue region when a non-synchronous phase relationship exists between the first tissue region and the second tissue region, neural activity induced by the stimulation of the first tissue region might not cause any change in the neural activity of the second tissue region.

Consequently, IMD 106 may control one or more relative phase relationships between tissue regions of the brain 120 in order to control a manner or a level in which neural activity exists between these tissue regions. Neural activity between tissue regions of the brain may have an effect on one or more patient conditions such as involuntary tremors and/or seizures. For example, IMD 106 may determine, based on the comparison between the phase relationship and the target phase relationship, one or more parameters of one or more electrical signals for delivery to the target region (910). Subsequently, IMD 106 may cause a therapy delivery circuit (e.g., stimulation generation circuitry 222 of FIG. 2) to determine the one or more electrical signals based on the determined one or more parameters, causing the phase relationship to approach the target phase relationship (912).

In some examples, a phase of physiological signals within a tissue region of brain 120 may be substantially the same phase as a one or more electrical signals delivered to the tissue region by IMD 106 during a window of time which begins prior to a current time. For example, when IMD 106 delivers one or more electrical signals to the tissue region at a first phase, physiological signals originating within the tissue region may approach the first phase. In some examples, the physiological signals originating within the tissue region may remain at the first phase for a period of time after IMD 106 concludes delivery of the one or more electrical signals at the first phase. Subsequently, the phase of the physiological signals originating within the tissue region may drift from the first phase following the period of time which ends after IMD 106 concludes delivery of the one or more electrical signals at the first phase. It may be beneficial to return the physiological signals to the first phase by delivering one or more additional electrical signals to the tissue region at the first phase.

For example, IMD 106 may cause a relative phase relationship between physiological signals of a first tissue region and physiological signals of a second tissue region to approach a target phase relationship by delivering one or more electrical signals to the first tissue region at a first phase and delivering one or more electrical signals to the second tissue region at a second phase. This may cause the physiological signals of the first tissue region to approach the first phase and cause the physiological signals of the second tissue region to approach the second phase. The relationship between the first phase and the second phase may represent the target phase relationship which IMD 106 causes the first tissue region and the second tissue region to approach. This may affect the level of neural communication between the first tissue region and the second tissue region, improving one or more patient conditions (e.g., decreasing a severity of involuntary tremors) in patient 112.

Figure 10:
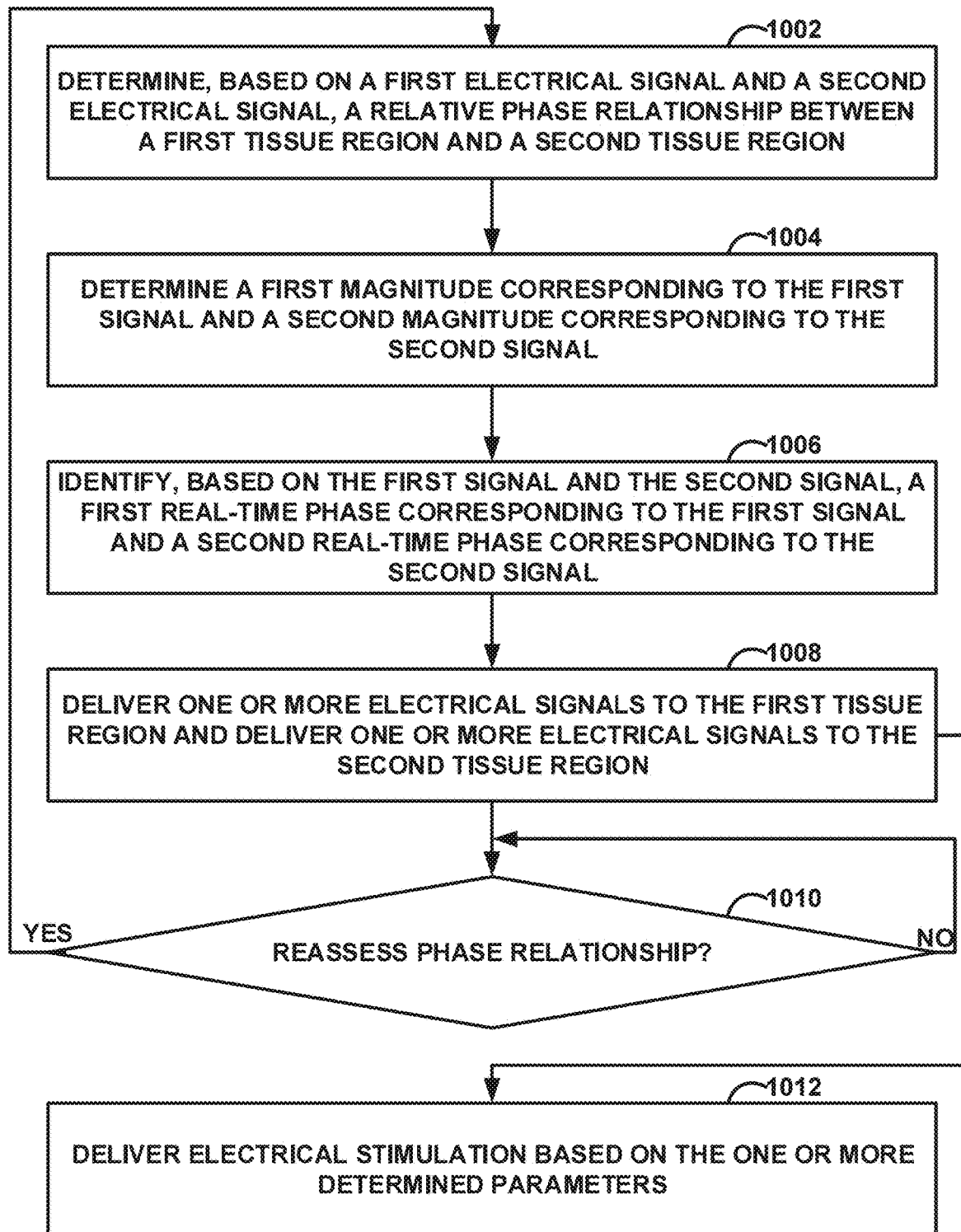
FIG. 10 is a flow diagram illustrating an example operation for determining whether to reassess a phase relationship, in accordance with one or more techniques of this disclosure.

FIG. 10 is a flow diagram illustrating an example operation for determining whether to reassess a phase relationship, in accordance with one or more techniques of this disclosure. FIG. 10 is described with respect to programmer 104 and IMD 106 of FIGS. 1-3. However, the techniques of FIG. 10 may be performed by different components of programmer 104 and IMD 106 or by additional or alternative medical device systems.

IMD 106 may determine, based on a first electrical signal and a second electrical signal, a relative phase relationship between a first tissue region of brain 120 and a second tissue region of brain 120 (1002). In some examples, the first electrical signal corresponds to a time-varying measurement of CST associated with a first electrode of electrodes 116, 118 proximate to the first tissue region and the second electrical signal corresponds to a time-varying measurement of CST associated with a second electrode of electrodes 116, 118 proximate to the second tissue region. The relative phase relationship determined by IMD 106 may represent a relative phase relationship between physiological signals of the first tissue region and physiological signals of the second tissue region. Additionally, IMD 106 may determine a first magnitude corresponding to the first signal and a second magnitude corresponding to the second signal (1004). In some examples, IMD 106 may determine the relative phase relationship based on the example operation of FIG. 9, but this is not required. IMD 106 may determine the relative phase relationship based on one or more other techniques.

In some examples, IMD 106 may determine the relative phase relationship while IMD 106 is not delivering electrical stimulation to patient 112 via electrodes 116, 118. It may be beneficial for IMD 106 to cause the detected relative phase relationship to approach a target phase relationship in order to control a level of neural communication between the first tissue region and the second tissue region. In order for IMD 106 to cause the relative phase relationship to approach the target phase relationship, IMD 106 may identify a first real-time phase corresponding to physiological signals of the first tissue region and identify a second real-time phase corresponding to physiological signals of the second tissue region (1006). IMD 106 may deliver one or more electrical signals to the first tissue region at a first phase and deliver one or more electrical signals to the second tissue region (1008) at a second phase while IMD 106 identifies the first real-time phase and identifies the second real-time phase, so that IMD 106 may monitor whether the phase relationship between the first tissue region and the second tissue region is approaching the target phase relationship. In other words, IMD 106 delivers the first one or more electrical signals to the first tissue region and delivers the second one or more electrical signals to the second tissue region in order to cause the phase relationship to approach the target phase relationship, and IMD 106 monitors the first real-time phase and the second real-time phase in order to determine whether the phase relationship between he first tissue region and the second tissue region is approaching the target phase.

In some examples, IMD 106 may perform real-time phase detection while IMD 106 is delivering one or more electrical signals to the first tissue region and delivering one or more electrical signals to the second region in order to reliably determine the phase of the first region and the phase of the second region while IMD 106 delivers stimulation. For example, determining one or more relative phase relationships between target tissue regions may be more difficult when IMD 106 delivers stimulation as compared with situations in which IMD 106 is not delivering stimulation. Real-time phase detection may consume more power than determining relative phase relationships while IMD 106 is not delivering stimulation. As such, it may be beneficial to only perform real-time phase detection while IMD 106 is delivering stimulation in order to limit a power consumption of IMD 106.

At block 1010, IMD 106 may determine whether to reassess the phase relationship between the first signal and the second signal. When IMD 106 determines to reassess the phase relationship ("YES" branch of block 1010), the example operation may return to block 1002. When IMD 106 determines not to reassess the phase relationship ("NO" branch of block 1010), IMD 106 may decline to reassess the phase relationship. IMD 106 may deliver electrical stimulation based on the one or more determined parameters responsive to determining the one or more parameters (1012).

In some examples, IMD 106 may determine to reassess the phase relationship responsive to receiving information indicative of a user instruction to initiate the phase relationship measurement. For example, IMD 106 may receive the user instruction to initiate the phase relationship measurement in response to a decreased efficacy of therapy as perceived by patient 105. In some examples, IMD 106 may determine to reassess the phase relationship according to a phase relationship measurement program stored in a memory of IMD 106. For example, the phase relationship measurement program may include instructions to perform phase relationship measurements hourly, daily, weekly, or at another time interval. IMD 106, based on the phase relationship measurement program, may determine whether to reassess the phase relationship. This may ensure that IMD 106 continuously checks to make sure that one or more phase relationships align with one or more target phase relationships such that patient 105 receives more effective therapy as compared with systems which do not regularly assess whether detected phase relationships align with target phase relationships.

Figure 11:
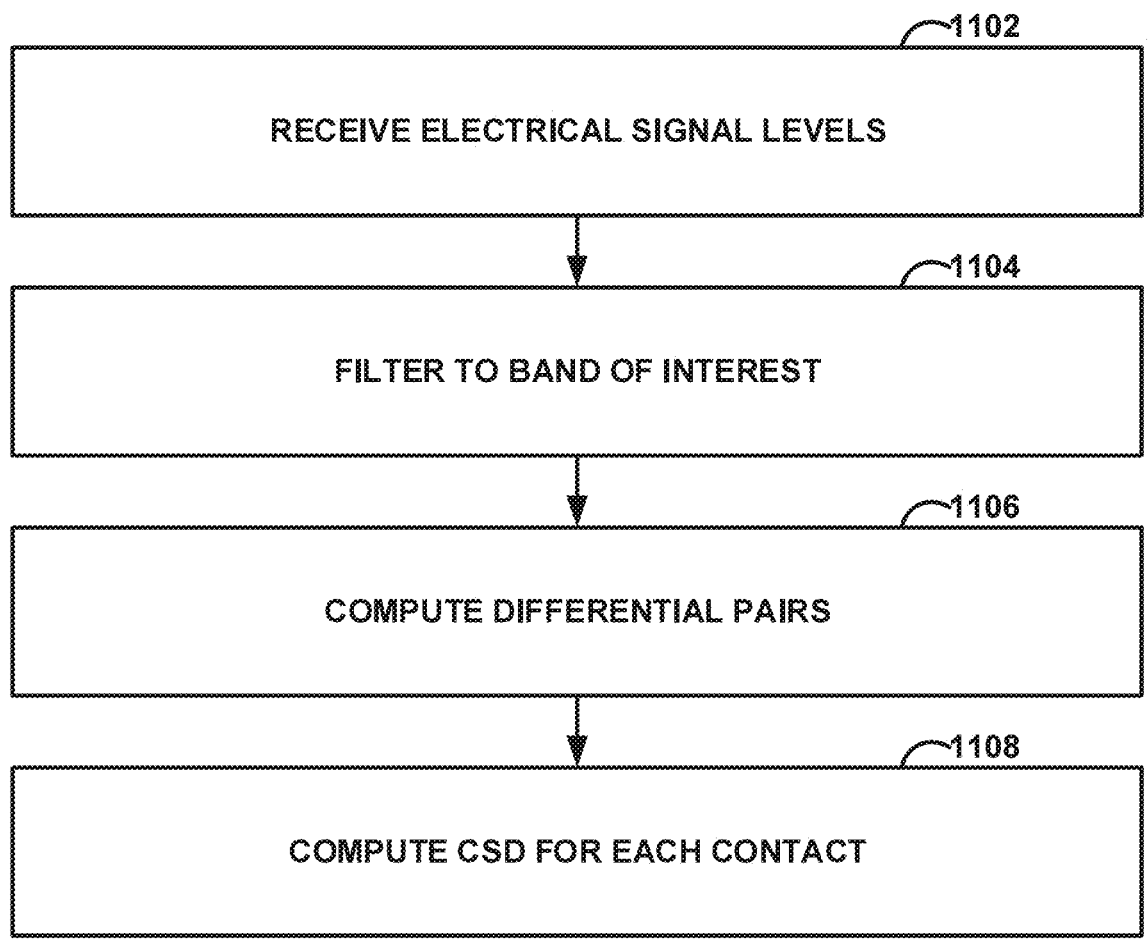
FIG. 11 is a flow diagram illustrating an example operation, in accordance with one or more techniques of this disclosure.

FIG. 11 is a flow diagram illustrating an example operation, in accordance with one or more techniques of this disclosure. In the example, processing circuitry 202 may receive information indicative of electrical signal levels (e.g., voltage measurements) from electrodes 116, 118 (1102). For example, memory 204 may store the electrical signal levels and processing circuitry 202 may receive the electrical signal levels from memory 204. Processing circuitry 202 may filter (e.g., bandpass filter) the received electrical signal levels to a band of interest (e.g., to filter out all frequency components except the beta band) (1104). Processing circuitry 202 may compute differential pairs based on the filtered electrical signal levels (e.g., $\Delta V_{i,i-1} - \Delta V_{i+1,i}$ and $\Delta V_{j,j-1} - \Delta V_{j+1,j}$) (1106). Processing circuitry 202 may compute CSD values for each contact (e.g., electrode) based on the computed differential pairs (e.g., determine $A_i(t)$ and $Z_i(t)$ and add them together to determine the CSD values) (1108).

FIG. 12 is a flow diagram illustrating another example operation, in accordance with one or more techniques of this disclosure. In the example, processing circuitry 202 may receive electrical signal levels (e.g., voltage measurements) from electrodes 116, 118 (1202). For example, memory 204 may store the electrical signal levels and processing circuitry 202 may receive the electrical signal levels from memory 204. Processing circuitry 202 may compute differential pairs based on the electrical signal levels (e.g., $\Delta V_{i,i-1} - \Delta V_{i+1,i}$ and $\Delta V_{j,j-1} - \Delta V_{j+1,j}$) (1204). Processing circuitry 202 may filter (e.g., bandpass filter) the results of the computed differential pairs to a band of interest (e.g., to filter out all frequency components except the beta band) (1206). Processing circuitry 202 may compute CSD values for each contact (e.g., electrode) based on the filtered computed differential pairs (e.g., determine $A_i(t)$ and $Z_i(t)$ and add them together to determine the CSD values) (1208). Processing circuitry 202 may compute aggregate measures and/or ranks (1210). An example of the aggregate measurement is the average level value (e.g., RMS value) and an example of the rank is the phase-magnitude representation, as described above.

Figure 13:
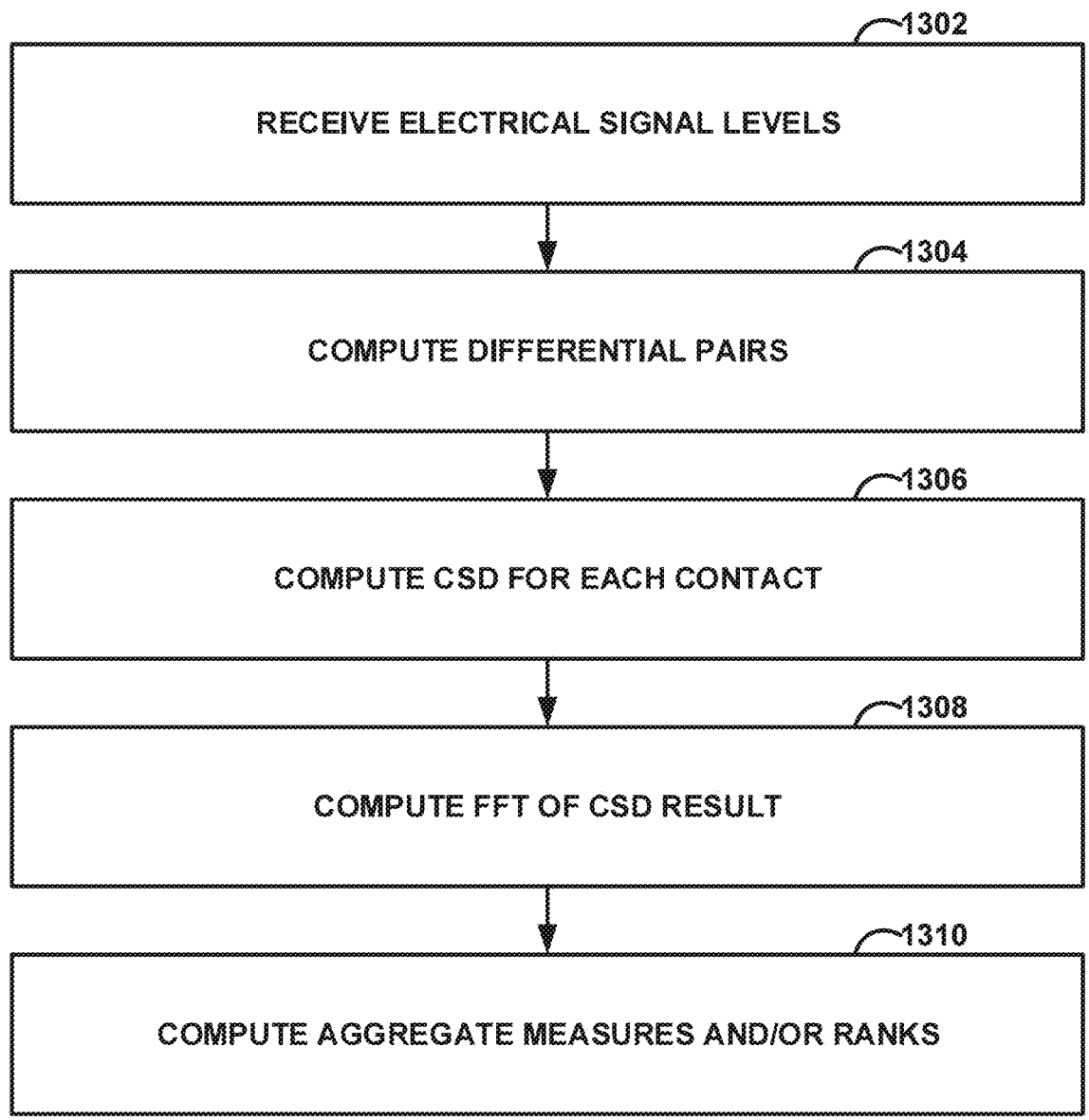
FIG. 13 is a flow diagram illustrating another example operation, in accordance with one or more techniques of this disclosure.

FIG. 13 is a flow diagram illustrating another example operation, in accordance with one or more techniques of this disclosure. In the example, processing circuitry 202 may receive electrical signal levels (e.g., voltage measurements) from electrodes 116, 118 (1302). For example, memory 204 may store the electrical signal levels and processing circuitry 202 may receive the electrical signal levels from memory 204. Processing circuitry 202 may compute differential pairs based on the electrical signal levels (e.g., $\Delta V_{i,i-1}-\Delta V_{i+1,i}$ and $\Delta V_{j,j-1}-\Delta V_{j+1,j}$) (1304). Processing circuitry 202 may compute CSD values for each contact (e.g., electrode) based on the computed differential pairs (e.g., determine $A_i(t)$ and $Z_i(t)$ and add them together to determine the CSD values) (1306). Processing circuitry 202 may determine a fast Fourier transform (FFT) (or other types of transform from time-domain to frequency domain) of the CSD values (1308). Processing circuitry 202 may compute aggregate measures and/or ranks (1310). An example of the aggregate measurement is the average level value (e.g., RMS value), and an example of the rank is the phase-magnitude representation, as described above.

For example, the FFT results in a phasor in the frequency domain. These phasors P, can be subtracted across electrodes in a similar manner to the time domain approach described above (e.g., $P_{i,i-1}-P_{i+1,i}$ and $P_{j,j-1}-P_{j+1,j}$). If phase is dropped and |P| is used, then an approximation results. This may be most relevant if horizontal components are computed separately from vertical. Also, the RMS value is one example, and other techniques to determine the average level value includes sum(abs(CSD(t))), sum(squared(CSD(t)), sqrt(sum (squared(CSD(t)−mean(CSD(t))))), etc. The average level value may be determined using other techniques as well.

Figure 14:
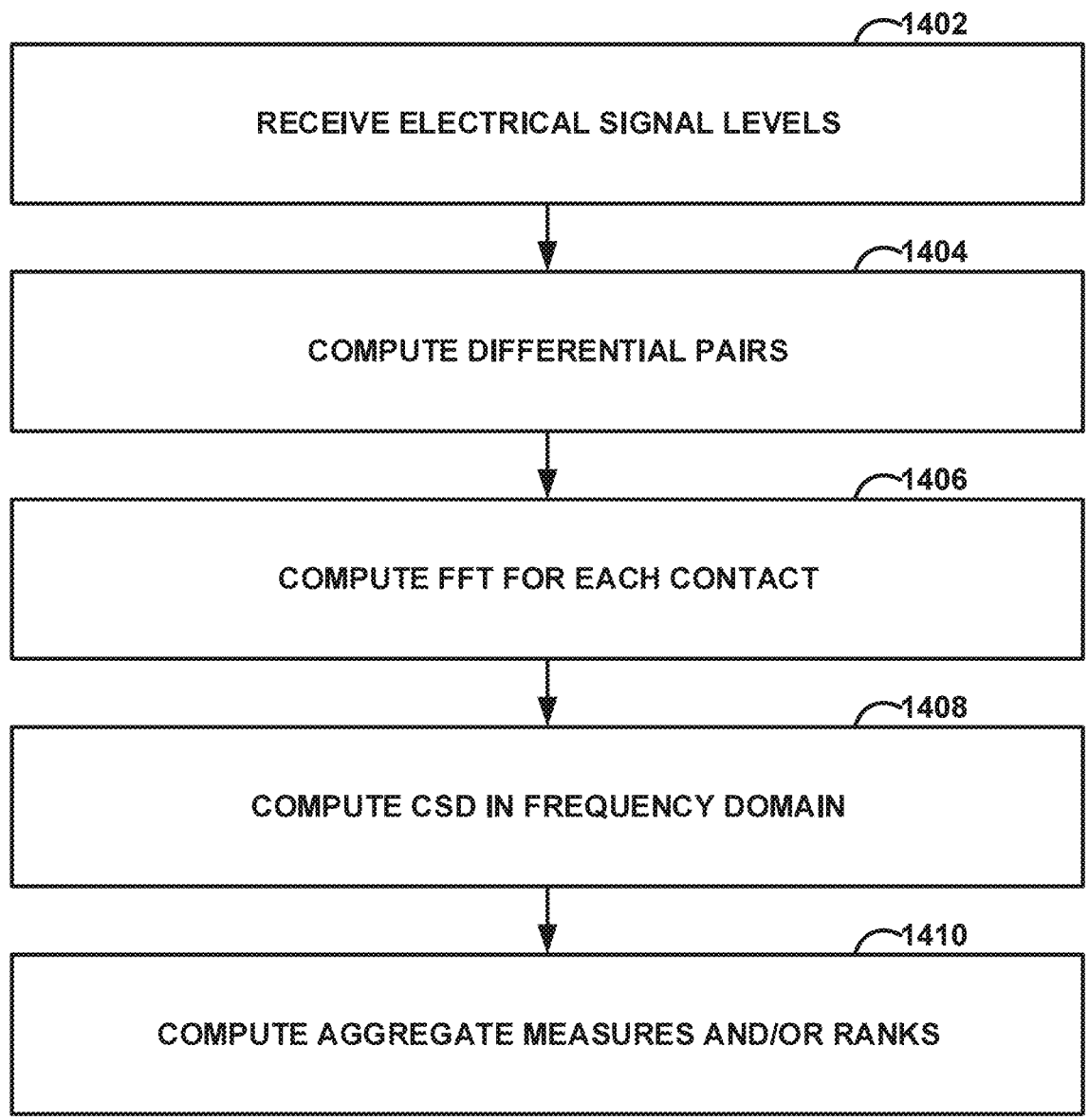
FIG. 14 is a flow diagram illustrating another example operation, in accordance with one or more techniques of this disclosure.

FIG. 14 is a flow diagram illustrating another example operation, in accordance with one or more techniques of this disclosure. In the example, processing circuitry 202 may receive electrical signal levels (e.g., voltage measurements) from electrodes 116, 118 (1402). For example, memory 204 may store the electrical signal levels and processing circuitry 202 may receive the electrical signal levels from memory 204. Processing circuitry 202 may compute differential pairs based on the electrical signal levels (e.g., $\Delta V_{i,i-1}-\Delta V_{i+1,i}$ and $\Delta V_{j,j-1}-\Delta V_{j+1,j}$) (1404). Processing circuitry 202 may determine a fast Fourier transform (FFT) (or other types of transform from time-domain to frequency domain) of the CSD values for each contact (1406). Processing circuitry 202 may compute the CSD values in the frequency domain as described above (1408). Processing circuitry 202 may compute aggregate measures and/or ranks (1410). An example of the aggregate measurement is the average level value (e.g., RMS value), and an example of the rank is the phase-magnitude representation, as described above. Also, the RMS value is one example, and other techniques to determine the average level value includes sum(abs(CSD (t))), sum(squared(CSD(t)), sqrt(sum(squared(CSD(t)−mean(CSD(t))))), etc. The average level value may be determined using other techniques as well.

Figure 15:
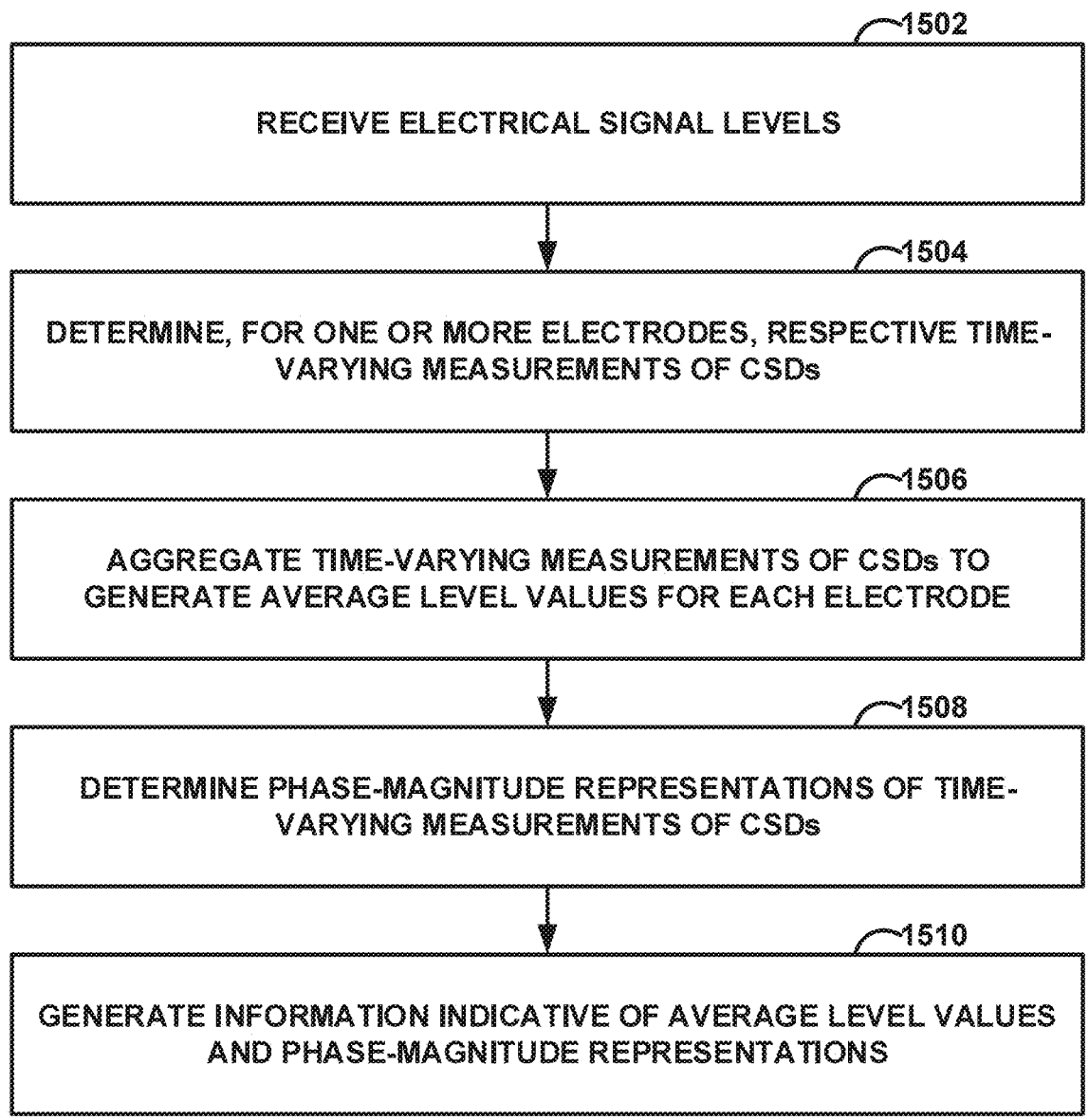
FIG. 15 is a flow diagram illustrating another example operation, in accordance with one or more techniques of this disclosure.

FIG. 15 is a flow diagram illustrating another example operation, in accordance with one or more techniques of this disclosure. For ease of description, the example is described with respect to processing circuitry 202 but the operations may be performed by processing circuitry 310 or a combination of processing circuitry 202 and processing circuitry 310.

Processing circuitry 202 may receive electrical signal levels (e.g., voltage measurements but other types of electrical signal levels are possible) from electrodes 116, 118 (1502). For example, memory 204 may store the electrical signal levels and processing circuitry 202 may receive the electrical signal levels from memory 204. The voltages at electrodes 116, 118 may be the result of an oscillatory signal source sinking or sourcing current, which forms a voltage on electrodes 116, 118.

Processing circuitry 202 may determine, for one or more electrodes of the plurality of electrodes 116 and 118, respective time-varying measurements of CSDs (1504). Processing circuitry 202 may perform the operations from any one or combination of (if applicable) the techniques described with respect to FIGS. 11-14.

As one example, processing circuitry 202 may determine, for one or more electrodes of the plurality of electrodes, respective first time-varying measurements based on second-order voltage differences between two electrodes that horizontally neighbor each electrode and a horizontal distance between the two horizontally neighboring electrodes and determine, for one or more electrodes of the plurality of electrodes, respective second time-varying measurements based on second-order voltage differences between two electrodes that vertically neighbor each electrode and a vertical distance between the two vertically neighboring electrodes. Processing circuitry 202 may determine respective time-varying measurements of the CSDs based on the respective first time-varying measurements and the second time-varying measurements.

As one example, processing circuitry 202 may scale the respective first-time varying measurements based on a radius of leads 114A, B that includes the respective electrodes of electrodes 116, 118 (e.g., determine $A_i(t)$ as described above by scaling by a factor of 1/r). Also, in some examples, processing circuitry 202 may scale at least one of the respective first time-varying measurements or the second time-varying measurements based on an anisotropy of local tissue impedance of the two horizontally neighboring electrodes or the two vertically neighboring electrodes. For instance, processing circuitry 202 may multiply the first and second time-varying measurements by of the CSDs by σ.

Processing circuitry 202 may be configured to aggregate, for one or more electrodes of the plurality of electrodes 116, 118, the respective time-varying measurements of the CSDs to generate respective average level values for one or more electrodes of the plurality of electrodes (1506). For example, processing circuitry 202 may be configured to determine, for one or more electrodes of the plurality of electrodes 116, 118, respective root-mean-square (RMS) values based on the respective first time-varying measurement and the second time-varying measurement. As described above, processing circuitry 202 may perform the operations of the following equation to generate the average level value as a way to aggregate the respective time-varying measurements of the CSDs.

$$CSD_i^{RMS} = \sigma \sqrt{\frac{1}{N}\sum_{j=1}^{N} |A_i(j)+Z_i(j)|^2}$$

In the above equation, i is the electrode of interest, and N is the number of data points in a temporal window of CSD values that are determined. Techniques other than techniques to calculate RMS values may be used to aggregate time-varying measurements of the CSD values.

In addition to generating the average level values, processing circuitry 202 may determine for one or more electrodes of the plurality of electrodes 116, 118, respective phase-magnitude representations of the time-varying measurements of the CSDs (1508). The respective phase-magnitude representations are indicative of respective magnitudes and phases of a particular frequency component of respective time-varying measurements of the CSDs, where the particular frequency component is a frequency component having a largest transform coefficient in a time-varying measurement of a CSD having a largest average level value. There may be various ways in which to determine the phase-magnitude representation. One of the example ways in which to determine the phase-magnitude representation is described above and in more detail with respect to FIG. 10.

In some examples, processing circuitry 202 may be configured to generate information indicative of the respective average level values and respective phase-magnitude representations (1510). As one example, processing circuitry 202 may output color information that represents the different average level values for the electrodes and output color information for the phase, where the opacity of the color for the phase is based on the magnitude. As another example, processing circuitry 202 may output average level values and phase-magnitude representations as data values.

In some examples, processing circuitry 202 may be configured to determine which electrodes of the one or more electrodes 116, 118 are most proximate, distal, or in between proximate and distal to an oscillatory signal source based on the generated information indicative of the respective average level values and the respective phase-magnitude representations. In such examples, processing circuitry 202 may generate and output information indicative of the determined electrodes.

The example techniques of FIG. 15 may be used for any one or combination of the following. The example techniques may be performed in a peripheral device (e.g., programmer 104) or cloud platform, and presented to the physician as an electrode selection, recommendation based on the largest/smallest value, or ranking of electrodes based on value and/or could be used to program IMD 106 to deliver stimulation with the electrode selection on a semi-automatic or automatic basis. The example techniques could be computed on IMD 106 and selected automatically. The example techniques could be computed on IMD 106 and presented on a peripheral device (e.g., programmer 104) or cloud platform, to the physician as a recommendation based on the largest/smallest value or ranking of electrodes based on value.

Figure 16:
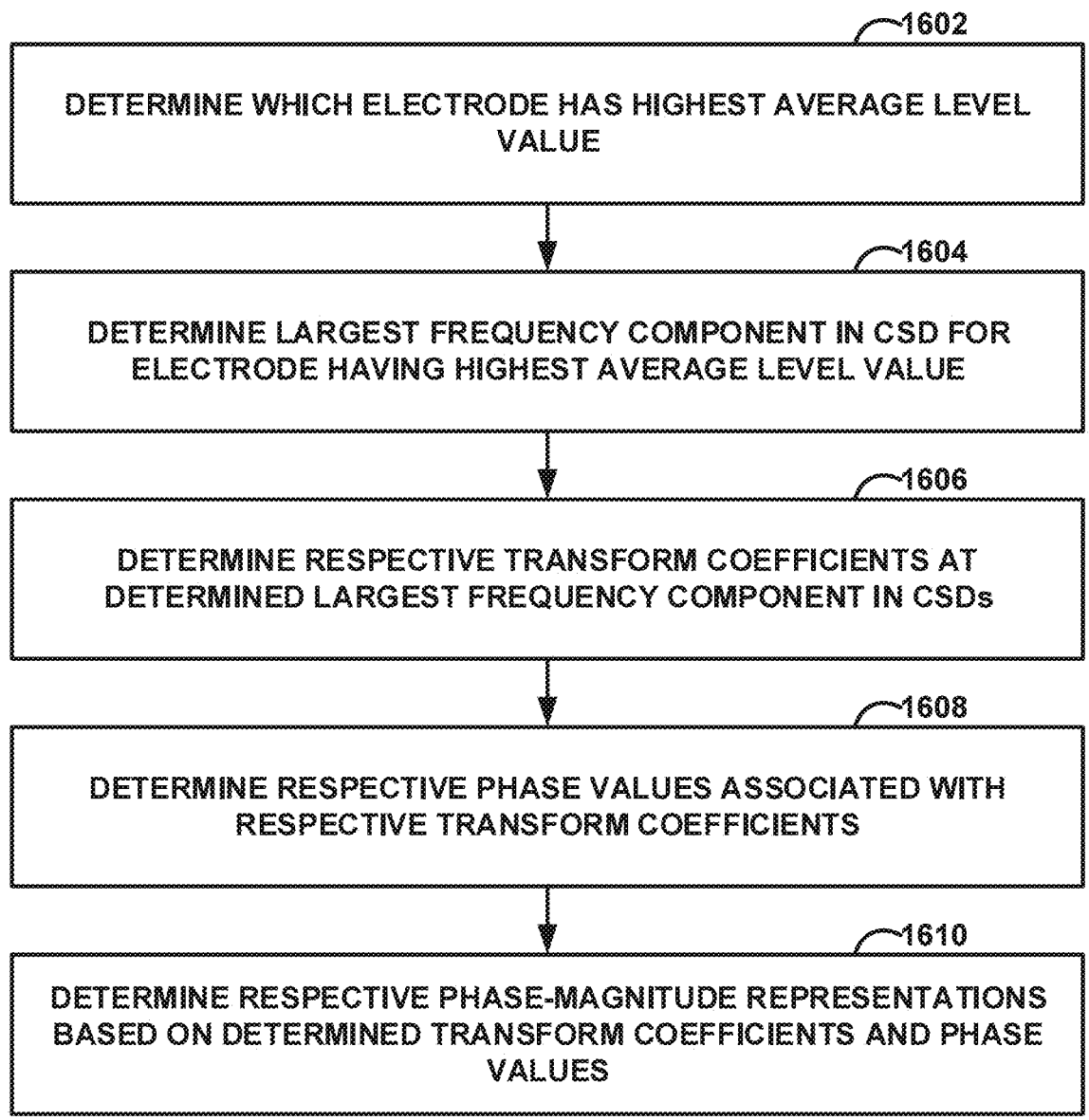
FIG. 16 is a flow diagram illustrating another example operation, in accordance with one or more techniques of this disclosure.

FIG. 16 is a flow diagram illustrating another example operation, in accordance with one or more techniques of this disclosure. For ease of description, the example is described with respect to processing circuitry 202 but the operations may be performed by processing circuitry 310 or a combination of processing circuitry 202 and processing circuitry 310.

Processing circuitry 202 may determine which electrode of electrodes 116, 118 has a highest average level value (1602) and determine a largest frequency component in the time-varying measurement of the CSD for the electrode having the highest average level value (1604). For example, assume that electrode X has the highest average level value of the time-varying measurements of the CSDs, and assume that frequency $w_0$ is the largest frequency component in the time-varying measurement CSD at electrode X.

Processing circuitry 202 may determine, for one or more electrodes of the plurality of electrodes 116, 118, respective transform coefficients (e.g., Fourier transform coefficients (FTCs)) at the determined largest frequency component (e.g., $w_0$) in respective time-varying measurements of the CSDs (1606). Processing circuitry 202 may also determine, for one or more electrodes of the plurality of electrodes 116, 118, respective phase values associated with the respective transform coefficients (1608). For example, assume that $A_{w0,i}$ is the FTC for frequency $w_0$ for the ith electrode, and is equal to $M_i e^{j\emptyset_i}$. In this example, $M_i$ is the magnitude of frequency component with frequency $w_0$, $\emptyset_i$ is the phase of the frequency component with frequency $w_0$ (e.g., phase value associated with transform coefficient), and j is the square-root of −1.

Processing circuitry 202 may determining respective phase-magnitude representations based on the determined respective transform coefficients and the respective phase values (1610). For example, processing circuitry 202 may utilize the $M_i$ and $\emptyset_i$ values to determine respective phase-magnitude representations for electrode i. As one example, processing circuitry 202 may determine a largest transform coefficient from the respective transform coefficients. For instance, $A_{w0,k}$ represents the largest transform coefficient and is the coefficient of electrode-k. $A_{w0,k}$ equals $M_k e^{j\emptyset_k}$. Processing circuitry 202 may determine a phase value associated with the determined largest transform coefficient (e.g., determine $\emptyset_k$). Processing circuitry 202 determine a difference between respective phase values associated with respective transform coefficients and the determined phase value associated with the determined largest transform coefficient (e.g., determine $(\emptyset_i - \emptyset_k)$). Processing circuitry 202 may determine respective phase-magnitude representations based on the determined difference and the determined respective transform coefficients (e.g., $A_{w0,i\_norm}$ equals $M_i e^{j(\emptyset_i - \emptyset_k)}$).

In some examples, the above example operations described with FIGS. 11-15 and elsewhere may be performed multiple times across multiple sub-bands (e.g., different frequency band) to detect locations of multiple sources that might appear as one big source. For instance, the above example techniques are described as being performed over the beta band, but in some examples, IMD 106 and/or programmer 104 may perform the example operations at different bands to identify multiple oscillatory sources.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A medical device system comprising:
a memory; and
processing circuitry in communication with the memory, the processing circuitry configured to:
receive a plurality of time-varying voltage signals, wherein each time-varying voltage signal of the plurality of time-varying voltage signals corresponds to one or more tissue regions of a plurality of tissue regions;
determine, based on each time-varying voltage signal of the plurality of time-varying voltage signals, a phase-magnitude representation indicative of a magnitude and a phase of a frequency component of the time-varying voltage signal;
determine, based on the phase-magnitude representation corresponding to each time-varying voltage signal of the plurality of time-varying voltage signals, a phase relationship corresponding to one or more tissue regions of the plurality of tissue regions; and
cause a therapy delivery circuit to deliver stimulation to cause the phase relationship to approach a target phase relationship for the one or more tissue regions.

2. The medical device system of claim 1,
wherein to receive the plurality of time-varying voltage signals, the processing circuitry is configured to:
sense a first set of time-varying voltage signals which correspond to a first tissue region of the one or more tissue regions; and
sense a second set of time-varying voltage signals which correspond to a second tissue region of the one or more tissue regions, and
wherein to determine the phase relationship between the one or more tissue regions, the processing circuitry is further configured to:
determine the phase relationship between the one or more tissue regions based on the first set of time-varying voltage signals and the second set of time-varying voltage signals.

3. The medical device system of claim 1,
wherein the processing circuitry is further configured to determine, based on the plurality of time-varying voltage signals, a time-varying measurement of current source density (CSD) corresponding to each tissue region of the plurality of tissue regions, and
wherein to determine the phase-magnitude representation based on each time-varying voltage signal of the plurality of time-varying voltage signals, the processing circuitry is configured to determine the phase-magnitude representation based on the respective time-varying measurement of CSD.

4. The medical device system of claim 3, further comprising a plurality of electrodes,
wherein the processing circuitry is configured to receive each time-varying voltage signal of the plurality of time-varying voltage signals via a respective electrode of the plurality of electrodes, and
wherein to determine the time-varying measurement of CSD corresponding to each tissue region of the plurality of tissue regions, the processing circuitry is further configured to:
determine, for each tissue region of the plurality of tissue regions, a respective first time-varying measurement based on a second-order voltage difference between two electrodes of the plurality of electrodes that horizontally neighbor the electrode corresponding to the tissue region and a horizontal distance between the two horizontally neighboring electrodes;
determine, for each tissue region of the plurality of tissue regions, a respective second time-varying measurement based on a second-order voltage difference between two electrodes of the plurality of electrodes that vertically neighbor the electrode corresponding to the tissue region and a vertical distance between the two vertically neighboring electrodes; and
determine the respective time-varying measurement of the CSD based on the respective first time-varying measurement and the respective second time-varying measurement.

5. The medical device system of claim 3, wherein the processing circuitry is further configured to:
determine a largest frequency component of a first time-varying measurement of the CSD corresponding to a first tissue region of the plurality of tissue regions;
determine a largest frequency component of a second time-varying measurement of the CSD corresponding to a second tissue region of the plurality of tissue regions;
calculate a Fourier transform of the first time-varying measurement of the CSD at the largest frequency component of the first time-varying measurement of the CSD, wherein the Fourier transform of the first time-varying measurement of the CSD indicates a first phase;
calculate a Fourier transform of the second time-varying measurement of the CSD at the largest frequency component of the second time-varying measurement of the CSD, wherein the Fourier transform of the second time-varying measurement of the CSD indicates a second phase; and
determine a difference between the first phase and the second phase in order to determine the phase relationship.

6. The medical device system of claim 1, wherein the processing circuitry is further configured to:
determine, based on one or more signals received by the processing circuitry, to initiate a phase relationship measurement; and
initiate the phase relationship measurement based on the determination to initiate the phase relationship measurement.

7. The medical device system of claim 6, wherein to determine to initiate, the processing circuitry is configured to:
receive information indicative of a user instruction to initiate the phase relationship measurement; and determine to initiate the phase relationship measurement based on receiving the information.

8. The medical device system of claim 6, wherein the processing circuitry is further configured to:
   determine a phase relationship measurement according to a phase relationship measurement program stored in the memory,
   wherein to determine to initiate, the processing circuitry is configured to determine, based on the phase relationship measurement program, to initiate the phase relationship measurement.

9. The medical device system of claim 1, further comprising an implantable medical device (IMD), wherein the IMD comprises the processing circuitry.

10. The medical device system of claim 9, wherein the IMD further comprises the memory.

11. The medical device system of claim 1, wherein the phase relationship indicates a first phase corresponding to a first tissue region of the plurality of tissue regions and a second phase corresponding to a second tissue region of the plurality of tissue regions.

12. The medical device system of claim 1, wherein the processing circuitry is further configured to:
   determine that the phase relationship corresponding to the one or more tissue regions is different from a target phase relationship corresponding to the one or more tissue regions; and
   determine, based on the phase relationship corresponding to the one or more tissue regions and the target phase relationship being different, one or more parameters of the stimulation delivered to cause the phase relationship to approach the target phase relationship for the one or more tissue regions.

13. A method comprising:
   receiving, by processing circuitry of a medical device system, a plurality of time-varying voltage signals, wherein each time-varying voltage signal of the plurality of time-varying voltage signals corresponds to one or more tissue regions of a plurality of tissue regions, and wherein the processing circuitry is in communication with a memory of the medical device system;
   determining, by the processing circuitry based on each time-varying voltage signal of the plurality of time-varying voltage signals, a phase-magnitude representation indicative of a magnitude and a phase of a frequency component of the time-varying voltage signal;
   determining, by the processing circuitry based on the phase-magnitude representation corresponding to each time-varying voltage signal of the plurality of time-varying voltage signals, a phase relationship corresponding to one or more tissue regions of the plurality of tissue regions; and
   causing, by the processing circuitry, a therapy delivery circuit to deliver stimulation to cause the phase relationship to approach a target phase relationship for the one or more tissue regions.

14. The method of claim 13,
   wherein receiving the plurality of time-varying voltage signals comprises:
      sensing, by the processing circuitry, a first set of time-varying voltage signals which correspond to a first tissue region of the one or more tissue regions; and
      sensing, by the processing circuitry, a second set of time-varying voltage signals which correspond to a second tissue region of the one or more tissue regions, and
   wherein determining the phase relationship between the one or more tissue regions comprises:
      determining, by the processing circuitry, the phase relationship between the one or more tissue regions based on the first set of time-varying voltage signals and the second set of time-varying voltage signals.

15. The method of claim 13, further comprising:
   determining, by the processing circuitry based on the plurality of time-varying voltage signals, a time-varying measurement of current source density (CSD) corresponding to each tissue region of the plurality of tissue regions, and
   wherein determining the phase-magnitude representation based on each time-varying voltage signal of the plurality of time-varying voltage signals comprises determining, by the processing circuitry, the phase-magnitude representation based on the respective time-varying measurement of CSD.

16. The method of claim 15, further comprising:
   receiving, by the processing circuitry, each time-varying voltage signal of the plurality of time-varying voltage signals via a respective electrode of a plurality of electrodes, and
   wherein determining the time-varying measurement of CSD corresponding to each tissue region of the plurality of tissue regions comprises:
      determining, by the processing circuitry for each tissue region of the plurality of tissue regions, a respective first time-varying measurement based on a second-order voltage difference between two electrodes of the plurality of electrodes that horizontally neighbor the electrode corresponding to the tissue region and a horizontal distance between the two horizontally neighboring electrodes;
      determining, by the processing circuitry for each tissue region of the plurality of tissue regions, a respective second time-varying measurement based on a second-order voltage difference between two electrodes of the plurality of electrodes that vertically neighbor the electrode corresponding to the tissue region and a vertical distance between the two vertically neighboring electrodes; and
      determining, by the processing circuitry, the respective time-varying measurement of the CSD based on the respective first time-varying measurement and the respective second time-varying measurement.

17. The method of claim 13, further comprising:
   determining, based on one or more signals received by the processing circuitry, to initiate a phase relationship measurement; and
   initiating the phase relationship measurement based on the determination to initiate the phase relationship measurement.

18. The method of claim 17, wherein determining to initiate the phase relationship measurement comprises:
   receiving, by the processing circuitry, information indicative of a user instruction to initiate the phase relationship measurement; and
   determining, by the processing circuitry, to initiate the phase relationship measurement based on receiving the information.

19. The method of claim 17, further comprising:
- determining, by the processing circuitry, a phase relationship measurement according to a phase relationship measurement program stored in the memory,
- wherein determining to initiate the phase relationship measurement comprises determining, by the processing circuitry based on the phase relationship measurement program, to initiate the phase relationship measurement.

20. A computer-readable storage medium comprising instructions that when executed cause one or more processors to:
- receive a plurality of time-varying voltage signals, wherein each time-varying voltage signal of the plurality of time-varying voltage signals corresponds to one or more tissue regions of a plurality of tissue regions;
- determine, based on each time-varying voltage signal of the plurality of time-varying voltage signals, a phase-magnitude representation indicative of a magnitude and a phase of a frequency component of the time-varying voltage signal;
- determine, based on the phase-magnitude representation corresponding to each time-varying voltage signal of the plurality of time-varying voltage signals, a phase relationship corresponding to one or more tissue regions of the plurality of tissue regions; and
- cause a therapy delivery circuit to deliver stimulation to cause the phase relationship to approach a target phase relationship for the one or more tissue regions.

* * * * *